US011414491B2

(12) United States Patent
Russell et al.

(10) Patent No.: US 11,414,491 B2
(45) Date of Patent: Aug. 16, 2022

(54) TARGETING PD-L1 ON TUMOR CELLS

(71) Applicant: Mayo Foundation for Medical Education and Research, Rochester, MN (US)

(72) Inventors: Stephen James Russell, Rochester, MN (US); Autumn J. Schulze, Rochester, MN (US); Arun Ammayappan, Rochester, MN (US); Kah-Whye Peng, Rochester, MN (US); Camilo Ayala Breton, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 463 days.

(21) Appl. No.: 16/302,403

(22) PCT Filed: May 18, 2017

(86) PCT No.: PCT/US2017/033320
§ 371 (c)(1),
(2) Date: Nov. 16, 2018

(87) PCT Pub. No.: WO2017/201281
PCT Pub. Date: Nov. 23, 2017

(65) Prior Publication Data
US 2019/0169296 A1  Jun. 6, 2019

Related U.S. Application Data

(60) Provisional application No. 62/338,466, filed on May 18, 2016.

(51) Int. Cl.
*A61K 48/00* (2006.01)
*C07K 16/28* (2006.01)
*C07K 14/005* (2006.01)
*C12N 15/86* (2006.01)
*A61P 35/00* (2006.01)
*A61K 35/17* (2015.01)
*C12N 15/85* (2006.01)
*C12N 15/00* (2006.01)

(52) U.S. Cl.
CPC .......... *C07K 16/2827* (2013.01); *A61K 35/17* (2013.01); *A61P 35/00* (2018.01); *C07K 14/005* (2013.01); *C07K 16/2809* (2013.01); *C07K 16/2896* (2013.01); *C12N 15/85* (2013.01); *C12N 15/86* (2013.01); *A61K 48/00* (2013.01); *C07K 16/2818* (2013.01); *C07K 2317/31* (2013.01); *C07K 2317/622* (2013.01); *C07K 2319/02* (2013.01); *C07K 2319/33* (2013.01); *C12N 15/00* (2013.01); *C12N 2710/10343* (2013.01); *C12N 2760/18422* (2013.01); *C12N 2760/18423* (2013.01); *C12N 2760/18433* (2013.01); *C12N 2760/20243* (2013.01)

(58) Field of Classification Search
None
See application file for complete search history.

(56) References Cited

U.S. PATENT DOCUMENTS

| 6,297,004 | B1 * | 10/2001 | Russell ............... C12N 15/1037 435/5 |
| 7,317,004 | B2 | 1/2008 | Russell et al. |
| 7,846,429 | B2 | 12/2010 | Russell et al. |
| 7,943,743 | B2 | 5/2011 | Korman et al. |
| 10,407,502 | B2 * | 9/2019 | Waksal ............... C07K 14/7155 |
| 2002/0132983 | A1 | 9/2002 | Junghans |
| 2015/0210769 | A1 | 7/2015 | Freeman et al. |
| 2015/0337038 | A1 | 11/2015 | Korman et al. |
| 2015/0344567 | A1 | 12/2015 | Kawasaki et al. |

FOREIGN PATENT DOCUMENTS

| CN | 104829729 | 8/2015 | |
| WO | WO 2015/179918 | 3/2015 | |
| WO | WO 2015/128313 A1 * | 9/2015 | .......... A61K 35/768 |
| WO | WO 2016/008976 | 1/2016 | |
| WO | WO 2016/009017 | 1/2016 | |
| WO | WO 2016/020065 | 2/2016 | |

OTHER PUBLICATIONS

Ota et al (Clinical Cancer Res. vol. 21, No. 17, Sep. 1, 2015, pp. 4014-4021) (Year: 2015).*
Extended European Search Report in European Application No. 17800167.3 dated Jan. 27, 2020, 17 pages.
Batlevi et al., "Novel immunotherapies in lymphoid malignancies," Nat. Rev. Clin. Oncol., Jan. 2016.
Brentjens et al., "CD19-targeted T cells rapidly induce molecular remissions in adults with chemotherapy-refractory acute lymphoblastic leukemia," Sci. Transl. Med., 5(177):177ra38, Mar. 2013.
Cosset and Russell, "Targeting retrovirus entry," Gene therapy, 3(11):946-56, Nov. 1996.
Davila et al., "Efficacy and toxicity management of 19-28z CAR T cell therapy in B cell acute lymphoblastic leukemia," Sci. Transl. Med., 6(224):224ra25, Feb. 2014.
Diaz et al., "Oncolytic Immunovirotherapy for Melanoma Using Vesicular Stomatitis Virus," Cancer Res., 67(6):2840-8, Mar. 2007.

(Continued)

*Primary Examiner* — Celine X Qian
(74) *Attorney, Agent, or Firm* — Fish & Richardson P.C.

(57) ABSTRACT

This document relates to materials and methods for treating cancer. For example, this document provides materials and methods for using PD-L1 targeting domains in bispecific chimeric polypeptides, chimeric transmembrane polypeptides, genetically modified viruses, nucleic acid vectors, and/or fusion-inducing cells to treat cancer.

16 Claims, 23 Drawing Sheets

Specification includes a Sequence Listing.

(56) References Cited

OTHER PUBLICATIONS

Douglas et al., "A system for the propagation of adenoviral vectors with genetically modified receptor specificities," Nat. Biotechnol., 17(5):470-475, May 1999.

Engeland et al., "CTLA-4 and PD-L1 checkpoint blockade enhances oncolytic measles virus therapy," Mol. Ther., 22(11):1949-1959, Nov. 2014.

International Search Report & Written Opinion in International Application No. PCT/US2017/033320 dated Oct. 5, 2017, 18 pages.

Kochenderfer et al., "B-cell depletion and remissions of malignancy along with cytokine-associated toxicity in a clinical trial of anti-CD19 chimeric-antigen-receptortransduced T cells," Blood, 119(12):2709-2720, Mar. 2012.

Krupka et al., "Blockade of the PD-1/PD-L1 axis augments lysis of AML cells by the CD33/CD3 BiTE antibody construct AMG 330: reversing a T-cell-induced immune escape mechanism," Leukemia, 30(2):484, Feb. 2016.

Nakamura et al., "Antibody-targeted cell fusion," Nat. Biotechnol., 22(3):331-336, Mar. 2004.

Nakamura et al., "Rescue and propagation of fully retargeted oncolytic measles viruses," Nat. Biotechnol., 23(2):209-214, Feb. 2005.

Porter et al., "Chimeric antigen receptor-modified T cells in chronic lymphoid leukemia," N. Engl. J. Med., 365(8):725-733, Aug. 2011.

Robbins et al., "Tumor regression in patients with metastatic synovial cell sarcoma and melanoma using genetically engineered lymphocytes reactive with NY-ESO-1," J. Clin. Oncol., 29(7):917-924, Mar. 2011.

Zhang et al., "Bi-specific antibodies targeting signaling pathway crosstalk are a new breast cancer immunotherapeutic strategy," In Cancer Research, 75(9), 615 Chestnut St, 17th Floor, Philadelphia, PA 19106-4404 USA: Amer Assoc Cancer Research, May 1, 2015.

Ahmad et al, "scFv Antibody: Principles and Clinical Application," Clin. Dev. Immunology, 2012, 2012:980250, 16 pages.

Ammavappan et al., "Neuroattenuation of vesicular stomatitis virus through picornaviral internal ribosome entry sites," J. Virology, Mar. 2013, 87(6):3217-3228.
Baghian et al., "Truncation of the carboxy-terminal 28 amino acids of glycoprotein B specified by herpes simplex virus type 1 mutant ambl511-7 causes extensive cell fusion," J. Virology, Apr. 1993, 67(4):2396-2401.
Bigelow et al., "Immunohistochemical staining of B7-H1 (PD-L1) on paraffin-embedded slides of pancreatic adenocarcinoma tissue," J. Vis. Experiments, Jan. 3, 2013, 3(71):4059, 6 pages.
Brody et al., "Postassembly cleavage of a retroviral glycoprotein cytoplasmic domain removes a necessary incorporation signal and activates fusion activity," J. Virology, Jul. 1, 1994, 68(7):4620-4627.
Curiel et al., "Blockade of B7-H1 improves myeloid dendritic cell-mediated antitumor immunity," Nat. Medicine, May 2003, 9(5):562-567.
Dong et al., "Costimulating aberrant T cell responses by B7-H1 autoantibodies in rheumatoid arthritis," J. Clin. Investigation, Feb. 2003, 111(3):363-370.
Gage et al., "Syncytium-inducing mutations localize to two discrete regions within the cytoplasmic domain of herpes simplex virus type 1 glycoprotein B," J. Virology, Apr. 1, 1993, 67(4):2191-2201.
Mulligan et al., "Cytoplasmic domain truncation enhances fusion activity by the exterior glycoprotein complex of human immunodeficiency virus type 2 in selected cell types," J. Virology, Jun. 1, 1992, 66(6):3971-3975.
Pique et al., "The cytoplasmie domain of the human T-cell leukemia virus type I envelope can modulate envelope functions in a cell type-dependent manner," J. Virology, Jan. 1, 1993, 67(1):557-561.
Rein et al., "Function of the cytoplasmic domain of a retroviral transmembrane protein: p15E-p2E cleavage activates the membrane fusion capability of the murine leukemia virus Env protein," J. Virology, Mar. 1, 1994, 68(3):1773-1781.
Sznol et al., "Antagonist Antibodies to PD-1 and B7-H1 (PD-L1) in the Treatment of Advanced Human Cancer," Clin. Cancer Research, Mar. 1, 2013, 19(5):1021-1034.
Thompson et al., "Tumor B7-H1 is associated with poor prognosis in renal cell carcinoma patients with long-term follow-up," Cancer Research, Apr. 1, 2006, 66(7):3381-3385.

* cited by examiner

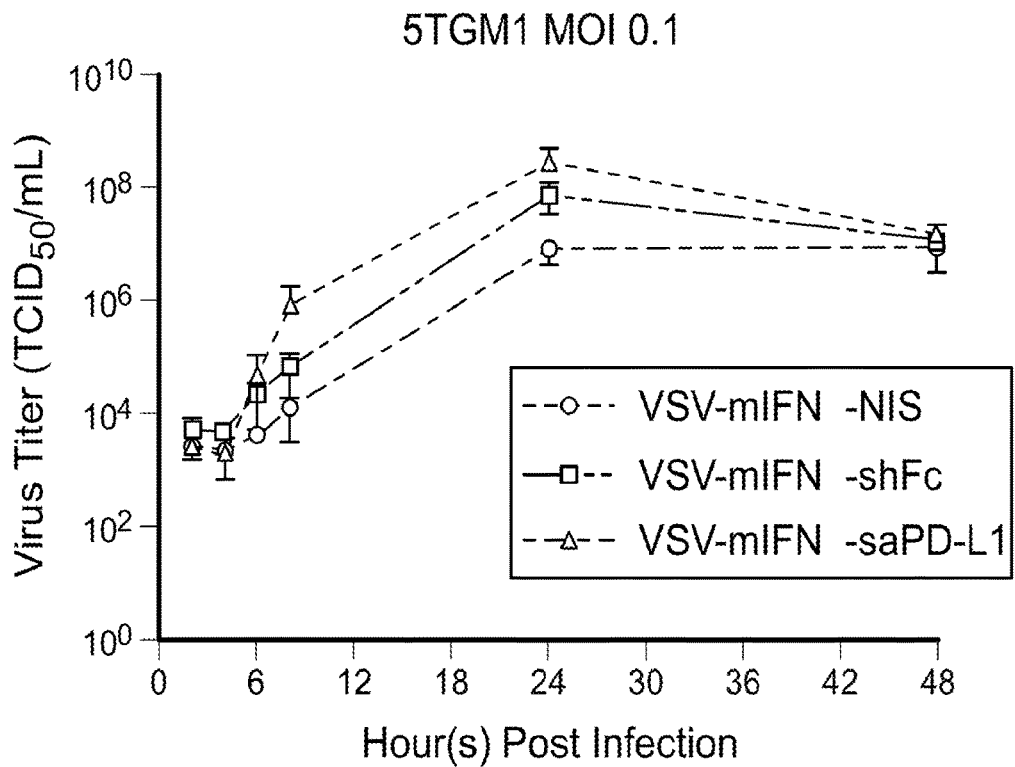
FIG. 3 Contin.
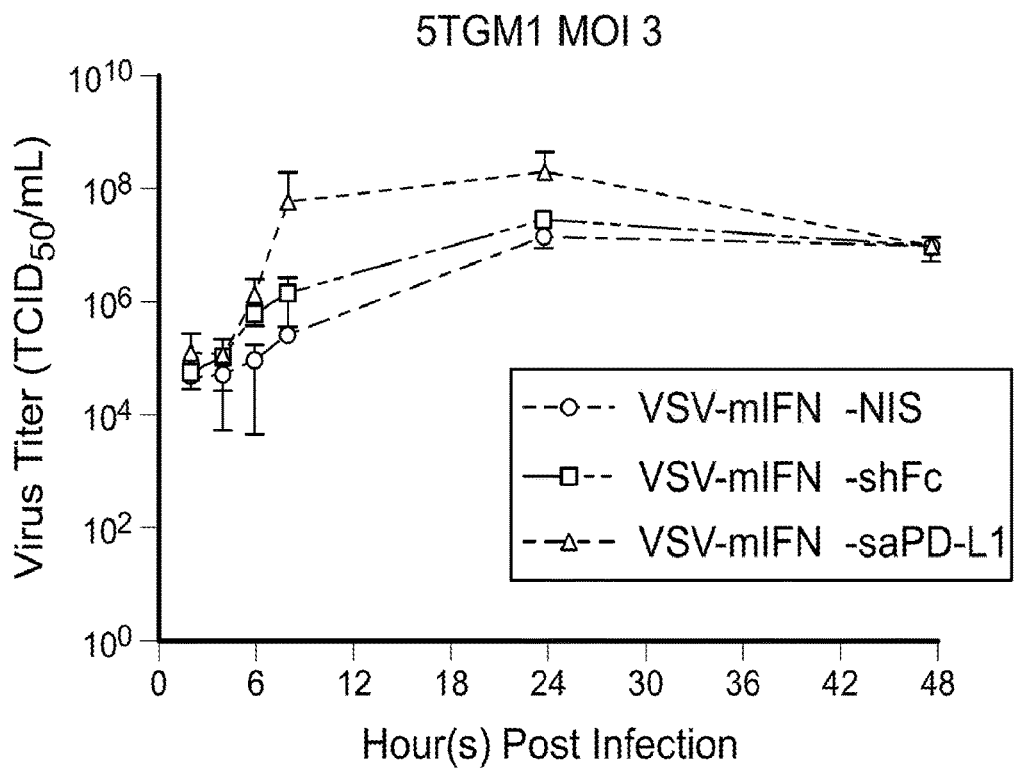
*Similar growth in BHKs
FIG. 3 Contin.

```
  1  ctaatacgac tcactatagg gcaagcagtg gtatcaacgc agagtacatg ggggaaatac accagaccag
     >>.................................5'UTR....................................>
 71  catgggcatc aagatggaga cacattctca ggtctttgta tacatgttgc tgtggttgtc tggtgttgaa
     >...5'UTR...>>
                    >>....................Leader Peptide.......................>
141  ggagacattg tgatgaccca gtctcacaaa ttcatgtcca catcaatagg agacagagtc agcatcacct
     >>> Leader Peptide
          >>...........................V Region..............................>
211  gcaaggccag tcaggatgtg ggtactggtg tagcctggta tcaacagaga ccaggacaat ctcctaaatt
     >..............................V Region................................>
              >>......CDR1.....>>
281  actgatttac tggtcatcca cccggcacac tggagtccct gatcgcttca caggcagtgg atctgggaca
     >..............................V Region................................>
           >>CDR2.>>
351  gatttcactc tcaccattag caatgtgcag tctgaagact tggcagatta tttctgtcaa caatatagta
     >..............................V Region................................>
                                                                 >>...CDR3....>
421  gttatcctct gtacacattc ggaggggggga ccaagctgga aataaaacgg
          >.......>> V Region                                   SEQ ID NO:1
     >......CDR3.....>>
              >>...............J Region................>>
```

FIG. 5A

```
  1  ctaatacgac tcactatagg gcaagcagtg gtatcaacgc agagtacatg gggacctatg atcagtgtcc
     >...................................5'UTR...............................>
 71  tctccacagt ctctgaagac actgactcta accatgggat gcagatggat ctttcttttc ctcctgtcag
     >..........5'UTR.............>>
                                          >>................Leader................>
141  ggactgcagg tgtccattgc caggttcaac tgcagcagtc tcgacctgag ctggtgaagc ctggggcttt
     >......Leader......>>
                                 >>....................V region....................>
211  agtgaagata tcctgcaagg cctctggtta caccttcgca ggctacgata taaactgggt gaaacagagg
     >....................V region....................>
                                   >>.........CDR1.........>>
281  cctggacagg gacttgagtg gattggatgg attttttcctg gcgatggtag tactgaatac gatgaaaaat
     ....................V region....................>
                                   >>.........CDR2.........>>
351  tcaagggcaa ggccacactc actgcagaca atcctccag cacggcctac atgcagctca gcagcctgac
     >....................V region....................>
421  ttctgagaac tctgcagtct atttctgtgc ggtgggatcc tacggtagtg cgcgttcttt tgtttactgg
     >...V region...>>
                      >>..............D Region..............>>
                              >>.................CDR3..................>>
                                                             >>...J Region.....>
491  ggccaaggga ctctggtcac tgtctctgca gccaaaacga caccccatc tgtctatcca ctggcccctg
     >...........J Region..........>>
```

SEQ ID NO:2

FIG. 5B

FIG. 6
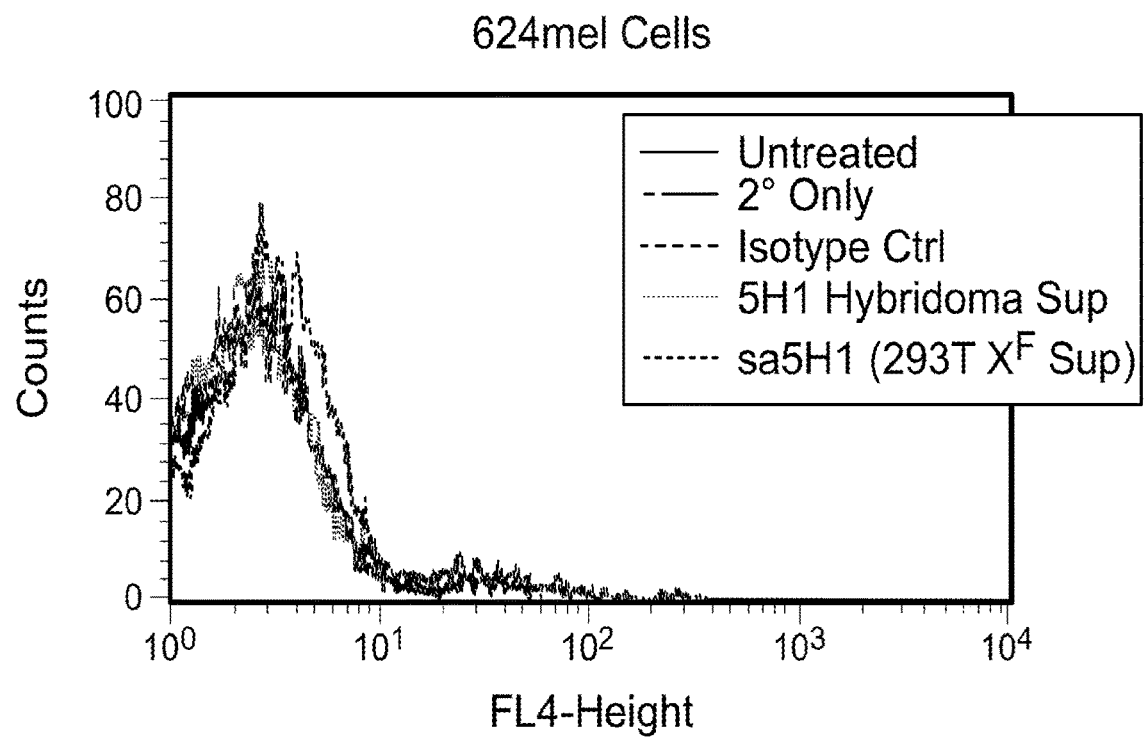
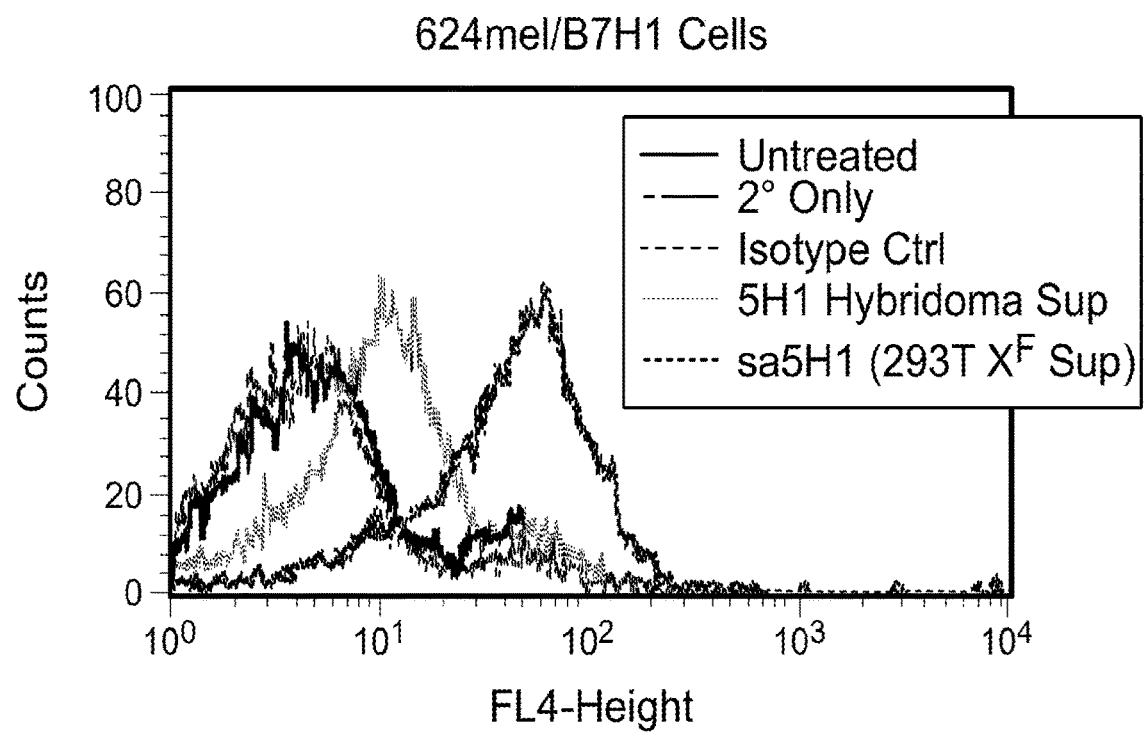

Bsu36I
c-Myc
Linker
BiTE: PDL1-mCD3 (Mouse)

CCTTAGGCGGCGCCACCATGGAGACAGACACACTCCTGCTATGGGTACTGCTCCTGGTTCCAGTTCCACTGG
TGACGACATCCAAATGACCCAGAGTCCATCTAGTCTGTCTGCTAGTGTCGGTGATAGGGTCACTATTACTTGCAG
GGCCTCCCAGGACGTGTCTGTATTCCGGAGTTCCGTCTTGGTACCAACAGAAGCCCGGAAAGGCTCCCAAACTGCTGATCTA
CTCCGCCAGCTTTCTGTATTCCGGAGTTCCGTCAACACCAGAGCGGACTTCACTGGGAGTGGGTCTGGGACTGAAGATTCACACTCAC
AATAAGCAGCCACCAAGGTGGAGTGTTCGCAACCAAGCGCGGTGGGATCAAGGGTACCTGTCAACAGTATTTCACCAGCCACCTTTGG
GCAGGGCACCAAGGTGGAGATCAAGCGGGGTGGGATCCGGTTGGTGGGATCCAGGCGCGGTGGAGGTGGCAGGAGGTGGCGGATCCGA
AGTTCAGCTTTTCACGGCATACCTTCAGATTATTGGGGACAGTACATATGAATTCCCTGGGAGAGAAGGAGTTCACCATCAGCGCAGACACCTCCAAG
TAGCCCCCTACGGCATACCTTCAGATTATTGGGGACAGTACATATGAATTCCCTGGGAGAGAAGGAGTTTACCATCAGCGACACGTCGAA
GAACACCGCCTACCTGCAGATGAATAGCCTCAGAGCTGAGGACACCGCCGTGTATTACTGTGCCAGGCGCCAGACTGTGCCAGCCTC
GCCCTGCGCAGGTCGAGCTGGACTGGGGCCAAGGGACCCTGGTCACCGTCTCAAGTGGTGGAGGCGGTTCAGGCGGAGGTGGCTCTGGCGGT
GGCGGATCGGATATTCAGATGACCCAGAGCCCAAGCAGCCTGAGCGCCAGCGTGGGCGATAGAGTGACCATTAATTGCAGGGCCAGTCAG
GATGTGAGCACAGCCGTGGCCTGGTATCAGCAGAAACCAGGCAAGGCCCCCAAGCTGCTGATCTATTCTGCTTCCTTCCTGTACAGCGGAGTG
CCCTCAAGATTCTCTGGATCCGGCTCTGGCACCGATTTCACACTGACCATCAGCAGCCTCCAGCCTGAAGATTTTGCAACATATTATTGCCAG
CAGTATAATAATTACCCATGGACATTCGGCCAGGGCACAAAGCTCGAAATCAAACGGACCACCACCACCACCCTAGTGGCAAATCAACGGAGGATCTC
GGACCTGTAGCCTGAGG    SEQ ID NO:5

METDTLLLWVLLLWVPGSTGDDIQMTQSPSSLSASVGDRVTITCRASQDVSTAVAWYQQKPGKAPKLLIYSASFL
YSGVPSRFSGSGSGTDFTLTISSLQPEDFATYYCQQYLYHPATFGQGTKVEIKRGGGSGGGGSGGGGSEVQLVE
SGGGLVQPGGSLRLSCAASGFTFSDSWIHWVRQAPGKGLEWVAWISPYGGSTYYADSVKGRFTISADTSKNTAYL
QMNSLRAEDTAVYYCARRHWPGGFDYWGQGTLVTVSALSSGGGGSGGGGSGGGGSEVQLVESGGGLVQPGKSLKLSCEASGFTFS
GYGMHWVRQAPGRGLESVAYITSSSINIKYADAVKGRFTVSRDNAKNLLFLQMNILKSEDTAMYYCARFDWDKNY
WGQGTMVTVSSAGGGGSGGGGSGGGGSDIQMTQSPSSLPASLGDRVTINCQASQDISNYLNWYQQKPGKAPKLLI
YYTNKLADGVPSRFSGSGSGRDSSFTISSLESEDIGSYYCQQYNYNYPWTFGPGTKLEIKRSSEQKLISEEDL
                                                                    SEQ ID NO:6

FIG. 13A

BiTE: PDL1-hCD3 (Human)

CCTTAGGCGCGCCACCATGGAGACAGACACTCCTGCTACTGCTCTGGGTTCTCCACTGG
TGACGACATCCAAATGACCCAGAGTCCATCCAGTCTCAGTGCCTCTGTAGGGTCACTATTACTTGCAG
GGCCTCCCAGAGCTGTCAACTGTCTGTATTCCGAGGACTTTCCGTCCAACTACAGTTCAACACTCAC
CTCCGCCAGCTTTCTCTACAACCAGGTGAAATCAAGCGCGGCCTTTGGATCACATATTACGCAGAGA
ATAAGCAGCCCAAGGTGGAAGTCAAGCGCGGCCTGGGATCAGGTGGTGGTGGATCCGGA
GGTTCAGCTTGTGCTGAGTCCTGGAGAGACAGCGTGAAGGGTCTTGAGTGGTCATGGAT
TAGCCCCTACGGCGGCAGTACATATTACGCGGATAGCGTGAAAGGGAGGTTTACCATCAGCGTCGAA
GAACACCGCCATACCTCAGATTATTGTGGGACAGGGAACTCTAGTAGCGCCGTGTCTTCGGC
GCCTGGCGGCTTCGATTATTGGGACAGGGAACTCTAGTAGCGCCGTGTCTGCGGCCAG
CCAGGTGCAGCTGCAGCAGAGCGGCCCAGGTGTCACTGGCCCTGTGTCCCAGCTGTGAAGGATCCGCC
CGGCTACACCTTCACCAGGCTACAACAGGTGTCAAGGAAGGCCACCTGTGAGCCCCAGTACTA
CATCAACAACAACAACGGCCGCCCACTGCCAGCCAAGGACAAGTTCAAGGACAAGGCCACCCTGACCGCC
GACAAGAGCAGCAGCAGCACGCTGGAGCGCCAGATCGTGCTGCAGCTGCACAACAACAACCGCGTGACCGC
CGGCCTGGACCTGCAACAAGAGCAGAGCAGCGGCCATCATGACCAGCATGGACCCCCAGCCC
CGGCGAGAGCGCTACTACGCCCTGAGCGACACCTTCAACTGCCCGCCACCTACTGCGCCAG
CACCAGCAGCAGCAGCAGCAGGACCATCAGCAGGGCCACCAAGGGCGACAACAGGCCCACCAGCAG
GAGCAGCAGAAGCTGATCAGCAGGAGGAGGACCCTGAGCTAGCCCTGAGG SEQ ID NO:7

METDTLLWVLLLWVPGSTGDDIQMTQSPSSLSASVGDRVTITCRASQDVSTAVAWYQQKPGKAPKLLIYSASFL
YSGVPSRFSGSGSGTDFTLTISSLQPEDFATYYCQQYLYHPATFGQGTKVEIKRGGGSGGGGSGGGGSEVQLVE
SGGGLVQPGGSLRLSCAASGFTFSDSWIHWVRQAPGKGLEWVAWISPYGGSTYYADSVKGRFTISADTSKNTAYL
QMNSLRAEDTAVYYCARRHWPGFDYWGQGTLVTVSALSSGGGGSGVQLQQSGAELARPGASVKMSCKASGYTFT
RYTMHWVKQRPGQGLEWIGYINPSRGYTNYNQKFKDKATLTTDKSSSTAYMQLSSLTSEDSAVYYCARYYDDHYC
LDYWGQGTTLTVSSAGGGSGGGGSGGGGSSGTSYSLTISGMEAEDAATYYCQQWSSNPFTFGSGTKLEINRADTAPTSSEQKLI
SEEDL SEQ ID NO:8

SEQUENCE LISTING

```
<160> NUMBER OF SEQ ID NOS: 8

<210> SEQ ID NO 1
<211> LENGTH: 469
<212> TYPE: DNA
<213> ORGANISM: Mus musculus

<400> SEQUENCE: 1
ctaatacgac tcactatagg gcaagcagtg gtatcaacgc agagtacatg ggggaaatac      60
accagaccag catgggcatc aagatggaga cacattctca ggtctttgta tacatgttgc     120
tgtggttgtc tggtgttgaa ggagacattg tgatgaccca gtctcacaaa ttcatgtcca     180
catcaatagg agacagagtc agcatcacct gcaaggccag tcaggatgtg ggtactggtg     240
tagcctggta tcaacagaga ccaggacaat ctcctaaatt actgatttac tggtcatcca     300
cccggcacac tggagtccct gatcgcttca caggcagtgg atctgggaca gatttcactc     360
tcaccattag ccatgtgcag tctgaagact tggcagatta tttctgtcaa caatatagta     420
```
gttatcctct gtacacattc ggagggggga ccaagctgga aataaacgg          469

<210> SEQ ID NO 2
<211> LENGTH: 560
<212> TYPE: DNA
<213> ORGANISM: Mus musculus

<400> SEQUENCE: 2
ctaatacgac tcactatagg gcaagcagtg gtatcaacgc agagtacatg gggacctatg    60
atcagtgtcc tctccacagt ctctgaagac actgactcta accatgggat ggagatggat   120 ctttctttc tcctgtcag ggactgcagg tgtccattgc caggttcaac tgcagcagtc    180
tggacctgag ctggtgaagc ctggggcttt agtgaagata tcctgcaagg cctctggtta   240
caccttcgca ggctacgata taaactggct gaaacagagg cctggacagg acttgagtg    300 gattggatgg attttcctg gggatggtag tactgaatac gatgaaaaat tcaagggcaa    360
ggccacactc actgcagaca aatcctccag cacggcctac atgcagctca gcagcctgac    420
ttctgagaac tctgcagtct atttctgtgc ggtgggatcc tacggtagtg cgcgttcttt   480
tgtttactgg ggccaaggga ctctggtcac tgtctctgca gccaaaacga cacccccatc   540
tgtctatcca ctggcccctg                                                560

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
ttccaggttc cactggtgac                                                 20

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
gcggccgctt cgggtgctgg gcac                                            24

<210> SEQ ID NO 5
<211> LENGTH: 1592
<212> TYPE: DNA
<213> ORGANISM: Artificial Sequence
<220> FEATURE:
<223> OTHER INFORMATION: bispecific T-cell engager with single-chain
      antibody recognition domains for PD-L1 and mouse CD3

<400> SEQUENCE: 5
ccttaggcgc gccaccatgg agacagacac actcctgcta tgggtactgc tgctctgggt    60
tccaggttcc actggtgacg acatccaaat gacccagagt ccatctagtc tgtctgcttc   120
ggtaggtgat agggtcacta ttacttgcag ggcctcccag gacgtgtcaa ctgcagtggc   180
ttggtaccaa cagaagcccg ggaaagctcc caaactgctg atctactccg ccagctttct   240
gtattccgga gttccgtcta gattttccgg atcaggaagc ggcacggatt tcacactcac    300
aataagcagc ctacaaccag aggacttcgc aacctactat tgtcaacagt acctgtacca   360
tccagccacc tttgggcagg gcaccaaggt ggaaatcaag cgcggtggtg gtggatcagg   420

-continued

```
tggaggcgga agtggaggtg gcggatccga agttcagctt gtcgagtccg gtggcggcct    480
ggttcagcct ggtgggtctt tgcgtctgtc atgcgccgcc tctggtttca ccttttcaga    540
ctcttggatc cactgggtga cacaggcccc aggaaagggt cttgagtggg ttgcatggat    600
tagcccctac ggcggcagta catattacgc ggatagcgtg aaagggaggt ttaccatcag    660
cgcagacacg tcgaagaaca ccgcatacct ccagatgaat ccctccgag  ccgaagatac    720
cgccgtgtac tattgtgctc gccggcattg gcctggcggc ttcgattatt ggggacaggg    780
aactctagta acagtgtcgg ccctcagcag cggcggcggc ggcagcgagg tgcagctggt    840
ggagtctggg ggaggcttgg tgcagcctgg aaagtccctg aaactctcct gtgaggcctc    900
tggattcacc ttcagcggct atggcatgca ctgggtccgc caggctccag ggaggggggct    960
ggagtcggtc gcatacatta ctagtagtag tattaatatc aaatatgctg acgctgtgaa   1020
aggccggttc accgtctcca gagacaatgc caagaactta ctgtttctac aaatgaacat   1080
tctcaagtct gaggacacag ccatgtacta ctgtgcaaga ttcgactggg acaaaaatta   1140
ctggggccaa ggaaccatgg tcaccgtctc cagcgccggc ggcggcggca gcggcggcgg   1200
cggcagcggc ggcggcggca gcgacatcca gatgacccag tctccatcat cactgcctgc   1260
ctccctggga cacagagtca ctatcaattg tcaggccagt caggacatta gcaattattt   1320
aaactggtac cagcagaaac cagggaaagc tcctaagctc ctgatctatt atacaaataa   1380
attggcagat ggagtcccat caaggttcag tggcagtggt tctgggagag attcttcttt   1440
cactatcagc agcctggaat ccgaagatat tggatcttat tactgtcaac agtattataa   1500
ctatccgtgg acgttcggac ctggcaccaa gctggaaatc aaacggagca gcagcagaa    1560
gctgatcagc gaggaggacc tgtagcctga gg                                 1592
```

<210> SEQ ID NO 6
<211> LENGTH: 522
<212> TYPE: PRT
<213> ORGANISM: Artificial Sequence
<220> FEATURE:
<223> OTHER INFORMATION: bispecific T-cell engager with single-chain
    antibody recognition domains for PD-L1 and mouse CD3

<400> SEQUENCE: 6

Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Val Ser Thr Ala Val Ala Trp Tyr Gln Gln Lys Pro Gly Lys Ala
    50                  55                  60

Pro Lys Leu Leu Ile Tyr Ser Ala Ser Phe Leu Tyr Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Tyr
            100                 105                 110

Leu Tyr His Pro Ala Thr Phe Gly Gln Gly Thr Lys Val Glu Ile Lys
        115                 120                 125

Arg Gly Gly Gly Gly Ser Gly Gly Gly Ser Gly Gly Gly Gly Ser
    130                 135                 140

Glu Val Gln Leu Val Glu Ser Gly Gly Gly Leu Val Gln Pro Gly Gly

```
145                 150                 155                 160
Ser Leu Arg Leu Ser Cys Ala Ala Ser Gly Phe Thr Phe Ser Asp Ser
                165                 170                 175

Trp Ile His Trp Val Arg Gln Ala Pro Gly Lys Gly Leu Glu Trp Val
                180                 185                 190

Ala Trp Ile Ser Pro Tyr Gly Gly Ser Thr Tyr Tyr Ala Asp Ser Val
                195                 200                 205

Lys Gly Arg Phe Thr Ile Ser Ala Asp Thr Ser Lys Asn Thr Ala Tyr
                210                 215                 220

Leu Gln Met Asn Ser Leu Arg Ala Glu Asp Thr Ala Val Tyr Tyr Cys
225                 230                 235                 240

Ala Arg Arg His Trp Pro Gly Gly Phe Asp Tyr Trp Gly Gln Gly Thr
                245                 250                 255

Leu Val Thr Val Ser Ala Leu Ser Gly Gly Gly Gly Ser Glu Val
                260                 265                 270

Gln Leu Val Glu Ser Gly Gly Gly Leu Val Gln Pro Gly Lys Ser Leu
                275                 280                 285

Lys Leu Ser Cys Glu Ala Ser Gly Phe Thr Phe Ser Gly Tyr Gly Met
                290                 295                 300

His Trp Val Arg Gln Ala Pro Gly Arg Gly Leu Glu Ser Val Ala Tyr
305                 310                 315                 320

Ile Thr Ser Ser Ser Ile Asn Ile Lys Tyr Ala Asp Ala Val Lys Gly
                325                 330                 335

Arg Phe Thr Val Ser Arg Asp Asn Ala Lys Asn Leu Leu Phe Leu Gln
                340                 345                 350

Met Asn Ile Leu Lys Ser Glu Asp Thr Ala Met Tyr Tyr Cys Ala Arg
                355                 360                 365

Phe Asp Trp Asp Lys Asn Tyr Trp Gly Gln Gly Thr Met Val Thr Val
                370                 375                 380

Ser Ser Ala Gly Gly Gly Gly Ser Gly Gly Gly Gly Ser Gly Gly Gly
385                 390                 395                 400

Gly Ser Asp Ile Gln Met Thr Gln Ser Pro Ser Ser Leu Pro Ala Ser
                405                 410                 415

Leu Gly Asp Arg Val Thr Ile Asn Cys Gln Ala Ser Gln Asp Ile Ser
                420                 425                 430

Asn Tyr Leu Asn Trp Tyr Gln Gln Lys Pro Gly Lys Ala Pro Lys Leu
                435                 440                 445

Leu Ile Tyr Tyr Thr Asn Lys Leu Ala Asp Gly Val Pro Ser Arg Phe
450                 455                 460

Ser Gly Ser Gly Ser Gly Arg Asp Ser Ser Phe Thr Ile Ser Ser Leu
465                 470                 475                 480

Glu Ser Glu Asp Ile Gly Ser Tyr Tyr Cys Gln Gln Tyr Tyr Asn Tyr
                485                 490                 495

Pro Trp Thr Phe Gly Pro Gly Thr Lys Leu Glu Ile Lys Arg Ser Ser
                500                 505                 510

Glu Gln Lys Leu Ile Ser Glu Glu Asp Leu
                515                 520

<210> SEQ ID NO 7
<211> LENGTH: 1616
<212> TYPE: DNA
<213> ORGANISM: Artificial Sequence
<220> FEATURE:
<223> OTHER INFORMATION: bispecific T-cell engager with single-chain
      antibody recognition domains for PD-L1 and human CD3
```

<400> SEQUENCE: 7

```
ccttaggcgc gccaccatgg agacagacac actcctgcta tgggtactgc tgctctgggt    60
tccaggttcc actggtgacg acatccaaat gacccagagt ccatctagtc tgtctgcttc   120
ggtaggtgat agggtcacta ttacttgcag ggcctccag gacgtgtcaa ctgcagtggc    180
ttggtaccaa cagaagcccg ggaaagctcc caaactgctg atctactccg ccagctttct   240
gtattccgga gttccgtcta gattttccgg atcaggaagc ggcacggatt tcacactcac   300
aataagcagc ctacaaccag aggacttcgc aacctactat tgtcaacagt acctgtacca   360
tccagccacc tttgggcagg gcaccaaggt ggaaatcaag gcggtggtg gtggatcagg    420
tggaggcgga agtggaggtg gcggatccga agttcagctt gtcgagtccg gtggcggcct   480
ggttcagcct ggtgggtctt tgcgtctgtc atgcgccgcc tctggtttca ccttttcaga   540
ctcttggatc cactgggtga cagggcccc aggaaagggt cttgagtggg ttgcatggat    600
tagcccctac ggcggcagta catattacg ggatagcgtg aaaggaggt ttaccatcag     660
cgcagacacg tcgaagaaca ccgcatacct ccagatgaat tccctccgag ccgaagatac   720
cgccgtgtac tattgtgctc gccggcattg gcctggcggc ttcgattatt ggggacaggg   780
aactctagta acagtgtcgg ccctcagcag cggcggcggc ggcagccagg tgcagctgca   840
gcagagcggc gccgagctgg ccaggcccgg cgccagcgtg aagatgagct gcaaggccag   900
cggctacacc ttcaccaggt acaccatgca ctgggtgaag cagaggcccg ccagggcct    960
ggagtggatc ggctacatca cccccagcag gggctacacc aactacaacc agaagttcaa  1020
ggacaaggcc accctgacca ccgacaagag cagcagcacc gcctacatgc agctgagcag  1080
cctgaccagc gaggacagcg ccgtgtacta ctgcgccagg tactacgacg accactactg  1140
cctggactac tggggccagg gcaccaccct gaccgtgagc agcgccggcg gcggcggcag  1200
cggcggcggc ggcagcggcg gcggcggcag ccagatcgtg ctgacccaga gccccgccat  1260
catgagcgcc agccccggcg agaaggtgac catgacctgc agcgccagca gcagcgtgag  1320
ctacatgaac tggtaccagc agaagagcgg caccagcccc aagagggtgga tctacgacac  1380
cagcaagctg gccagcggcg tgcccgccca cttcagggc agcggcagcg gcaccagcta   1440
cagcctgacc atcagcggca tggaggccga ggacgccgcc acctactact gccagcagtg  1500
gagcagcaac cccttcacct tcggcagcgg caccaagctg gagatcaaca gggccgcac   1560
cgcccccacc agcagcgagc agaagctgat cagcgaggag gacctgtagc ctgagg       1616
```

<210> SEQ ID NO 8
<211> LENGTH: 530
<212> TYPE: PRT
<213> ORGANISM: Artificial Sequence
<220> FEATURE:
<223> OTHER INFORMATION: bispecific T-cell engager with single-chain
      antibody recognition domains for PD-L1 and human CD3

<400> SEQUENCE: 8

```
Met Glu Thr Asp Thr Leu Leu Leu Trp Val Leu Leu Trp Val Pro
1               5                   10                  15

Gly Ser Thr Gly Asp Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Val Ser Thr Ala Val Ala Trp Tyr Gln Gln Lys Pro Gly Lys Ala
    50                  55                  60
```

```
Pro Lys Leu Leu Ile Tyr Ser Ala Ser Phe Leu Tyr Ser Gly Val Pro
 65                  70                  75                  80

Ser Arg Phe Ser Gly Ser Gly Ser Gly Thr Asp Phe Thr Leu Thr Ile
                 85                  90                  95

Ser Ser Leu Gln Pro Glu Asp Phe Ala Thr Tyr Tyr Cys Gln Gln Tyr
                100                 105                 110

Leu Tyr His Pro Ala Thr Phe Gly Gln Gly Thr Lys Val Glu Ile Lys
                115                 120                 125

Arg Gly Gly Gly Ser Gly Gly Gly Gly Ser Gly Gly Gly Gly Ser
130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Thr Phe Ser Asp Ser
                165                 170                 175

Trp Ile His Trp Val Arg Gln Ala Pro Gly Lys Gly Leu Glu Trp Val
                180                 185                 190

Ala Trp Ile Ser Pro Tyr Gly Gly Ser Thr Tyr Tyr Ala Asp Ser Val
                195                 200                 205

Lys Gly Arg Phe Thr Ile Ser Ala Asp Thr Ser Lys Asn Thr Ala Tyr
210                 215                 220

Leu Gln Met Asn Ser Leu Arg Ala Glu Asp Thr Ala Val Tyr Tyr Cys
225                 230                 235                 240

Ala Arg Arg His Trp Pro Gly Gly Phe Asp Tyr Trp Gly Gln Gly Thr
                245                 250                 255

Leu Val Thr Val Ser Ala Leu Ser Gly Gly Gly Gly Ser Gln Val
                260                 265                 270

Gln Leu Gln Gln Ser Gly Ala Glu Leu Ala Arg Pro Gly Ala Ser Val
                275                 280                 285

Lys Met Ser Cys Lys Ala Ser Gly Tyr Thr Phe Thr Arg Tyr Thr Met
                290                 295                 300

His Trp Val Lys Gln Arg Pro Gly Gln Gly Leu Glu Trp Ile Gly Tyr
305                 310                 315                 320

Ile Asn Pro Ser Arg Gly Tyr Thr Asn Tyr Asn Gln Lys Phe Lys Asp
                325                 330                 335

Lys Ala Thr Leu Thr Thr Asp Lys Ser Ser Ser Thr Ala Tyr Met Gln
                340                 345                 350

Leu Ser Ser Leu Thr Ser Glu Asp Ser Ala Val Tyr Tyr Cys Ala Arg
                355                 360                 365

Tyr Tyr Asp Asp His Tyr Cys Leu Asp Tyr Trp Gly Gln Gly Thr Thr
                370                 375                 380

Leu Thr Val Ser Ser Ala Gly Gly Gly Ser Gly Gly Gly Gly Ser
385                 390                 395                 400

Gly Gly Gly Gly Ser Gln Ile Val Leu Thr Gln Ser Pro Ala Ile Met
                405                 410                 415

Ser Ala Ser Pro Gly Glu Lys Val Thr Met Thr Cys Ser Ala Ser Ser
                420                 425                 430

Ser Val Ser Tyr Met Asn Trp Tyr Gln Gln Lys Ser Gly Thr Ser Pro
                435                 440                 445

Lys Arg Trp Ile Tyr Asp Thr Ser Lys Leu Ala Ser Gly Val Pro Ala
                450                 455                 460

His Phe Arg Gly Ser Gly Ser Gly Thr Ser Tyr Ser Leu Thr Ile Ser
465                 470                 475                 480
```

-continued

```
Gly Met Glu Ala Glu Asp Ala Ala Thr Tyr Tyr Cys Gln Gln Trp Ser
                485                 490                 495

Ser Asn Pro Phe Thr Phe Gly Ser Gly Thr Lys Leu Glu Ile Asn Arg
                500                 505                 510

Ala Asp Thr Ala Pro Thr Ser Ser Glu Gln Lys Leu Ile Ser Glu Glu
            515                 520                 525

Asp Leu
    530
```

TARGETING PD-L1 ON TUMOR CELLS

CROSS-REFERENCE TO RELATED APPLICATIONS

This application is a National Stage application under 35 U.S.C. § 371 of International Application No. PCT/US2017/033320, having an International Filing Date of May 18, 2017, which claims the benefit of U.S. Provisional Application Ser. No. 62/338,466, filed on May 18, 2016. The disclosures of the prior applications are considered part of (and are incorporated by reference in their entirety) in the disclosure of this application.

BACKGROUND

1. Technical Field

This document relates to materials and methods for treating cancer. For example, this document provides materials and methods for using PD-L1 targeting domains in bispecific chimeric polypeptides, chimeric transmembrane polypeptides, genetically modified viruses, nucleic acid vectors, and/or fusion-inducing cells to treat cancer.

2. Background Information

Programmed death-ligand 1 ((PD-L1), also known as B7-H1) is frequently expressed on tumor cells and protects them from tumor-reactive T cells by interacting with PD1 on the T cell surface.

SUMMARY

This document provides materials and methods for treating cancer. For example, this document provides materials and methods for treating cancer by administering a bispecific chimeric polypeptide having a PD-L1 targeting domain and an effector domain. This document also provides materials and methods for treating cancer by administering a genetically modified T cell comprising a chimeric transmembrane polypeptide, which chimeric transmembrane polypeptide includes a PD-L1 targeting domain and an intracellular costimulatory signaling domain. This document also provides materials and methods for treating cancer by administering a fusion-inducing cell, which fusion-inducing cell includes a polypeptide comprising a PD-L1 targeting domain. This document also provides materials and methods for treating cancer by administering a nucleic acid vector that can transfect, transduce, or transform, a target host cell to generate a fusion-inducing cell, which nucleic acid vector includes a nucleic acid sequence encoding polypeptide comprising a PD-L1 targeting domain. This document also provides materials and methods for treating cancer by administering a genetically modified virus that expresses a polypeptide comprising a PD-L1 targeting domain on its surface. In some cases, a PD-L1 targeting domain to be used with (a) a bispecific chimeric polypeptide, (b) a genetically modified T cell, (c) administering a fusion-inducing cell, (d) a nucleic acid vector or one or more nucleic acid vectors encoding a fusogenic polypeptide, a polypeptide including a PD-L1 targeting domain, or both, and/or (e) a genetically modified virus described herein can include an scFv that binds PD-L1.

In one aspect, this document features a method for treating cancer in a mammal. The method comprises, or consists essentially of, administering a bispecific chimeric polypeptide comprising a PD-L1 targeting domain and an effector domain to said mammal under conditions wherein said number of cancer cells within said mammal is reduced. The mammal can be a human. The cancer can be breast cancer, ovarian cancer, osteosarcoma, lung cancer, prostate cancer, liver cancer, pancreatic cancer, brain cancer, central nervous system cancer, colon cancer, rectal cancer, colorectal cancer, cervical cancer, or a melanoma. The PD-L1 targeting domain can be an antibody single-chain variable fragment. The antibody single-chain variable fragment can be an amino acid sequence encoded by a nucleotide sequence having at least 90% identity to said nucleotide sequence of SEQ ID NO:1. The antibody single-chain variable fragment can be an amino acid sequence encoded by said nucleotide sequence of SEQ ID NO:1. The antibody single-chain variable fragment can be an amino acid sequence encoded by a nucleotide sequence having at least 90% identity to said nucleotide sequence of SEQ ID NO:2. The antibody single-chain variable fragment can be an amino acid sequence encoded by said nucleotide sequence of SEQ ID NO:2. The effector domain can be an antibody single-chain variable fragment that binds a CD3 polypeptide. The chimeric polypeptide can be an amino acid sequence at least 95% identical to said amino acid sequence of SEQ ID NO:6. The chimeric polypeptide can be said amino acid sequence of SEQ ID NO:6. The chimeric polypeptide can be an amino acid sequence at least 95% identical to said amino acid sequence of SEQ ID NO:8. The chimeric polypeptide can be said amino acid sequence of SEQ ID NO:8.

In another aspect, this document features a method for treating cancer in a mammal comprising, or consisting essentially of, administering a genetically modified T cell comprising a chimeric transmembrane polypeptide under conditions wherein said number of cancer cells within said mammal is reduced, wherein said chimeric transmembrane polypeptide comprises (a) a PD-L1 targeting domain, and (b) an intracellular costimulatory signaling domain. The PD-L1 targeting domain can be an antibody single-chain variable fragment. The antibody single-chain variable fragment can be an amino acid sequence encoded by a nucleotide sequence having at least 90% identity to said nucleotide sequence of SEQ ID NO:1. The antibody single-chain variable fragment can be an amino acid sequence encoded by said nucleotide sequence of SEQ ID NO:1. The antibody single-chain variable fragment can be an amino acid sequence encoded by a nucleotide sequence having at least 90% identity to said nucleotide sequence of SEQ ID NO:2. The antibody single-chain variable fragment can be an amino acid sequence encoded by said nucleotide sequence of SEQ ID NO:2. The intracellular costimulatory signaling domain can be CD28, 4-1BB, or OX40.

In another aspect, this document features a method for treating cancer in a mammal comprising, or consisting essentially of, administering a fusion-inducing cell under conditions wherein said fusion-inducing cell binds to a cancer cell expressing PD-L1 to form a multicellular syncytium, wherein said multicellular syncytium is not viable, and wherein said fusion-inducing cell comprises (a) a fusogenic polypeptide, and (b) a polypeptide comprising a PD-L1 targeting domain capable of binding to said cancer cell expressing PD-L1. The PD-L1 targeting domain can be an antibody single-chain variable fragment. The antibody single-chain variable fragment can be an amino acid sequence encoded by a nucleotide sequence having at least 90% identity to said nucleotide sequence of SEQ ID NO:1. The antibody single-chain variable fragment can be an amino acid sequence encoded by said nucleotide sequence of SEQ ID NO:1. The antibody single-chain variable fragment can be an amino acid sequence encoded by a nucleotide sequence having at least 90% identity to said nucleotide sequence of SEQ ID NO:2. The antibody single-chain variable fragment can be an amino acid sequence encoded by said nucleotide sequence of SEQ ID NO:2. The polypeptide comprising a PD-L1 targeting domain can further include a hemagglutinin domain. The hemagglutinin domain can be a measles virus H glycoprotein polypeptide, a canine distemper virus H glycoprotein polypeptide, a nipah virus H glycoprotein polypeptide, a rinderpest virus H glycoprotein polypeptide, or a phocine distemper virus H glycoprotein polypeptide. The hemagglutinin domain can be a modified hemagglutinin domain including one or more substitutions, insertions, or deletions, such that said modified hemagglutinin domain exhibits reduced binding to a cellular polypeptide. The cellular polypeptide can be complement regulatory molecule CD46, signaling lymphocyte activation molecule (SLAM), or Nectin-4.

In another aspect, this document features a method for treating cancer in a mammal comprising, or consisting essentially of, administering one or more nucleic acid vectors under conditions wherein said one or more nucleic acid vectors are incorporated into a target host cell to generate a fusion-inducing cell, which fusion-inducing cell binds to a cancer cell expressing PD-L1 to form a multicellular syncytium, wherein said multicellular syncytium is not viable, and wherein said one or more nucleic acid vectors comprise (a) a nucleic acid sequence encoding a fusogenic polypeptide, and (b) a nucleic acid sequence encoding a polypeptide comprising a PD-L1 targeting domain capable of binding to said cancer cell expressing PD-L1. The PD-L1 targeting domain can be an antibody single-chain variable fragment. The antibody single-chain variable fragment can be an amino acid sequence encoded by a nucleotide sequence having at least 90% identity to said nucleotide sequence of SEQ ID NO:1. The antibody single-chain variable fragment can be an amino acid sequence encoded by said nucleotide sequence of SEQ ID NO:1. The antibody single-chain variable fragment can be an amino acid sequence encoded by a nucleotide sequence having at least 90% identity to said nucleotide sequence of SEQ ID NO:2. The antibody single-chain variable fragment can be an amino acid sequence encoded by said nucleotide sequence of SEQ ID NO:2. The polypeptide can be a PD-L1 targeting domain further comprises a hemagglutinin domain. The hemagglutinin domain can be a measles virus H glycoprotein polypeptide, a canine distemper virus H glycoprotein polypeptide, a nipah virus H glycoprotein polypeptide, a rinderpest virus H glycoprotein polypeptide, and a phocine distemper virus H glycoprotein polypeptide. The hemagglutinin domain can be a modified hemagglutinin domain including one or more substitutions, insertions, or deletions, such that said modified hemagglutinin domain exhibits reduced binding to a cellular polypeptide. The cellular polypeptide can be complement regulatory molecule CD46, signaling lymphocyte activation molecule (SLAM), or Nectin-4.

In another aspect, this document features a method for treating cancer in a mammal comprising, or consisting essentially of, administering a genetically modified virus that expresses a polypeptide comprising a PD-L1 targeting domain on its surface under conditions wherein said virus is capable of infecting a cancer cell expressing PD-L1. The PD-L1 targeting domain can be an antibody single-chain variable fragment. The antibody single-chain variable fragment can be an amino acid sequence encoded by a nucleotide sequence having at least 90% identity to said nucleotide sequence of SEQ ID NO:1. The antibody single-chain variable fragment can be an amino acid sequence encoded by said nucleotide sequence of SEQ ID NO:1. The antibody single-chain variable fragment can be an amino acid sequence encoded by a nucleotide sequence having at least 90% identity to said nucleotide sequence of SEQ ID NO:2. The antibody single-chain variable fragment can be an amino acid sequence encoded by said nucleotide sequence of SEQ ID NO:2. The polypeptide can be a PD-L1 targeting domain further comprises a hemagglutinin domain. The hemagglutinin domain can be a measles virus H glycoprotein polypeptide, a canine distemper virus H glycoprotein polypeptide, a nipah virus H glycoprotein polypeptide, a rinderpest virus H glycoprotein polypeptide, and a phocine distemper virus H glycoprotein polypeptide. The hemagglutinin domain can be a modified hemagglutinin domain including one or more substitutions, insertions, or deletions, such that said modified hemagglutinin domain exhibits reduced binding to a cellular polypeptide. The cellular polypeptide can be complement regulatory molecule CD46, signaling lymphocyte activation molecule (SLAM), or Nectin-4.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 5. (A) Consensus nucleic acid sequence of the murine anti-human PD-L1 kappa light chain from hybridoma cell line clone 5H1. (B) Consensus nucleic acid sequence of the murine anti-human PD-L1 kappa heavy chain from hybridoma cell line clone 5H1.

FIG. 6. Characterization of 5H1-scFv-Fc (sa5H1) binding to human PD-L1 expressed on the surface of human cells by flow cytometry. 624mel cells do not express PD-L1. 624mel/B7-H1 cells constitutively express PD-L1. Mel 624 and B7H1/Mel 624 cells were incubated with cleared supernatant from 5H1 hybridoma cells, cleared supernatant from sa5H1 transfected 293 Ts, or with 1 μg of murine IgG isotype control antibody (Pierce, Thermo Scientific). Antibody binding to PD-L1 was detected by flow cytometry using an Alexa Fluor 647 conjugated goat-anti-mIgG (H+L) secondary antibody (Life Technologies). X axes show Alexa Fluor 647 fluorescence intensity. Y axes show cell count.

Figures 19A, 19B:
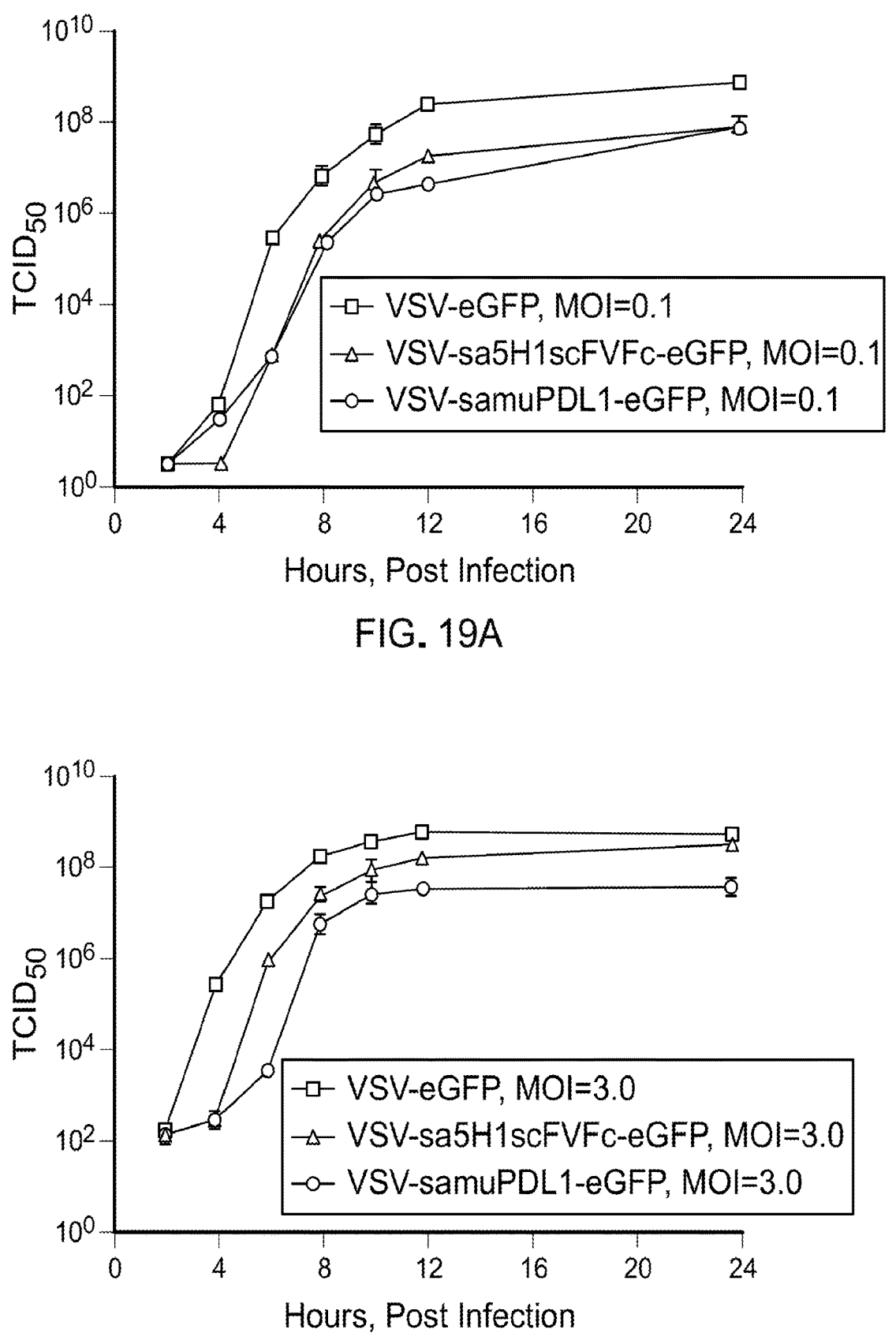

FIG. 19. Infectious titer of VSV encoding sa5H1 antibody. BHK cells were infected with VSV encoding eGFP only (VSV-eGFP), eGFP and sa5H1 antibody (VSV-sa5H1-eGFP), or eGFP and a single-chain antibody that binds human and mouse PD-L1 (VSV-samuPDL1-eGFP) at an multiplicity of infection of 0.1 (A) or 3 (B). Samples were collected at 2, 4, 6, 8, 10, 12, and 24 hours post-infection. Viral titers (TCID50/mL) in each sample were determined in Vero cells, and growth kinetics were compared. Data is represented as mean viral titer+/−standard deviation. X axes show time post-infection. Y axes show virus titer in TCID50 per ml FIG. 20. ELISA traces showing that the sa5H1 antibody produced by VSV-sa5H1-eGFP infected BHK cells binds specifically to huPDL1 protein. The X axes show time post-infection, and the Y axes show absorbance at 450 nm. (A) muPD-L1 (His tag). (B) huPD-L1 (hIgG1-Fc tag).

Figures 21A, 21B, 21C:
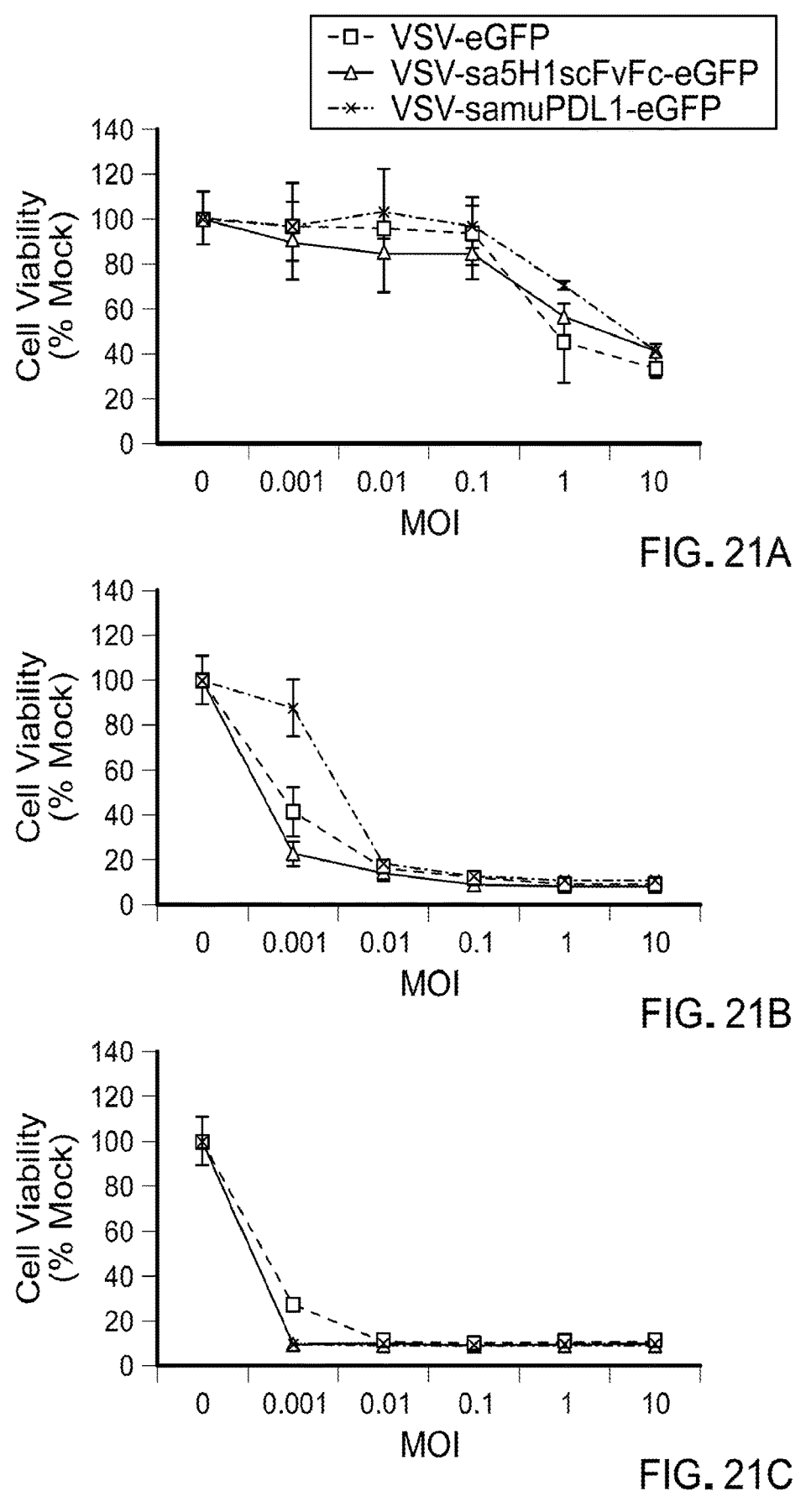

FIG. 21. MTT (3-(4,5-dimethylthiazolyl-2)-2,5-diphenyltetrazolium bromide) assays showing that VSV encoding the sa5H1 antibody maintains cytolytic activity against murine myeloma 5TGM1 cells. The X axes show MOI, and the Y axes show cell viability. (A) Viable cell proliferation at 24 hours post-infection. (B) Viable cell proliferation at 48 hours post-infection. (C) Viable cell proliferation at 72 hours post-infection.

DETAILED DESCRIPTION

Figure 1:
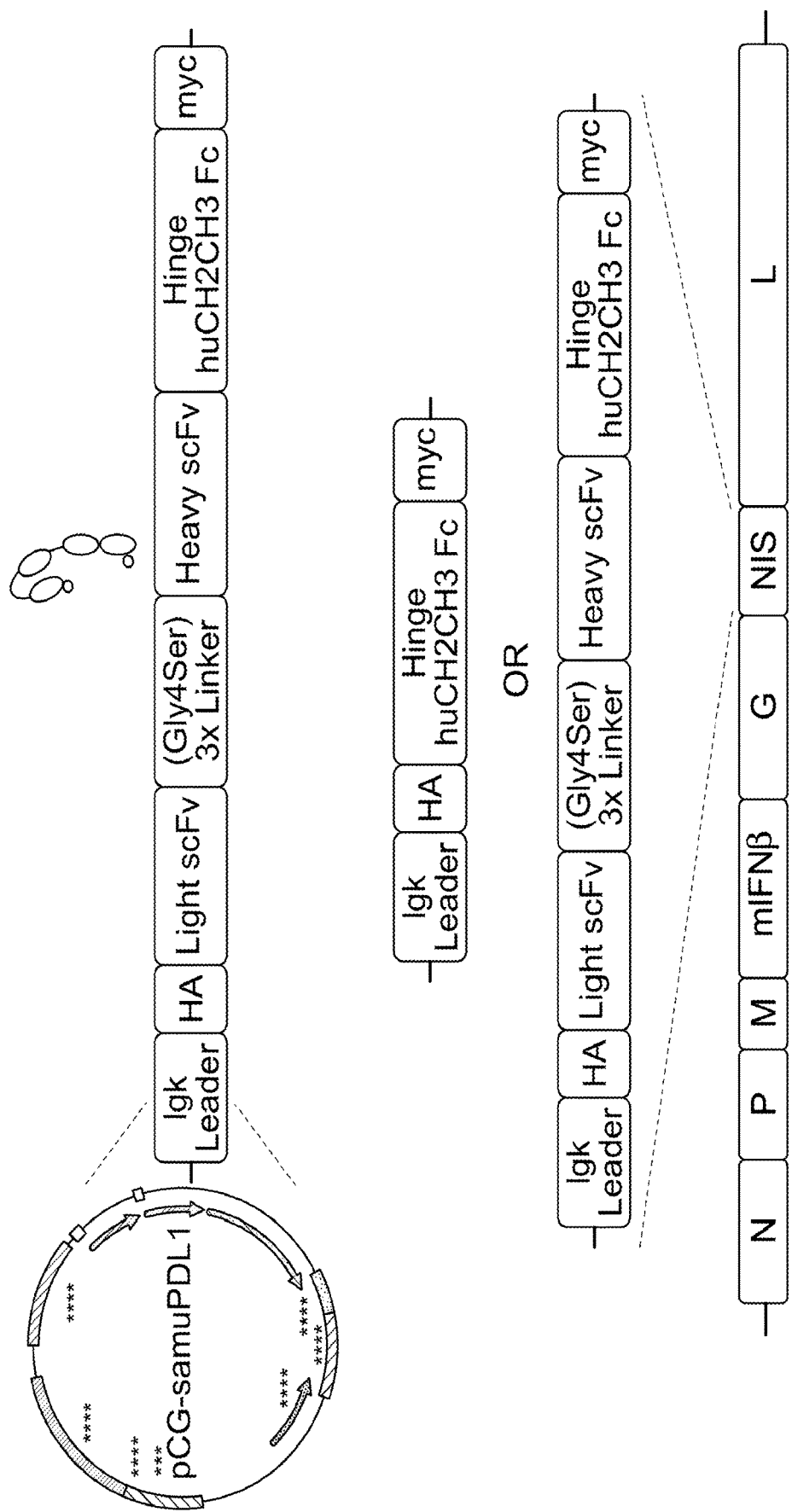
FIG. 1. Schematic representation of the recombinant VSV encoding anti-PD-L1 antibody. M=Matrix; G=Glycoprotein; N=Nucleoprotein; P=Phophoprotein; GFP=Green Fluorescence Protein; L=Polymerase.

This document provides methods and materials for treating cancer. Any appropriate mammal having cancer can be treated using the materials and methods described herein. For example, humans or other primates such as monkeys can be identified as having cancer, and a chimeric polypeptide having a PD-L1 targeting domain and an effector domain can be administered to the human or other primate under conditions wherein the number of cancer cells is reduced. In some cases, dogs, cats, horses, cows, pigs, sheep, mice, and rats can be identified and treated using the materials and methods described herein.

Any appropriate cancer can be treated as described herein. For example, breast cancer, ovarian cancer, osteosarcoma, lung cancer, prostate cancer, liver cancer, pancreatic cancer, brain cancer, central nervous system (CNS) cancer, colon cancer, rectal cancer, colorectal cancer, cervical cancer, or a melanoma can be identified in a mammal and can be treated by administering (a) a bispecific chimeric polypeptide including a PD-L1 targeting domain and an effector domain, (b) genetically modified T cell having a chimeric transmembrane polypeptide, (c) a fusion-inducing cell having both a fusogenic polypeptide and a polypeptide including a PD-L1 targeting domain, and/or (d) a genetically modified virus that express a PD-L1 targeting domain on its surface as described herein.

In some cases, the PD-L1 targeting domain of a chimeric polypeptide used in accordance with materials and methods described herein can include an antibody single-chain variable fragment ("scFv"). An antibody scFv is a fusion of the variable regions of the light chain ($V_L$) and the heavy chain ($V_H$) of an immunoglobulin, covalently joined by a peptide linker. The peptide linker is typically flexible, which can allow the $V_H$-$V_L$ chains to take on the correct structure as a functional monomeric unit, such that the antibody scFv maintains the specificity of the original immunoglobulin from which it is derived.

In some cases, an antibody scFv can include an amino acid sequence encoded by a nucleotide sequence similar to the nucleotide sequence of SEQ ID NO:1, or a fragment of SEQ ID NO:1. For example, an antibody scFv can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:1, or a fragment of SEQ ID NO:1. In some cases, an antibody scFv provided herein can include an amino acid sequence having the CDR1, CDR2, and CDR3 regions encoded by the nucleotide sequence of SEQ ID NO:1. In some cases, an antibody scFv provided herein can include an amino acid sequence encoded by the nucleotide sequence of SEQ ID NO:1, or a fragment of SEQ ID NO:1.

In some cases, an antibody scFv provided herein can include an amino acid sequence encoded by a nucleotide sequence similar to the nucleotide sequence of SEQ ID NO:2, or a fragment of SEQ ID NO:2. For example, an antibody scFv can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:2, or a fragment of SEQ ID NO:2. In some cases, an antibody scFv provided herein can include an amino acid sequence having the CDR1, CDR2, and CDR3 regions encoded by the nucleotide sequence of SEQ ID NO:2. In some cases, an antibody scFv provided herein can include an amino acid sequence encoded by the nucleotide sequence of SEQ ID NO:2, or a fragment of SEQ ID NO:2.

In some cases, an antibody scFv provided herein can bind PD-L1 without blocking the ability of PD-L1 to interact with PD1 (e.g., without blocking the ability of PD-L1 expressing tumor cells to interact with PD1 expressing T cells). In some cases, an antibody scFv provided herein can bind PD-L1 without inhibiting PD-L1 function.

This document provides methods and materials for treating cancer by administering a bispecific chimeric polypeptide having a PD-L1 targeting domain and an effector domain to a mammal under conditions wherein the number of cancer cells within the mammal is reduced. In some cases, a bispecific chimeric polypeptide having a PD-L1 targeting domain and an effector domain can include an amino acid sequence similar to the amino acid sequence of SEQ ID NO:6. For example, a bispecific chimeric polypeptide can include an amino acid sequence that shares at least 80%, 85%, 90%, 91%, 92%, 93%, 94%, 95%, 96%, 97%, 98%, 99%, or more sequence identity to the amino acid sequence of SEQ ID NO:6. In some cases, a bispecific chimeric polypeptide can include the amino acid sequence of SEQ ID NO:6.

In some cases, a bispecific chimeric polypeptide having a PD-L1 targeting domain and an effector domain can include an amino acid sequence encoded by a nucleic acid sequence similar to the nucleic acid sequence of SEQ ID NO:5. For example, a bispecific chimeric polypeptide can include an amino acid sequence encoded by a nucleic acid sequence that shares at least 60%, 70%, 75%, 80%, 85%, 90%, 91%, 92%, 93%, 94%, 95%, 96%, 97%, 98%, 99%, or more sequence identity to the amino acid sequence of SEQ ID NO:5. In some cases, a bispecific chimeric polypeptide can include the amino acid sequence encoded by a nucleic acid sequence of SEQ ID NO:5.

In some cases, a bispecific chimeric polypeptide having a PD-L1 targeting domain and an effector domain can include an amino acid sequence similar to the amino acid sequence of SEQ ID NO:8. For example, a bispecific chimeric polypeptide can include an amino acid sequence that shares at least 80%, 85%, 90%, 91%, 92%, 93%, 94%, 95%, 96%, 97%, 98%, 99%, or more sequence identity to the amino acid sequence of SEQ ID NO:8. In some cases, a bispecific chimeric polypeptide can include the amino acid sequence of SEQ ID NO:8.

In some cases, a bispecific chimeric polypeptide having a PD-L1 targeting domain and an effector domain can include an amino acid sequence encoded by a nucleic acid sequence similar to the nucleic acid sequence of SEQ ID NO:7. For example, a bispecific chimeric polypeptide can include an amino acid sequence encoded by a nucleic acid sequence that shares at least 60%, 70%, 75%, 80%, 85%, 90%, 91%, 92%, 93%, 94%, 95%, 96%, 97%, 98%, 99%, or more sequence identity to the amino acid sequence of SEQ ID NO:7. In some cases, a bispecific chimeric polypeptide can include the amino acid sequence encoded by a nucleic acid sequence of SEQ ID NO:7.

In some cases, a bispecific chimeric polypeptide having a PD-L1 targeting domain and an effector domain can include an amino acid sequence having the CDR1, CDR2, and CDR3 regions encoded by the nucleotide sequence of SEQ ID NO:1. In some cases, a bispecific chimeric polypeptide having a PD-L1 targeting domain and an effector domain can include an amino acid sequence having the CDR1, CDR2, and CDR3 regions encoded by the nucleotide sequence of SEQ ID NO:2.

An effector domain can be of a variety of suitable domains that function to bring a cell that expresses PD-L1, (e.g., a cancer cell that expresses PD-L1) into proximity with a cell capable of mediating destruction of the PD-L1 expressing cell. In some cases, the effector domain of a bispecific chimeric polypeptide can have a PD-L1 targeting domain that includes an antibody scFv that binds to a CD3 polypeptide. In some cases, the effector domain of a bispecific chimeric polypeptide can have a PD-L1 targeting domain that includes an antibody scFv that binds to a Fc polypeptide. For example, a bispecific chimeric polypeptide having a PD-L1 targeting domain and an effector domain, wherein the effector domain includes an antibody scFv that binds a CD3 polypeptide, can be used to bring cells (e.g., cancer cells) expressing PD-L1 in close proximity (e.g., via immunological crosslinking) to a T cell expressing CD3, such that the T cell binds and kills the cell expressing PD-L1. As another example, a bispecific chimeric polypeptide having a PD-L1 targeting domain and an effector domain, wherein the effector domain includes an antibody scFv that binds an Fc polypeptide, can be used to bring cells (e.g., cancer cells) expressing PD-L1 in close proximity (e.g., via immunological crosslinking) to a macrophage expressing Fc, such that the macrophage binds and kills the cell expressing PD-L1. In some cases, bispecific chimeric polypeptides having a PD-L1 targeting domain and any of a variety of other effector domains can be used to bring cells (e.g., cancer cells) expressing PD-L1 in close proximity with T cells, macrophages, or other immune cells that can bind and kill the cell expressing PD-L1.

In some cases, a bispecific chimeric polypeptide having a PD-L1 targeting domain and an effector domain can be used in non-therapeutic applications. For example, a bispecific chimeric polypeptide having a PD-L1 targeting domain and an effector domain can be used to test an agent that modifies the effectiveness of an immune cell (e.g., a T cell or a macrophage) in mediating cell lysis of a PD-L1 expressing cell.

In some cases, a virus (e.g., measles virus or vesicular stomatitis virus) can be modified to express a bispecific chimeric polypeptide having a PD-L1 targeting domain and an effector domain. For example, vesicular stomatitis virus can be engineered to express a bispecific chimeric polypeptide having a PD-L1 targeting domain (e.g., a scFv antibody fragment that binds PD-L1) and an effector domain (e.g., a scFv antibody fragment that binds CD3). In some cases, a virus that has been modified to express a bispecific chimeric polypeptide having a PD-L1 targeting domain and an effector domain can be used to generate a population of bispecific chimeric polypeptides. For example, host cells can be infected with a virus that has been modified to express a bispecific chimeric polypeptide having a PD-L1 targeting domain, such that the host cell secretes the bispecific chimeric polypeptide into a supernatant. Any appropriate method can be used to purify the expressed polypeptides described herein from cellular supernatants.

In some cases, a virus that has been modified to express a bispecific chimeric polypeptide having a PD-L1 targeting domain and an effector domain is introduced into a subject (e.g., a human) that has cancer, such that the bispecific chimeric polypeptide is expressed in the subject and the number of cancer cells in the subject is reduced. In some cases, a virus is modified to express a bispecific chimeric polypeptide having a PD-L1 targeting domain and an effector domain such that the bispecific chimeric polypeptide is released as a discrete molecule in the subject. For example, a nucleic acid molecule encoding the bispecific chimeric polypeptide can be introduced into a viral genome under control of one or more genetic elements that mediate expression of the bispecific chimeric polypeptide in a host cell that has been infected by the virus. When such a genetically modified virus infects a host cell (e.g., via cell fusion or endocytosis), the bispecific chimeric polypeptide is synthesized by the cell and released into the subject.

This document also provides methods and materials for treating cancer by administering a genetically modified T cell having a chimeric transmembrane polypeptide including a PD-L1 targeting domain. For example, this document provides methods and materials for administering a genetically modified T cell having a chimeric transmembrane polypeptide including a PD-L1 targeting domain (e.g., a scFv that binds PD-L1) and an intracellular costimulatory signaling domain under conditions wherein the number of cancer cells within said mammal is reduced. In some cases, a genetically modified T cell can be derived from a T cell obtained from the mammal into which the genetically modified T cell is to be administered. For example, primary human CD8+ T cells can be obtained (e.g., from the blood) and transfected with a nucleic acid encoding a chimeric transmembrane polypeptide including a PD-L1 targeting domain and an intracellular costimulatory signaling domain such that the chimeric transmembrane polypeptide is expressed in the genetically modified T cell. Any appropriate method can be used to introduce nucleic acids into T cells for expression. For example, T cells can be transfected or electroporated with vectors having nucleic acids to be expressed under control of one or more genetic regulatory elements.

A chimeric transmembrane polypeptide can include one or more suitable intracellular costimulatory signaling domains. Examples of intracellular costimulatory signaling domains that can be used as described herein include, without limitation, CD3 zeta chain (CD247), CD28, 4-1BB (CD137), and OX40.

A chimeric transmembrane polypeptide can include any of a variety of suitable transmembrane domains. For example, a chimeric transmembrane polypeptide can have a single-pass or multiple pass transmembrane sequence. In some cases, a chimeric transmembrane polypeptide can have a membrane-targeting sequence that directs the chimeric transmembrane polypeptide to the cell membrane during or after polypeptide synthesis.

In some cases, chimeric transmembrane polypeptides as described herein also can include one or more linker domains (e.g., one or more linker amino acid sequences) between either the PD-L1 targeting domain and the transmembrane domain, and/or between the transmembrane domain and the intracellular costimulatory signaling domain(s). Such linker amino acid sequences generally function to provide flexibility, allowing the PD-L1 targeting domain and the intracellular costimulatory signaling domains(s) to function properly. For example, the hinge region from IgG1 can be used as a flexible linker domain between the PD-L1 targeting domain and the transmembrane domain.

In some cases, a chimeric transmembrane polypeptide provided herein (e.g., for use with a genetically modified T cell having a chimeric transmembrane polypeptide including a PD-L1 targeting domain and an intracellular costimulatory signaling domain) can include an amino acid sequence encoded by a nucleotide sequence similar to the nucleotide sequence of SEQ ID NO:1. For example, a chimeric transmembrane polypeptide can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:1, or a fragment of SEQ ID NO:1. In some cases, a chimeric transmembrane polypeptide provided herein can include an amino acid sequence having the CDR1, CDR2, and CDR3 regions encoded by the nucleotide sequence of SEQ ID NO:1. In some cases, a chimeric transmembrane polypeptide provided herein can include an amino acid sequence encoded by the nucleotide sequence of SEQ ID NO:1, or a fragment of SEQ ID NO:1.

In some cases, a chimeric transmembrane polypeptide provided herein (e.g., for use with a genetically modified T cell having a chimeric transmembrane polypeptide including a PD-L1 targeting domain and an intracellular costimulatory signaling domain) can include an amino acid sequence encoded by a nucleotide sequence similar to the nucleotide sequence of SEQ ID NO:2. For example, a chimeric transmembrane polypeptide can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:2, or a fragment of SEQ ID NO:2. In some cases, a chimeric transmembrane polypeptide provided herein can include an amino acid sequence having the CDR1, CDR2, and CDR3 regions encoded by the nucleotide sequence of SEQ ID NO:2. In some cases, a chimeric transmembrane polypeptide provided herein can include an amino acid sequence encoded by the nucleotide sequence of SEQ ID NO:2, or a fragment of SEQ ID NO:2.

In some cases, a chimeric transmembrane polypeptide as described herein can be introduced into a CD8+ T cell, such that expression of the chimeric transmembrane polypeptide is under control of one or more genetic control elements. Examples of such genetic control elements include, without limitation, promoters and enhancers. In some cases, a genetic control element can be inducible such that expression of the chimeric transmembrane polypeptide is regulated. For example, a chimeric transmembrane polypeptide can be placed under control of a genetic control element that is capable of being activated or repressed by introduction of an agent (e.g., a drug).

This document also provides methods and materials for treating cancer by administering a fusion-inducing cell having a fusogenic polypeptide. For example, this document provides methods and materials for administering a fusion-inducing cell having a fusogenic polypeptide (e.g., a fusogenic membrane glycoprotein) and a polypeptide including a PD-L1 targeting domain capable of binding to a cancer cell expressing PD-L1, under conditions wherein the fusion-inducing cell and cancer cell, when bound, form a multicellular syncytium that is, or becomes, non-viable. The fusion-inducing cell can be derived from any cell capable of expressing a fusogenic polypeptide that is suitable for administration to a mammal (e.g., a human). An example of such a cell includes, without limitation, a 624mel cell. In some cases, a fusion-inducing cell having a fusogenic polypeptide and a polypeptide including a PD-L1 targeting domain can be derived from a cell obtained from the mammal into which the fusion-inducing cell is to be administered.

Any fusogenic polypeptide capable of mediating cell fusion can be used as described herein. An example of such a fusogenic polypeptide includes, without limitation, the measles F protein. In some cases, a fusogenic polypeptide can be a fusogenic glycoprotein. In some cases, a fusogenic polypeptide (e.g., a fusogenic glycoprotein) can mediate cell fusion when it is part of a fusogenic complex (e.g., a fusogenic glycoprotein complex). In some cases, a fusogenic complex can be a fusogenic glycoprotein complex that includes a measles F protein and a measles H protein. In some cases, a fusogenic polypeptide can be selected from the group consisting of type G membrane glycoprotein of rabies virus, type G membrane glycoprotein of Mokola virus, type G membrane glycoprotein of vesicular stomatitis virus, type G membrane glycoprotein of Togaviruses, murine hepatitis virus JHM surface projection protein, porcine respiratory coronavirus spike glycoprotein, porcine respiratory coronavirus membrane glycoprotein, avian infectious bronchitis spike glycoprotein and its precursor, bovine enteric coronavirus spike protein, paramyxovirus SV5 F protein, Measles virus F protein, canine distemper virus F protein, Newcastle disease virus F protein, human parainfluenza virus 3 F protein, simian virus 41 F protein, Sendai virus F protein, human respiratory syncytial virus F protein, Measles virus hemagglutinin, simian virus 41 hemagglutinin neuraminidase proteins, human parainfluenza virus type 3 hemagglutinin neuraminidase, Newcastle disease virus hemagglutinin neuraminidase, human herpesvirus 1 gH, simian varicella virus gH, human herpesvirus gB proteins, bovine herpesvirus gB proteins, cercopithecine herpesvirus gB proteins, Friend murine leukemia virus envelope glycoprotein, Mason Pfizer monkey virus envelope glycoprotein, HIV envelope glycoprotein, influenza virus hemaglutinin, poxvirus membrane glycoproteins, mumps virus hemaglutinin neuraminidase, mumps virus glycoproteins F1 and F2, West Nile virus membrane glycoprotein, herpes simplex virus membrane glycoprotein, Russian Far East encephalitis virus membrane glycoprotein, Venezuelan equine encephalitis virus membrane glycoprotein, varicella virus membrane glycoprotein, and nipah virus membrane glycoprotein. In some cases, truncation of the cytoplasmic domains of a fusogenic polypeptide from a retrovirus or herpesvirus (such as, without limitation, a fusogenic glycoprotein from gibbon ape leukemia virus (GALV), human immunodeficiency virus (HIV), murine leukemia virus (MLV), etc.) can increase their fusion activity, sometimes with a simultaneous reduction in the efficiency with which they are incorporated into virions (see e.g., Rein et al., 1994, J. Virol. 68: 1773; Brody et al., 1994 J. Virol. 68: 4620; Mulligan et al., 1992, J. Virol. 66: 3971; Pique et al., 1993, J. Virol. 67: 557, Baghian et al., 1993, J. Virol. 67: 2396; and Gage et al., 1993, J. Virol. 67: 219, each of which is incorporated herein by reference in its entirety).

In some cases, administration of a fusion-inducing cell having a fusogenic polypeptide and a PD-L1 targeting domain to a mammal (e.g., a human) can result in the fusion-inducing cell binding one or more PD-L1 expressing cells. In some cases, upon binding, the cells fuse to form a multicellular syncytium, which multicellular syncytium is, or becomes, non-viable. In some cases, non-viability of such a multicellular syncytium can be mediated via apoptosis, attack by a host's immune system, or any other physiological phenomenon that results in death or inactivation of the multicellular syncytium.

In some cases, a fusion-inducing cell can include two or more PD-L1 targeting domains. For example, a fusion-inducing cell can include 2, 3, 4, 5, 6, 7, 8, 9, 10, or more PD-L1 targeting domains. In some cases, the two or more PD-L1 targeting domains can be identical. In some cases, the two or more PD-L1 targeting domains can be different.

In some cases, a fusion-inducing cell can have a PD-L1 targeting domain including an antibody scFv. In some cases, an antibody scFv of a fusion-inducing cell can include an amino acid sequence encoded by a nucleotide sequence similar to the nucleotide sequence of SEQ ID NO:1. For example, an antibody scFv of a fusion-inducing cell can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:1, or a fragment of SEQ ID NO:1. In some cases, an antibody scFv of a fusion-inducing cell can include an amino acid sequence having the CDR1, CDR2, and CDR3 regions encoded by the nucleotide sequence of SEQ ID NO:1. In some cases, an antibody scFv of a fusion-inducing cell can include an amino acid sequence encoded by the nucleotide sequence of SEQ ID NO:1, or a fragment of SEQ ID NO:1.

In some cases, an antibody scFv of a fusion-inducing cell can include an amino acid sequence encoded by a nucleotide sequence similar to the nucleotide sequence of SEQ ID NO:2. For example, an antibody scFv of a fusion-inducing cell can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:2, or a fragment of SEQ ID NO:2. In some cases, an antibody scFv of a fusion-inducing cell can include an amino acid sequence having the CDR1, CDR2, and CDR3 regions encoded by the nucleotide sequence of SEQ ID NO:2. In some cases, an antibody scFv of a fusion-inducing cell can include an amino acid sequence encoded by the nucleotide sequence of SEQ ID NO:2, or a fragment of SEQ ID NO:2.

In some cases, a fusion-inducing cell can have a hemagglutinin fusion polypeptide that includes an antibody scFv that binds PD-L1 (e.g., any antibody scFv that targets PD-L1 described herein) and a hemagglutinin polypeptide. Examples of hemagglutinin polypeptides that can be used as described herein include, without limitation, a measles virus H glycoprotein polypeptide, a canine distemper virus H glycoprotein polypeptide, a nipah virus H glycoprotein polypeptide, a rinderpest virus H glycoprotein polypeptide, and a phocine distemper virus H glycoprotein polypeptide. In some cases, a hemagglutinin fusion polypeptide can include an antibody scFv that binds PD-L1, which antibody scFv is fused to the C-terminus of a hemagglutinin polypeptide. In some cases, a hemagglutinin fusion polypeptide can include an antibody scFv that binds PD-L1, which antibody scFv is fused to the N-terminus of a hemagglutinin polypeptide. In some cases, a hemagglutinin fusion polypeptide can include a polypeptide linker domain between an antibody scFv and a hemagglutinin polypeptide.

In some cases, a fusion-inducing cell can have a hemagglutinin fusion polypeptide that includes an antibody scFv that binds PD-L1 and a hemagglutinin polypeptide, wherein the hemagglutinin polypeptide has been modified to decrease or eliminate its interaction with one or more cellular polypeptides. For example, a hemagglutinin polypeptide can be modified to reduce or eliminate its interaction with complement regulatory molecule CD46, the signaling lymphocyte activation molecule (SLAM), or Nectin-4, such that viral fusion and/or entry via interactions with these polypeptides are minimized or eliminated. Modifications that reduce or eliminate interaction of a hemagglutinin polypeptide with one or more cellular polypeptides can include substitutions, insertions, or deletions in a hemagglutinin polypeptide sequence. In some cases, a virus that expresses on its surface a hemagglutinin fusion polypeptide that includes an antibody scFv that binds PD-L1 and a modified hemagglutinin polypeptide that reduces or eliminates interaction with one or more cellular polypeptides (e.g., SLAM) can increase the binding specificity of the virus for cells (e.g., cancer cells) that express PD-L1 on their surfaces.

This document also provides methods and materials for treating cancer by administering a nucleic acid vector to generate a fusion-inducing cell having a fusogenic polypeptide. For example, this document provides methods and materials for administering one or more nucleic acid vectors to a target host cell to generate a fusion-inducing cell having a fusogenic polypeptide (e.g., a fusogenic membrane glycoprotein) and a polypeptide including a PD-L1 targeting domain capable of binding to a cancer cell expressing PD-L1, under conditions wherein the generated fusion-inducing cell and cancer cell, when bound, form a multicellular syncytium that is, or becomes, non-viable.

In some cases, one or more nucleic acid vectors can be administered to a subject to generate a fusion-inducing cell in situ in the subject. For example, one or more nucleic acid vectors can be administered such that a target host cell of the subject is transfected, transduced, or transformed with the nucleic acid vector. A nucleic acid vector as described herein can include nucleic acid sequences encoding a fusogenic polypeptide (e.g., a fusogenic membrane glycoprotein), a polypeptide including a PD-L1 targeting domain, or both. Such fusogenic and PD-L1 targeting domain-containing polypeptides can be under control of one or more genetic control elements (e.g., promoters or enhancers) capable of directing expression in a target host cell. In some cases, once transfected, transduced, or transformed, a target host cell can express nucleic acid sequences encoding the fusogenic polypeptide and the polypeptide including a PD-L1 targeting domain on its surface to become a fusion-inducing cell. In some cases, one or more genetic control elements can be included in the nucleic acid vector(s) to restrict expression of a fusogenic polypeptide, a polypeptide including a PD-L1 targeting domain, or both to the desired target host cell.

Any suitable vector system, viral or nonviral, can be used to deliver a nucleic acid vector to a target host cell. For example, viral vectors that can be used to deliver a nucleic acid vector to a target host cell include, without limitation, retroviral vectors, adenoviral vectors, adeno-associated viral vectors, herpes viral vectors, and Semliki forest viral (alphaviral) vectors. In some cases, a measles virus or a vesicular stomatitis virus can be used to deliver a nucleic acid vector to a target host cell. In some cases, liposomes, hydrogels, cyclodextrins, biodegradable nanocapsules, bioadhesive microspheres, or other non-viral vector system can be used to deliver a nucleic acid vector to a target host cell.

A target host cell that is transfected, transduced, or transformed with one or more nucleic acid vectors as described herein to generate a fusion-inducing cell can be a stationary cell (e.g., a neoplastic cell or stromal element in a solid tumor) or a migratory cell (e.g., a T lymphocyte, a B lymphocyte, or other haemopoietic cell or migratory neoplastic cell in a haematological malignancy). A cell to which a generated fusion-inducing cell fuses can also be stationary or migratory.

In some cases, administration of one or more nucleic acid vectors to a mammal (e.g., a human) to generate a fusion-inducing cell having a fusogenic polypeptide and a PD-L1 targeting domain can result in the generated fusion-inducing cell binding one or more PD-L1 expressing cells (e.g., cancer cells). In some cases, upon binding, the cells fuse to form a multicellular syncytium, which multicellular syncytium is, or becomes, non-viable. In some cases, non-viability of such a multicellular syncytium can be mediated via apoptosis, attack by a host's immune system, or any other physiological phenomenon that results in death or inactivation of the multicellular syncytium.

In some cases, a fusion-inducing cell generated by administering one or more nucleic acid vectors can include a fusogenic polypeptide. Any fusogenic polypeptide capable of mediating cell fusion can be used as described herein. An example of such a fusogenic polypeptide includes, without limitation, the measles F protein. In some cases, a fusogenic polypeptide can be a fusogenic glycoprotein. In some cases, a fusogenic polypeptide (e.g., a fusogenic glycoprotein) can mediate cell fusion when it is part of a fusogenic complex (e.g., a fusogenic glycoprotein complex). In some cases, a fusogenic complex can be a fusogenic glycoprotein complex that includes a measles F protein and a measles H protein. In some cases, a fusogenic polypeptide can be selected from the group consisting of type G membrane glycoprotein of rabies virus, type G membrane glycoprotein of Mokola virus, type G membrane glycoprotein of vesicular stomatitis virus, type G membrane glycoprotein of Togaviruses, murine hepatitis virus JHM surface projection protein, porcine respiratory coronavirus spike glycoprotein, porcine respiratory coronavirus membrane glycoprotein, avian infectious bronchitis spike glycoprotein and its precursor, bovine enteric coronavirus spike protein, paramyxovirus SV5 F protein, Measles virus F protein, canine distemper virus F protein, Newcastle disease virus F protein, human parainfluenza virus 3 F protein, simian virus 41 F protein, Sendai virus F protein, human respiratory syncytial virus F protein, Measles virus hemagglutinin, simian virus 41 hemagglutinin neuraminidase proteins, human parainfluenza virus type 3 hemagglutinin neuraminidase, Newcastle disease virus hemagglutinin neuraminidase, human herpesvirus 1 gH, simian varicella virus gH, human herpesvirus gB proteins, bovine herpesvirus gB proteins, cercopithecine herpesvirus gB proteins, Friend murine leukemia virus envelope glycoprotein, Mason Pfizer monkey virus envelope glycoprotein, HIV envelope glycoprotein, influenza virus hemaglutinin, poxvirus membrane glycoproteins, mumps virus hemaglutinin neuraminidase, mumps virus glycoproteins F1 and F2, West Nile virus membrane glycoprotein, herpes simplex virus membrane glycoprotein, Russian Far East encephalitis virus membrane glycoprotein, Venezuelan equine encephalitis virus membrane glycoproteinand, varicella virus membrane glycoprotein, and nipah virus membrane glycoprotein. In some cases, truncation of the cytoplasmic domains of a fusogenic polypeptide from a retrovirus or herpesvirus (such as, without limitation, a fusogenic glycoprotein from gibbon ape leukemia virus (GALV), human immunodeficiency virus (HIV), murine leukemia virus (MLV), etc.) can increase their fusion activity, sometimes with a simultaneous reduction in the efficiency with which they are incorporated into virions (see e.g., Rein et al., 1994, J. Virol. 68: 1773; Brody et al., 1994 J. Virol. 68: 4620; Mulligan et al., 1992, J. Virol. 66: 3971; Pique et al., 1993, J. Virol. 67: 557, Baghian et al., 1993, J. Virol. 67: 2396; and Gage et al., 1993, J. Virol. 67: 219, each of which is incorporated herein by reference in its entirety).

In some cases, a fusion-inducing cell generated by administering one or more nucleic acid vectors can include two or more PD-L1 targeting domains (e.g., 2, 3, 4, 5, 6, 7, 8, 9, 10, or more PD-L1 targeting domains). In some cases, the two or more PD-L1 targeting domains can be identical. In some cases, the two or more PD-L1 targeting domains can be different.

In some cases, a fusion-inducing cell generated by administering one or more nucleic acid vectors can have a PD-L1 targeting domain including an antibody scFv. In some cases, an antibody scFv of a generated fusion-inducing cell can include an amino acid sequence encoded by a nucleotide sequence similar to the nucleotide sequence of SEQ ID NO:1. For example, an antibody scFv of a generated fusion-inducing cell can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:1, or a fragment of SEQ ID NO:1. In some cases, an antibody scFv of a generated fusion-inducing cell can include an amino acid sequence having the CDR1, CDR2, and CDR3 regions encoded by the nucleotide sequence of SEQ ID NO:1. In some cases, an antibody scFv of a generated fusion-inducing cell can include an amino acid sequence encoded by the nucleotide sequence of SEQ ID NO:1, or a fragment of SEQ ID NO:1.

In some cases, an antibody scFv of a generated fusion-inducing cell can include an amino acid sequence encoded by a nucleotide sequence similar to the nucleotide sequence of SEQ ID NO:2. For example, an antibody scFv of a generated fusion-inducing cell can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:2, or a fragment of SEQ ID NO:2. In some cases, an antibody scFv of a generated fusion-inducing cell can include an amino acid sequence having the CDR1, CDR2, and CDR3 regions encoded by the nucleotide sequence of SEQ ID NO:2. In some cases, an antibody scFv of a generated fusion-inducing cell can include an amino acid sequence encoded by the nucleotide sequence of SEQ ID NO:2, or a fragment of SEQ ID NO:2.

In some cases, a fusion-inducing cell generated by transfecting, transducing, or transforming a target host cell with one or more nucleic acid vectors as described herein can have a hemagglutinin fusion polypeptide that includes an antibody scFv that binds PD-L1 (e.g., any antibody scFv that targets PD-L1 described herein) and a hemagglutinin polypeptide. Examples of hemagglutinin polypeptides that can be used as described herein include, without limitation, a measles virus H glycoprotein polypeptide, a canine distemper virus H glycoprotein polypeptide, a nipah virus H glycoprotein polypeptide, a rinderpest virus H glycoprotein polypeptide, and a phocine distemper virus H glycoprotein polypeptide. In some cases, a hemagglutinin fusion polypeptide can include an antibody scFv that binds PD-L1, which antibody scFv is fused to the C-terminus of a hemagglutinin polypeptide. In some cases, a hemagglutinin fusion polypeptide can include an antibody scFv that binds PD-L1, which antibody scFv is fused to the N-terminus of a hemagglutinin polypeptide. In some cases, a hemagglutinin fusion polypeptide can include a polypeptide linker domain between an antibody scFv and a hemagglutinin polypeptide.

In some cases, a fusion-inducing cell generated by transfecting, transducing, or transforming a target host cell with a nucleic acid vector as described herein can have a hemagglutinin fusion polypeptide that includes an antibody scFv that binds PD-L1 and a hemagglutinin polypeptide, wherein the hemagglutinin polypeptide has been modified to decrease or eliminate its interaction with one or more cellular polypeptides. For example, a hemagglutinin polypeptide can be modified to reduce or eliminate its interaction with complement regulatory molecule CD46, the signaling lymphocyte activation molecule (SLAM), or Nectin-4, such that viral fusion and/or entry via interactions with these polypeptides are minimized or eliminated. Modifications that reduce or eliminate interaction of a hemagglutinin polypeptide with one or more cellular polypeptides can include substitutions, insertions, or deletions in a hemagglutinin polypeptide sequence. In some cases, a virus that expresses on its surface a hemagglutinin fusion polypeptide that includes an antibody scFv that binds PD-L1 and a modified hemagglutinin polypeptide that reduces or eliminates interaction with one or more cellular polypeptides (e.g., SLAM) can increase the binding specificity of the virus for cells (e.g., cancer cells) that express PD-L1 on their surfaces.

This document also provides methods and materials for treating cancer by administering a genetically modified virus that expresses a PD-L1 targeting domain on its surface. For example, this document provides methods and materials for administering a genetically modified virus that expresses a PD-L1 targeting domain on its surface under conditions wherein the virus is capable of binding and mediating destruction of a cancer cell. The virus can be any virus capable of expressing a PD-L1 targeting domain on its surface that is suitable for administration to a mammal (e.g., a human). Examples of such viruses include, without limitation, measles virus and vesicular stomatitis virus.

In some cases, after a genetically modified virus that expresses a PD-L1 targeting domain on its surface binds a PD-L1 expressing cell (e.g., a cancer cell), the virus can enter the cell and mediate cell death. For example, a genetically modified virus that expresses a PD-L1 targeting domain on its surface can enter the cell via endocytosis or fusion with the cell. In some cases, after a genetically modified virus that expresses a PD-L1 targeting domain on its surface binds a PD-L1 expressing cell (e.g., a cancer cell), the virus can inject its genetic material into the cell, which genetic material is capable of mediating cell death.

In some cases, a genetically modified virus that expresses a PD-L1 targeting domain on its surface can include two or more PD-L1 targeting domains. For example, a genetically modified virus can include 2, 3, 4, 5, 6, 7, 8, 9, 10, or more PD-L1 targeting domains. In some cases, the two or more PD-L1 targeting domains can be identical. In some cases, the two or more PD-L1 targeting domains can be different.

In some cases, a genetically modified virus can express on its surface an antibody scFv that binds PD-L1. In some cases, a genetically modified virus can express on its surface an antibody scFv including an amino acid sequence encoded by a nucleotide sequence similar to the nucleotide sequence of SEQ ID NO:1. For example, an antibody scFv of a genetically modified virus can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:1, or a fragment of SEQ ID NO:1. In some cases, a genetically modified virus can express on its surface an antibody scFv including an amino acid sequence having the CDR1, CDR2, and CDR3 regions encoded by the nucleotide sequence of SEQ ID NO:1. In some cases, a genetically modified virus can express on its surface an antibody scFv including an amino acid sequence encoded by the nucleotide sequence of SEQ ID NO:1, or a fragment of SEQ ID NO:1.

In some cases, a genetically modified virus can express on its surface an antibody scFv having an amino acid sequence encoded by a nucleotide sequence similar to the nucleotide sequence of SEQ ID NO:2. For example, an antibody scFv of a genetically modified virus can include an amino acid sequence encoded by a nucleotide sequence that shares at least 60%, 70%, 75%, 80%, 85%, 90%, 91%, 92%, 93%, 94%, 95%, 96%, 97%, 98%, 99%, or more sequence identity to the nucleotide sequence of SEQ ID NO:2, or a fragment of SEQ ID NO:2. In some cases, a genetically modified virus can express on its surface an antibody scFv having an amino acid sequence including the CDR1, CDR2, and CDR3 regions encoded by the nucleotide sequence of SEQ ID NO:2. In some cases, a genetically modified virus can express on its surface an antibody scFv including an amino acid sequence encoded by the nucleotide sequence of SEQ ID NO:2, or a fragment of SEQ ID NO:2.

In some cases, a genetically modified virus that expresses on its surface an antibody scFv that binds PD-L1 can fuse with a cell that expresses PD-L1, such that the virus enters the cell. In some cases, endogenous viral fusion proteins (e.g., the measles F membrane fusion polypeptide) can mediate fusion and viral entry. In some cases, a virus can be modified to express an exogenous polypeptide that mediates fusion and viral entry.

In some cases, a virus (e.g., measles virus or vesicular stomatitis virus) can be genetically modified to express on its surface a hemagglutinin fusion polypeptide that includes an antibody scFv that binds PD-L1 (e.g., any antibody scFv that targets PD-L1 described herein) and a hemagglutinin polypeptide. Examples of hemagglutinin polypeptides that can be used as described herein include, without limitation, a measles virus H glycoprotein polypeptide, a canine distemper virus H glycoprotein polypeptide, a nipah virus H glycoprotein polypeptide, a rinderpest virus H glycoprotein polypeptide, and a phocine distemper virus H glycoprotein polypeptide. In some cases, a hemagglutinin fusion polypeptide can include an antibody scFv that binds PD-L1, which antibody scFv is fused to the C-terminus of a hemagglutinin polypeptide. In some cases, a hemagglutinin fusion polypeptide can include an antibody scFv that binds PD-L1, which antibody scFv is fused to the N-terminus of a hemagglutinin polypeptide. In some cases, a hemagglutinin fusion polypeptide can include a polypeptide linker domain between an antibody scFv and a hemagglutinin polypeptide.

In some cases, a genetically modified virus can express on its surface a hemagglutinin fusion polypeptide that includes an antibody scFv that binds PD-L1 and a hemagglutinin polypeptide, wherein the hemagglutinin polypeptide has been modified to decrease or eliminate its interaction with one or more cellular polypeptides. For example, a hemagglutinin polypeptide can be modified to reduce or eliminate its interaction with complement regulatory molecule CD46, the signaling lymphocyte activation molecule (SLAM), or Nectin-4, such that viral fusion and entry via interactions with these polypeptides are minimized or eliminated. Modifications that reduce or eliminate interaction of a hemagglutinin polypeptide with one or more cellular polypeptides can include substitutions, insertions, or deletions in a hemagglutinin polypeptide sequence. In some cases, a virus that expresses on its surface a hemagglutinin fusion polypeptide that includes an antibody scFv that binds PD-L1 and a modified hemagglutinin polypeptide that reduces or eliminates interaction with one or more cellular polypeptides (e.g., SLAM) can increase the binding specificity of the virus for cells (e.g., cancer cells) that express PD-L1 on their surfaces.

Any appropriate method can be used to identify a mammal having cancer. For example, imaging techniques and biopsy techniques can be used to identify mammals (e.g., humans) having cancer.

Once identified as having cancer cells, the mammal can be administered or instructed to self-administer (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces to reduce the number of cancer cells present within the mammal. In some cases, (a) two or more different (e.g., two, three, four, five, or more different) bispecific chimeric polypeptides including a PD-L1 targeting domain and an effector domain, (b) two or more different (e.g., two, three, four, five, or more different) genetically modified T cells having a chimeric transmembrane polypeptide, (c) two or more different (e.g., two, three, four, five, or more different) fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) two or more different (e.g., two, three, four, five, or more different) genetically modified viruses that express a PD-L1 targeting domain on their surfaces can be administered to a mammal to reduce the number of cancer cells present within the mammal. In some cases, (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be administered in combination to reduce the number of cancer cells present within the mammal.

In some cases, (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be administered to a mammal once or multiple times over a period of time ranging from days to weeks. In some cases, (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be formulated into a pharmaceutically acceptable composition for administration to a mammal having cancer. For example, (a) a therapeutically effective amount of a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces that express a PD-L1 targeting domain on their surfaces can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition containing (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be administered locally or systemically. For example, a composition provided herein can be administered locally by injection into tumors. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be any amount that reduces the number of cancer cells present within the mammal without producing significant toxicity to the mammal. In some cases, effective amounts of (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be administered daily for about 2 to about 4 weeks.

If a particular mammal fails to respond to a particular amount, then the amount of (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be any frequency that reduces the number of cancer cells present within the mammal without producing significant toxicity to the mammal. For example, the frequency of administration can be from about two to about three times a week to about two to about three times a month. The frequency of administration can remain constant or can be variable during the duration of treatment. A course of treatment with a composition containing (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can include rest periods. For example, a composition containing (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering (a) a bispecific chimeric polypeptide or one or more different bispecific chimeric polypeptides including a PD-L1 targeting domain and an effector domain, (b) a genetically modified T cell or one or more genetically modified T cells having a chimeric transmembrane polypeptide, (c) a fusion-inducing cell or one or more fusion-inducing cells having both a fusogenic polypeptide and a polypeptide including a PD-L1 targeting domain, (d) a nucleic acid vector or one or more nucleic acid vectors encoding a fusogenic polypeptide, a polypeptide including a PD-L1 targeting domain, or both, and/or (e) a genetically modified virus or one or more genetically modified viruses that express a PD-L1 targeting domain on their surfaces can be any duration that reduces the number of cancer cells present within the mammal without producing significant toxicity to the mammal. In some cases, the effective duration can vary from several days to several weeks. In general, the effective duration for reducing the number of cancer cells present within the mammal can range in duration from about one week to about four weeks. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment, the number of cancer cells present within a mammal, and/or the severity of one or more symptoms related to the condition being treated (e.g., cancer) can be monitored. Any appropriate method can be used to determine whether or not the number of cancer cells present within a mammal is reduced. For example, imaging techniques and/or molecular assays can be used to assess the number of cancer cells present within a mammal.

The invention will be further described in the following examples, which do not limit the scope of the invention described in the claims.

EXAMPLES

Example 1—Generation of an Anti-PD-L1 Single-Chain Antibody, Derived from a PD-L1 Specific Antibody that does not Block its Interaction with PD1

Oncolytic VSV Encoding Anti-PD-L1 Single-Chain Antibody

Figure 2:
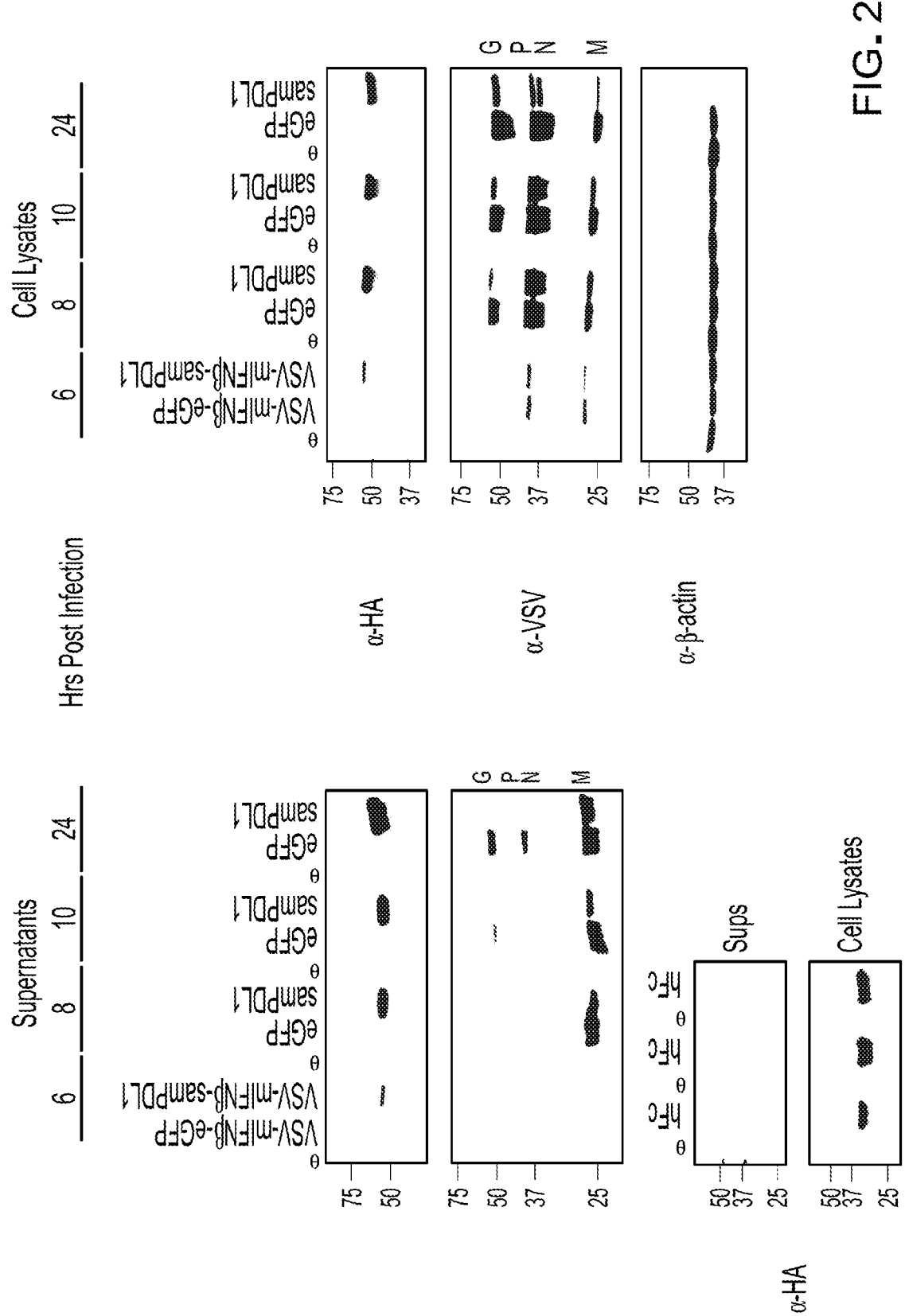
FIG. 2. Protein expression studies to confirm expression of anti-PD-L1 antibody by VSV. BHK cells were infected with VSV encoding mouse interferon β and eGFP (VSV-mIFNβ-eGFP; eGFP), HA-tagged hFc (VSV-mIFNβ-hFc; hFc), or an HA-tagged single-chain antibody that recognizes human and mouse PD-L1 (VSV-mIFNβ-αmPDL1; αmPDL1). Supernatants and cell lysates were collected at 6, 8, 10, and 24 hours post infection, and protein expression was analyzed by Western blot. αHA-HRP (Roche) was used to detected saPD-L1 or sahFc expression. αVSV serum was used to analyze the presence of viral proteins. αβ-actin was used as a loading control.
Figure 3:
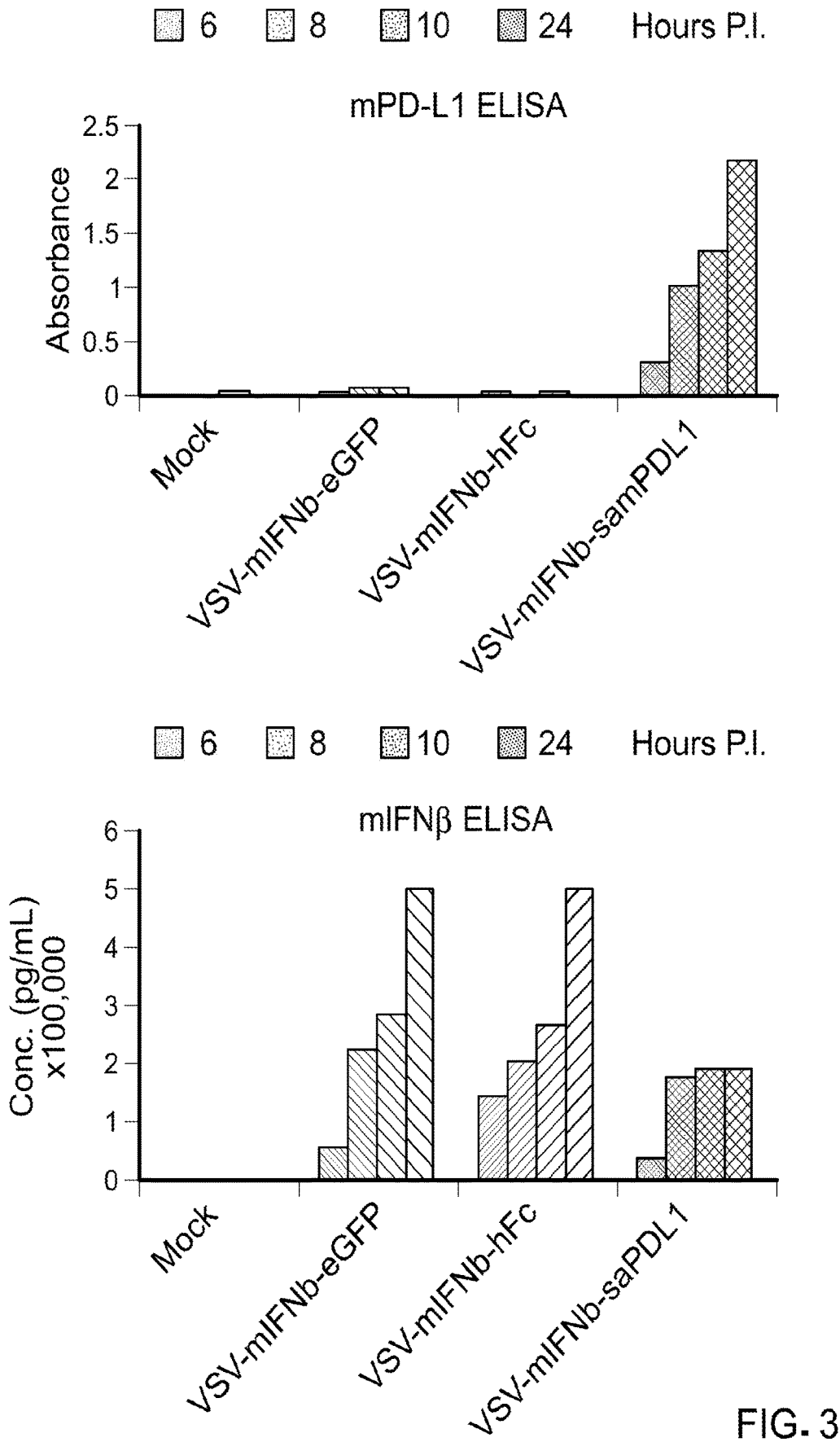
FIG. 3. Characterization of VSV encoding anti-PD-L1 and INFβ. The production of the antibody and murine INFβ was confirmed by a specific ELISA test. The recombinant virus was able to grow with comparable kinetics to the parental virus in a murine myeloma cell line. Left Panels: BHK cells were infected with VSV encoding mouse interferon β and eGFP (VSV-mIFNβ-eGFP; eGFP), HA-tagged hFc (VSV-mIFNβ-hFc; hFc), or a HA-tagged single-chain antibody that recognizes human and mouse PD-L1 (VSV-mIFNβ-αmPDL1; αmPDL1). Supernatants were collected and cleared of cell debris at 6, 8, 10, and 24 hours post infection. Antibody expression and binding to mouse PD-L1 was confirmed by ELISA (upper left panel). Mouse IFNβ expression was quantified (pg/mL) by ELISA (lower left panel). Right Panels: 5TGM1 cells were infected with VSV-mIFNβ-NIS, VSV-mIFNβ-shFc, or VSV-mIFNβ-saPD-L1 at an MOI of 3 (upper right panel) or 0.1 (lower right panel). Samples were collected at 2, 4, 6, 8, 24, and 48 hours post-infection. Viral titers (TCID50/mL) in each sample were determined in Vero cells, and growth kinetics were compared. Data is represented as mean viral titer+/− standard deviation.
Figure 4:
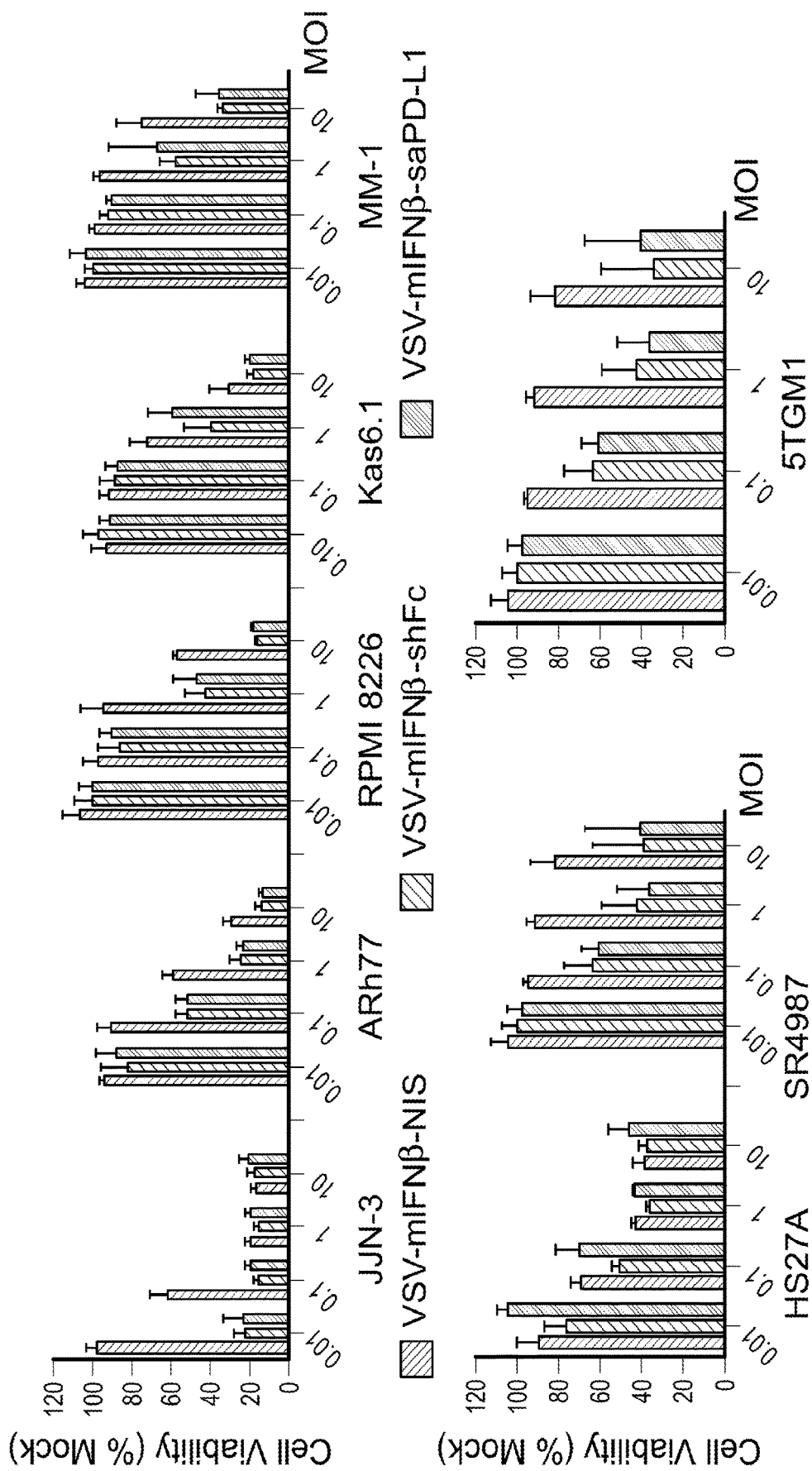
FIG. 4. Recombinant VSV has potent antitumor activity against human and murine myeloma cell lines. Human myeloma cell lines (JJN-3, ARh77, RPMI 8226, Kas6.1, or MM-1), a murine myeloma cell line (5TGM1), a human stromal cell line (HS27A) or a murine stromal cell line (SR4987) were infected at increasing MOI (0.1-10) with VSV-mIFNβ-NIS (black bars), VSV-mIFNβ-shFc (blue bars), or VSV-mIFNβ-saPD-L1 (green bars). For each MOI for each graph, the vertical bars are in groups of three; the order of the bars is VSV-mIFNβ-NIS, VSV-mIFNβ-shFc, and VSV-mIFNβ-saPD-L1. Viable cell proliferation was measured at 48 hours post-infection using the MTT (3-(4, 5-dimethylthiazolyl-2)-2,5-diphenyltetrazolium bromide) assay (ATCC). Data is represented as percent viability compared to mock-infected cells+/−standard deviation.

VSV encoding an HA tagged single-chain anti-PD-L1 human Fc fusion antibody, described elsewhere (Engeland et al., *Mol. Ther.*, 22(11):1949-1959 (2014)), and encoding murine interferon beta (IFNβ) was generated and rescued (FIG. 1). A virus encoding just the human Fc region, as well as IFNβ, was also generated and used as a control. The viruses were used to infect BHK cells. At 6, 8, 10, and 24 hours, supernatants and cells were collected separately. Both the cell lysate and culture supernatant were exposed to immunoblotting to determine the presence of the encoded transgenes. As shown in protein expression studies, the anti-PD-L1 antibody and HA tag can be detected in supernatant and lysates of infected cells, demonstrating that saPD-L1 and the hFc control are properly synthesized in the cell and released into the supernatant following infection (FIG. 2). ELISAs for mouse PD-L1 and IFNβ were performed, and expression of the proteins by the recombinant VSV was confirmed. The viruses were fit, and growth rate was not affected by the encoded transgenes. The viruses were able to grow to comparable titers to the parental virus (FIG. 3). When used to infect a panel of human and murine myeloma cell lines, the virus exhibited dose dependent killing (increasing killing with increasing multiplicity of infection) of the myeloma cells (FIG. 4).

Construction of scFv Based on αPD-L1 Antibody that does not Block PD-1/PD-L1 Interaction The consensus sequences of murine anti-human PD-L1 variable kappa light chain ($V_L$) and heavy chain ($V_H$) regions from hybridoma cell line clone 5H1 (FIG. 5) were determined as follows:
 1. Isolation of total RNA from hybridoma cells
 2. Synthesis of complementary DNA by reverse transcription-PCR (RT-PCR)
 3. PCR amplification of $V_L$ and $V_H$ domains
 4. Sequencing of five to ten individual clones for consensus sequence Following determination of the consensus sequence, overlap extension PCR was used to amplify a signal peptide, the $V_L$, a linker peptide [(Gly$_4$Ser)$_3$], and the $V_H$ from one of the clones to construct a single-chain antibody. The scFv was fused to a murine Fc region via subcloning into a commercially available plasmid (pFUSE-mFc). The 5H1 scFv-Fc antibody ("the sa5H1 antibody") was released from 293T cells following transfection with the plasmid and bound human PD-L1 as determined by ELISA using cleared supernatant. Antibody binding was confirmed by staining human 624mel cells (which do not express PD-L) or 624mel/B7-H1 cells (which constitutively express PD-L) with cleared supernatant and analyzing by flow cytometry (FIG. 6).

Oncolytic VSV Encoding sa5H1

Figure 7:
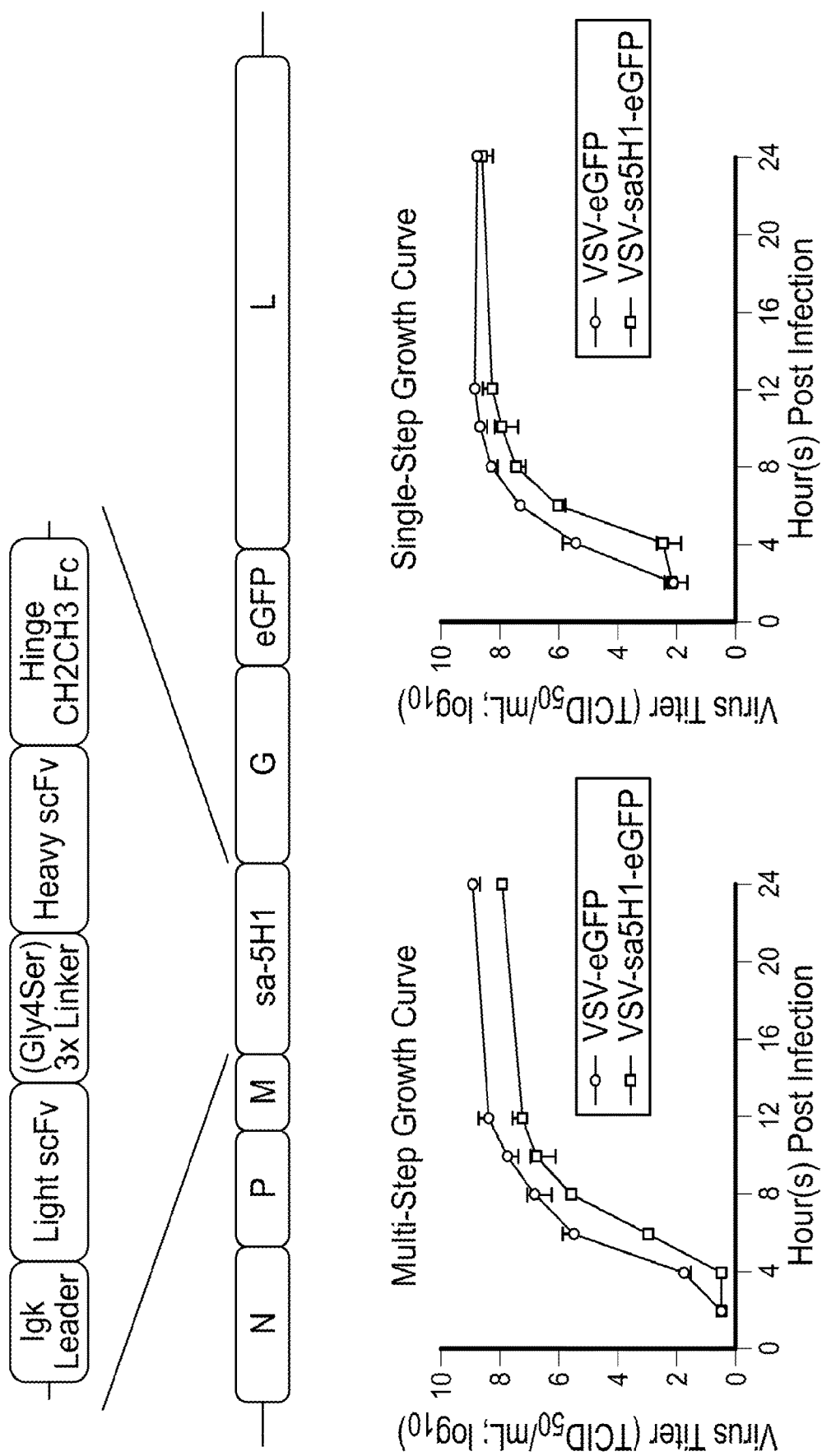
FIG. 7. Schematic representation of recombinant VSV encoding sa5H1 and characterization of virus growth compared to parental virus. The top schematic shows cloning of the sa5H1 construct. M=Matrix; G=Glycoprotein; N=Nucleoprotein; P=Phophoprotein; GFP=Green Fluorescence Protein; L=Polymerase. The bottom panels show growth rates of parent virus encoding enhanced green fluorescent protein (VSV-eGFP) and virus expressing sa5H1-GFP during low (multi-step) or high (single-step) multiplicity of infection.

The sa5H1 antibody was subsequently cloned into VSV encoding enhanced green fluorescent protein (VSV-eGFP) to yield VSV-sa5H1-eGFP. Relatively similar growth kinetics were observed between VSV-eGFP and VSV-sa5H1-eGFP following infection of BHK cells at low (multi-step) or high (single-step) multiplicity of infection (FIG. 7).

Example 2—Generation of a Chimeric Measles
Virus H Glycoprotein Displaying a PD-L1 Specific
scFv as a C-Terminal Fusion Construction of saPD-L1 Targeted MV H Using techniques similar to those described elsewhere (Nakamura et al., *Nat. Biotechnol.*, 22(3):331-336 (2004)), a chimeric measles virus H glycoprotein displaying an anti-PD-L1 scFv was generated. Briefly, an anti-PD-L1 scFv was amplified by PCR from plasmid pCG-samPDL1 (which contains an anti-mouse PD-L1 scFv that also binds to human PD-L1, fused to a human Fc region) using the following primers to remove the HA tag and add a NotI restriction site for subcloning purposes:

```
                             (SEQ ID NO: 3)
Primer Forward:     TTCCAGGTTCCACTGGTGAC (SEQ ID NO: 4)
Primer Reverse:     GCGGCCGCTTCGGGTGCTGGGCAC
```

Figure 8:
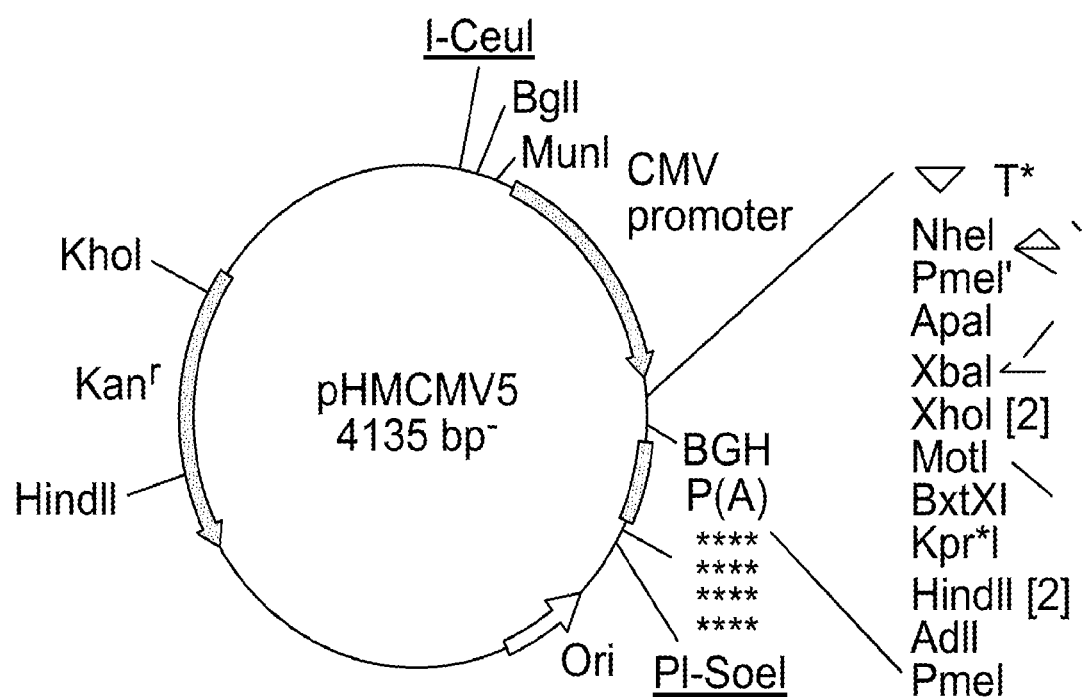
FIG. 8. Map of the pHMCMV5-H plasmid.

The resulting product was cloned into ZeroBlunt Topo. The plasmid was purified, sequenced, and digested with SfiI and NotI. The SfiI-NotI insert was cloned into the pHMCMV5-H plasmid (FIG. 8), in which MV-Haa-αEGFR (MV-H from Edmonston strain with two point mutations to ablate interactions with CD46 and SLAM receptors, bearing a scFv against EGFR) was present after the CMV promoter and before the p(A) sequence. The plasmid was then modified to include two extra mutations to ablate the interactions of MV-H with the cellular protein Nectin-4. The resulting plasmid was pHMCMV5-H4a-αPD-L1.

Characterization of saPD-L1 Targeted MV H

Correct synthesis and processing of the H4a-αPD-L1 glycoprotein is shown using Western blot analysis. 624mel cells are transfected with pHMCMV5-H4a-αPD-L1 plasmid. After 24 hours, the cells are washed with ice-cold PBS and treated with lysis buffer containing protease inhibitors for 15 minutes at 4° C. The lysates are cleared by centrifugation at 4° C. for 15 minutes. The resulting cleared supernatant is mixed with an equal volume of SDS loading buffer, and the proteins fractioned on an SDS-PAGE gel. The proteins are transferred to PVDF membrane, and total H protein is detected by immunoblotting with anti-Flag M2 antibody conjugated to horseradish peroxidase at a 1:2000 dilution and developed with an enhanced chemiluminescence kit. Similar levels of total chimeric H protein compared to unmodified H protein are detected and the presence of the αPD-L1 scFv fusion is observed through a size increase of the protein band. The surface expression level of the H4a-αPD-L1 glycoprotein compared to the parental H protein is determined by flow cytometry. 624mel cells are transfected with pHMCMV5-H4a-αPD-L1 plasmid. At 24 hours post-transfection, the cells are washed with ice-cold PBS and resuspended in ice-cold PBS with 2% FBS at $10^5$ cells/mL. The cells are incubated with a 1:150 dilution of primary mouse monoclonal ascites antibody recognizing the measles H protein (Chemicon) for 60 minutes on ice. The cells are washed with 2% FBS/PBS and incubated for 30 minutes on ice with a 1:150 dilution of FITC-conjugated goat-antimouse IgG. The cells are washed again with 2% PBS/FBS and analyzed by flow cytometry. H4a-αPD-L1 surface expression levels are similar to the parental measles virus H protein.

Targeted Cell Fusion by saPD-L1 Targeted MV H

Targeted cell fusion by the chimeric measles virus H glycoprotein displaying the anti-PD-L1 scFv C-terminal fusion was demonstrated using a replication-deficient adenoviral vector. pHMCMV5-H4a-αPD-L1 was digested with I-CeuI and PI-SceI, and the insert was cloned in between I-CeuI and PI-SceI restriction sites of pAdHM48. This plasmid already contained MV-F cloned in the E3 region. The plasmid was sequenced and used to rescue a replication-deficient Adenovirus (Ad5-H4a-αPD-L1). The virus was concentrated by CsCl gradients, and the total number of physical particles was determined by OD260 absorbance (Table 1).

TABLE 1

| Virus | Passage | Titer |
|---|---|---|
| Ad5-H4a-αmPDL1 | P7 | $1 \times 10^{12}$ particles/ml<br>7.5 μL = CPE of $1.5 \times 10^7$ 293Ad cells in 3 days |

Figure 9:
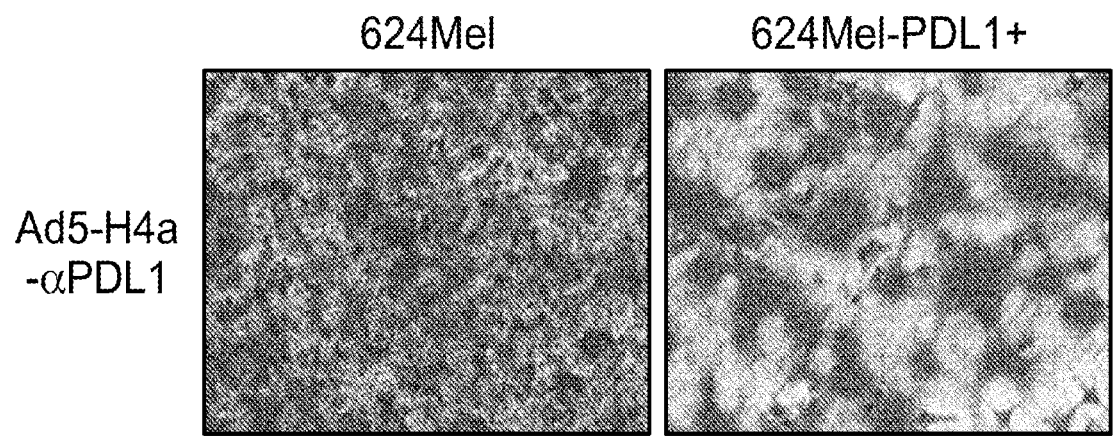
FIG. 9. Fusion of PD-L1 positive cells following infection with replication-deficient adenovirus expressing measles virus F polypeptide and chimeric measles virus H glycoprotein displaying an anti-PDL1 scFv C-terminal fusion. Point mutations were introduced to ablate H glycoprotein binding to normal viral entry receptors.

To determine the specificity of targeted fusion, 624mel cells (which are PD-L1 negative) and 624mel-B7/H1 cells (expressing PD-L1) were infected by Ad5-H4a-αPD-L1. Cells were fixed and stained at 48 hours post infection. Cells fusion was only observed in the PD-L1 positive cells (FIG. 9).

A panel of murine and human tumor cell lines are screened for surface expression of PD-L1 using a commercially available anti-PD-L1 antibody and analyzed using flow cytometry. The panel of cells is infected by Ad5-H4a-αPD-L1. After 48 hours, the cells are fixed and stained, and cell fusion observed. Positive cell fusion is dependent upon the level of PD-L1 surface expression as detected by flow.

In Vivo Characterization of saPD-L1 MV H Fusogenic Membrane Glycoprotein for Anticancer Therapy PD-L1 positive murine tumor cells such as MC38 or PD-L1 negative tumor cells such as 4T1 cells are implanted into syngeneic mice. Established tumors of 0.5 cm mean diameter are treated with four intratumoral injections of Ad-H4a-αPD-L1 at $7 \times 10^9$ viral particles per treatment on days 0, 1, 3, and 4. Control tumors are treated with PBS. Control tumors and PD-L1 negative tumors exhibit continually progressive growth, while PD-L1 positive tumor growth is significantly inhibited. PD-L1 positive human tumor cells such as 624mel/B7-H1 or PD-L1 negative tumor cells such as 624mel human tumor cells are implanted in irradiated athymic nu/nu mice. Established tumors of 0.5 cm mean diameter are treated with four intratumoral injections of Ad-H4a-αPD-L1 at $7 \times 10^9$ viral particles per treatment on days 0, 1, 3, and 4. Control tumors are treated with PBS. Control tumors and PD-L1 negative tumors exhibit continually progressive growth, while PD-L1 positive tumor growth is significantly inhibited.

Example 3—Generation of a Cell Expressing a
Measles F Polypeptide and a Chimeric Measles H
Glycoprotein Including an Anti-PD-L1scFv Fused
to the C-Terminus of the Measles H Glycoprotein,
and the Demonstration that this Cell Selectively
Fuses Tumor Cells Expressing PD-L1

Construction of saPD-L1 MV H Fusogenic Cells and Homologous Cell Fusion

Expression of relevant receptors (CD46, SLAM, Nectin-4, and PD-L1) by human tumor cells such as Jurkat, K562, 624mel and 624mel/B7-H1 is determined by FACs analysis using receptor specific antibodies. Vectors coding for a chimeric measles virus H glycoprotein with a C-terminal α-PD-L1 scFv (H4a-αPD-L) and/or the measles virus F polypeptide are expressed by stably transfecting mammalian cells that do not express PD-L1 such as human 624mel cells or murine 4T1 cells. Coexpression of the H and F polypeptides in the same cell is also achieved by lentiviral transduction. Cells that express high levels of both of the polypeptides are sorted by FACs using measles virus H- and F-specific antibodies and are maintained in culture. These cells are overlayed onto PD-L1 positive cells such as 624mel/B7-H1 cells, and fusion between the two different cells is observed. No fusion is observed when the H/F expressing cells are overlayed onto PD-L1 negative cells such as 624mel cells.

Heterologous Cell Fusion

Heterologous cell fusion mediated by an αPD-L1 retargeted H protein is demonstrated by infecting a cell line lacking any significant expression of PD-L1 such as K562 human erythroleukemic cells (or Jurkat T cells) with adenoviral vectors expressing the measles virus F polypeptide and either an untargeted H glycoprotein or the H4a-αPD-L1 glycoprotein described herein. K562 cells transduced with untargeted H glycoprotein fuse with each other and with cells expressing CD46 such as 624mel and 624mel/B7-H1 cells. K562 cells transduced with αPD-L1 retargeted H glycoprotein do not fuse with each other or with PD-L1 negative cells such as 624mel cells, but do fuse with PD-L1 positive cells such as 624mel/B7-H1 cells.

Example 4—Generation of a Measles Virus Particle Displaying an Anti-PD-L1 scFv as a C-Terminal Fusion with its H-Attachment Protein, and the Demonstration that it Selectively Binds and Enters Tumor Cells Expressing PD-L1

Construction and Characterization of Recombinant Measles Virus Expressing saPD-L1 Targeted H Recombinant H glycoproteins are cloned into the full-length infectious measles virus clone P(+) MVNSe plasmid. Recombinant measles viruses are rescued using a measles virus rescue system using Vero cells stably expressing a membrane-anchored single-chain antibody that recognizes a six-histidine peptide (Vero-His) as described elsewhere (Douglas et al., *Nat. Biotechnol.*, 17(5):470-475 (1999); Nakamura et al., *Nat. Biotechnol.*, 23(2):209-214 (2005)). Conditioned media from infected Vero-HIS cells is harvested and cleared by centrifugation, and virus particles are concentrated and purified through a 20% to 60% sucrose gradient by ultracentrifugation. Viral proteins including the chimeric H glycoprotein are detected by immunoblotting.

The growth characteristics of the recombinant virus and the parental virus are compared following infection of Vero-HIS cells at an MOI of 3 for 2 hours. The cells are washed and maintained at 32° C. to promote viral propagation. At 24, 36, 48, and 72 hours post infection, conditioned media is harvested and cleared of cellular debris by centrifugation. The cells are scraped into fresh media, and the cell-associated virus is released following subjection to two freeze-thaw cycles. The viral titers of the virus are determined by median 50% tissue-culture infectious dose on Vero-HIS cells. Similar growth kinetics are observed between measles virus expressing recombinant α-PD-L1 H glycoproteins and measles viruses expressing unmodified H glycoproteins.

The growth characteristics of the recombinant virus and the parental virus are also compared following infection of 624mel or 624mel/B7-H1 cells at an MOI of 3 for 2 hours. The cells are processed similarly to the Vero-His infection samples described above, and the virus titers determined by $TCID_{50}$ on Vero-His cells. Parental virus propagation in 624mel cells (PD-L1 negative, CD46 positive) is similar to recombinant virus propagation in 624mel/B7-H1 cells (PD-L1 positive). No replication of the parental virus is observed in 624mel/B7-H1 cells, and likewise no propagation of the recombinant virus is observed in 624mel cells as the viruses are unable to bind and enter the cells.

Oncolytic Activity of MV Encoding saPD-L1 Targeted H

The oncolytic activity of an αPD-L1 retargeted measles virus particle is analyzed in mice bearing subcutaneous PD-L1 negative tumors such as 624mel or PD-L1 positive tumors such as 624mel/B7-H1. Mice with established tumor xenografts of 0.5 cm mean diameter are treated systemically with measles virus expressing H4a-αPD-L1. Control mice are treated with UV inactivated virus. All mice with PD-L1 negative tumors or that are treated with UV inactivated virus display progressive tumor growth. Tumor growth is inhibited in virus treated mice bearing PD-L1 positive tumors.

Figure 10:
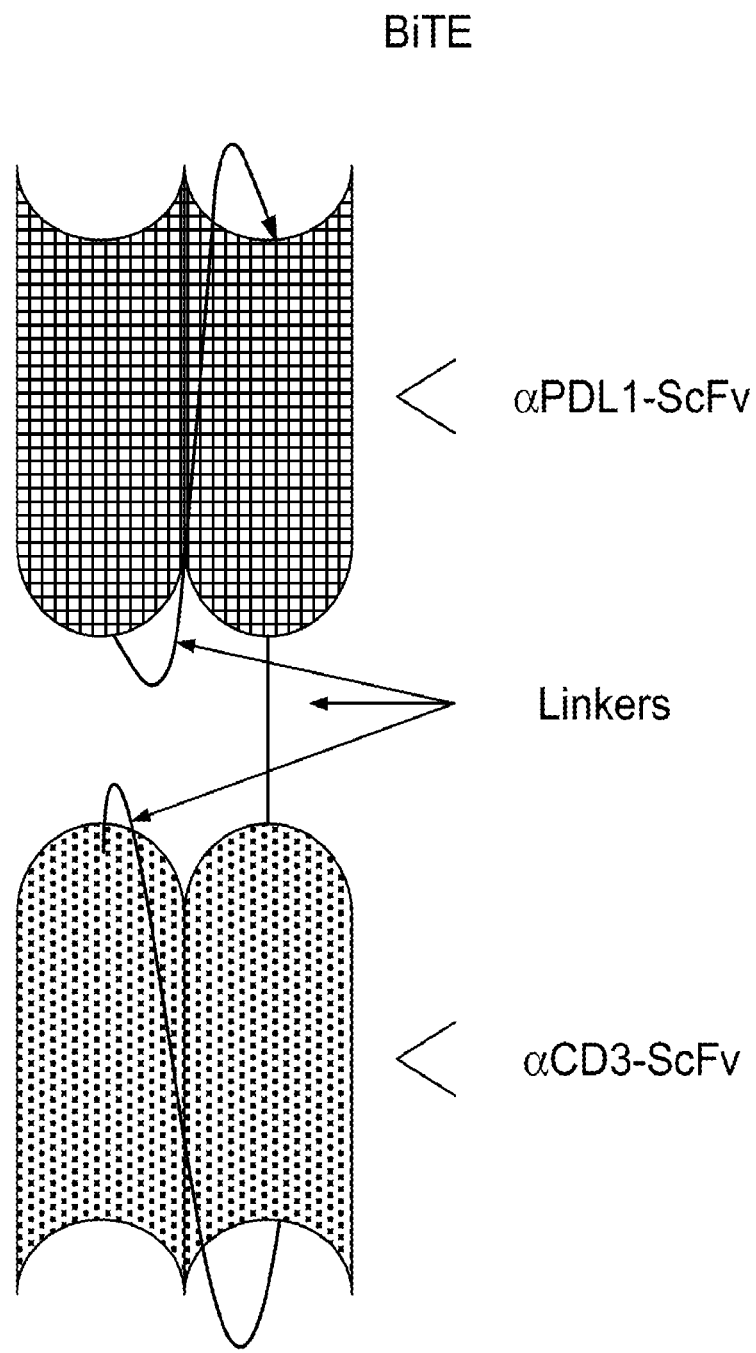
FIG. 10. Construction of a BiTE molecule from two single-chain antibodies. Antibodies were fused via overlapping PCR. $V_L$ and $V_H$ domains are connected through a $(Gly_4Ser)_3$ linker and single-chain antibodies are interconnected through a $Gly_4Ser$ short peptide linker which gives rise to the final BiTE construct.
Figure 11:
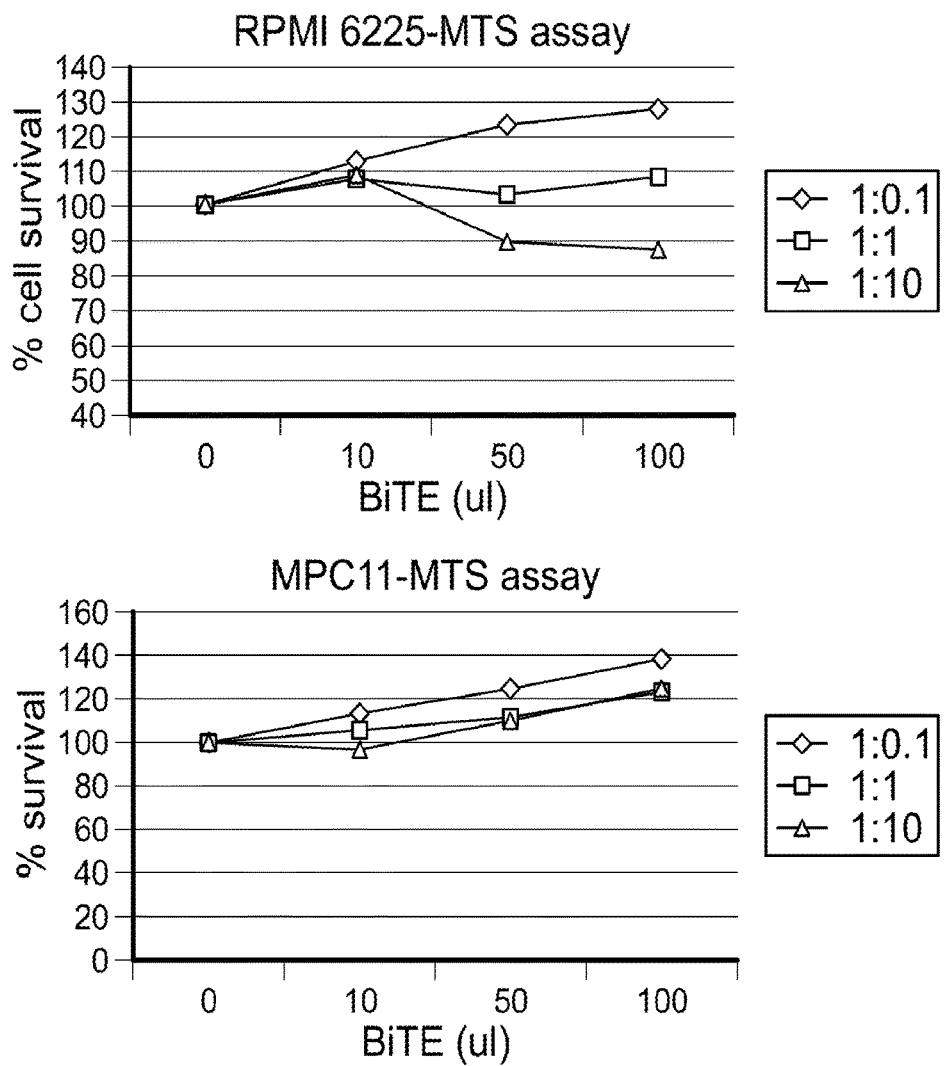
FIG. 11. Lysis of tumor cells by mouse splenocytes expressing BiTE: α-CD38-αmCD3. FRMI 6226 (human myeloma cells are positive for CD38—top panel) and MPC-11 (murine plasmacytoma cells used as a control—bottom panel) cells were mixed with mouse splenocytes at indicated effector:target ratios of 1:0.1, 1:1, and 1:10. The indicated amount of BiTE supernatant was added to the effector target cell mixture. After 48 hours, cell viability was determined by an MTS assay and normalized to control untreated samples.

Example 5—Generation of a Bispecific T Cell Engager Including an Anti-PD-L1 scFv Genetically Fused to a CD-3-Specific scFv which Crosslinks T Cells to PD-L1 Tumor Cells, Causing them to Kill the Tumor Bispecific T cell engager (BiTEs) molecules possess two single-chain antibodies, which are connected through a short flexible linker peptide (FIG. 10). Each single-chain antibody contains two domains ($V_H$-variable heavy and $V_L$-light chain). When BiTE molecules bind to their respective target surface receptors, they can bring the tumor cells and effector T cells to close proximity. This allows the T cells to kill the tumor cells through BiTE mediated cell lysis. This interaction does not require intracellular antigen processing and surface presentation of antigenic peptides, not does it require co-stimulatory molecules.

Figure 12:
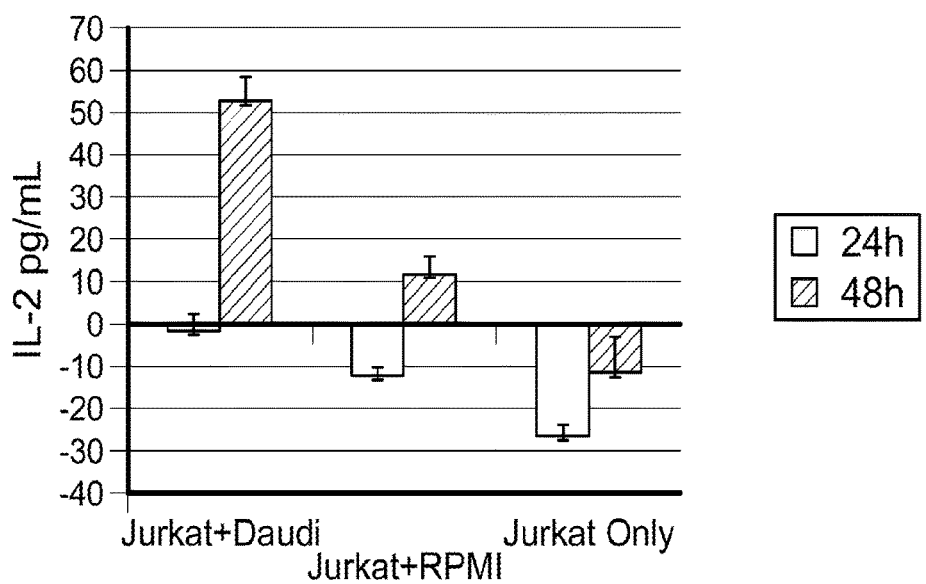
FIG. 12. T cell activation assay. Jurkat cells were mixed with Daudi or RPMI 6225 cells with effector:target ratios of 1:10 along with BiTE antibodies (300 μL). After 48 hours, the supernatants were collected and IL-2 production was determined by ELISA. For each sample, the vertical bars are in groups of two; the order of the bars is 24 hours and 48 hours. P=0.0104 Jurkat+Daudi 24 hours vs. 48 hours. P=0.613 Jurkat+Daudi vs Jurkat+RPMI 6225.

A bispecific single-chain antibody construct that consists of anti-CD38 single-chain antibody was generated and used to demonstrate lysis of tumor cells by mouse splenocytes (BiTE: α-CD38-αmCD3; mice T cell specific, FIG. 12). With its binding property for the CD3ε chain of the T cell receptor (TCR) complex on mouse T cells and human CD38 on tumor cells, it can attract T cells to CD38 positive tumor cells.

The experiment was conducted as follows. Spleens from BALB/c mice were collected according to an approved protocol and crushed through a 100 μm filter to prepare a single-cell suspension. Red blood cells were removed by a 2 minute incubation in ACK buffer (0.15M sodium chloride, 10 mmol/L potassium bicarbonate, 0.1 mmol/L disodium ethylenediaminetetraacetic acid, pH7.2, Diaz et al., Oncolytic Immunovirotherapy for Melanoma Using Vesicular Stomatitis Virus. *Cancer Res.* March 15, 67:2840-2848; doi: 10.1158/0008-5472 (2007)). This splenocyte suspension contained the required T cells for tumor cell lysis assay. RPMI 6225 human myeloma cells, which are positive for CD38, were used as a target tumor cell.

Tumor cells were plated in a 96-well tissue culture plate at $1\times10^3$ cells per well (total volume of 50 μL) and incubated overnight at 37° C. The tumor cells were infected with various amounts of BiTE supernatants. All assay points were done in triplicate. Mouse splenocytes were added to the culture at effector:target ratios of 1:0.1, 1:1, and 1:10. Plates were incubated at 37° C. for 48 hours, and the cell viability was determined using MTS Cell Proliferation Assay (Biovision, CA). The formazan dye produced by viable cells was quantified by measuring the absorbance at 490 nm.

The mean viability of the virus infected tumor cells for each viral dilution was calculated using a percentage relative to the control wells treated with media alone (100% survival)+/−SEM.

At lower concentration, no cell lysis was observed. There was noticeable lysis observed at higher cell target ratio (1:10). MPC-11 murine plasmacytoma cells were used as a control. There was no lysis observed in these cells.

The bispecific single-chain antibody construct that included anti-CD38 single-chain antibody and anti-CD3 single-chain antibody, which is human-specific, was used to demonstrate T cell activation. To test the activity of this human specific BiTE, Jurkat cells were used as effector T cells. Since Jurkat is a permanent cell line, it has lost its cell killing activity. At the same time, it can secrete cytokines such as IL-2 and IFN-γ when it is stimulated. Daudi B cell lymphoma cells, which are positive for CD38 as a target cell, were used.

Briefly, Jurkat T cells and Daudi cells were incubated together (effector:target of 1:10) with BiTE antibodies (300 μL) at 37° C. After 48 hours, the supernatants were collected, and IL-2 production was determined by specific ELISA (PeproTech, NJ) according to the manufacturer's instructions.

Construction of αPD-L1 BiTE and Encoding by Oncolytic VSV

Figure 13C:
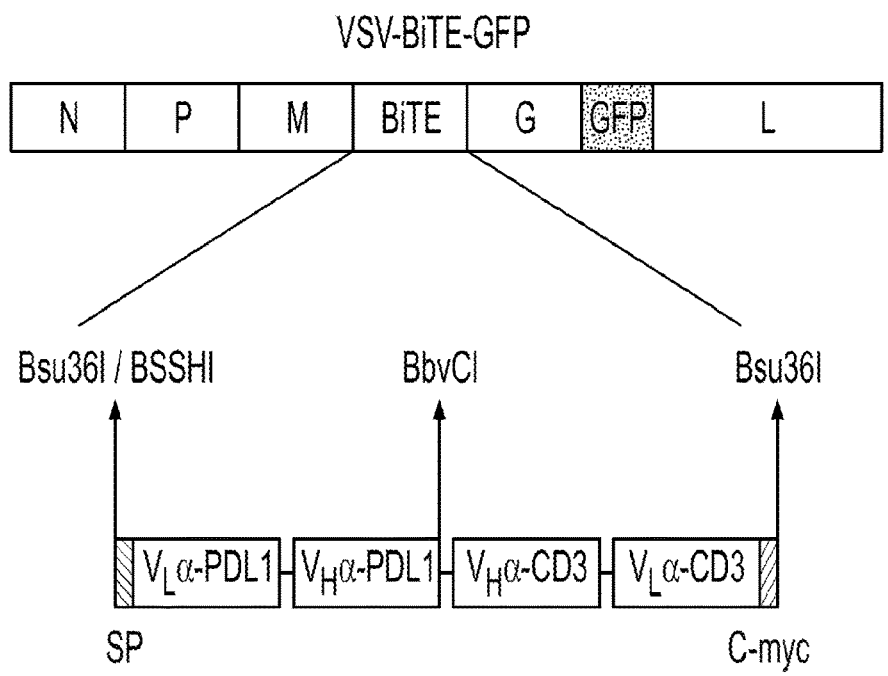
FIG. 13. (A) Nucleotide and polypeptide sequences of mouse BiTE: PDL1-mCD3. (B) Nucleotide and polypeptide sequences of human BiTE: PDL1-mCD3. (C) Construction of a full length VSV vector with BiTE molecule. Both VSV vector and BiTE molecules were digested with the Bsu36I restriction enzyme and ligated. A BbvCI restriction site was created at the end of anti-PD-L1 for future cloning modifications. The BiTE was inserted between the Matrix (M) and Glycoprotein (G) of VSV. N=Nucleoprotein; P=Phophoprotein; GFP=Green Fluorescence Protein; L=Polymerase.

Anti-PD-L1/anti-CD3 BiTE antibodies using mouse (FIG. 13A) and human (FIG. 13B) CD3 sequences and a recombinant VSV expressing the BiTE (FIG. 13C) were constructed as follows. PCR amplification of $V_H$ and $V_L$ domains of anti-PD-L1 single-chain antibody was performed. Fusion of $V_L$ and $V_H$ domain was performed by overlapping PCR. Anti-CD3 $V_L$ and $V_H$ domains were synthesized from Genscript (NJ, USA). The PD-L1 scFv and CD3 scFv were assembled by overlapping PCR. The assembled and amplified BiTE fragment was digested with Bsu36I, and the Bsu36I digested insert was ligated into VSV full length vector (pVSV-GFP). E. coli DH5a cells were transformed with BiTE ligated VSV vector, and bacterial propagation and plasmid purification were performed. Restriction digestion and sequencing analysis of purified VSV plasmids (VSV-BiTE-GFP) was performed.

Figure 14:
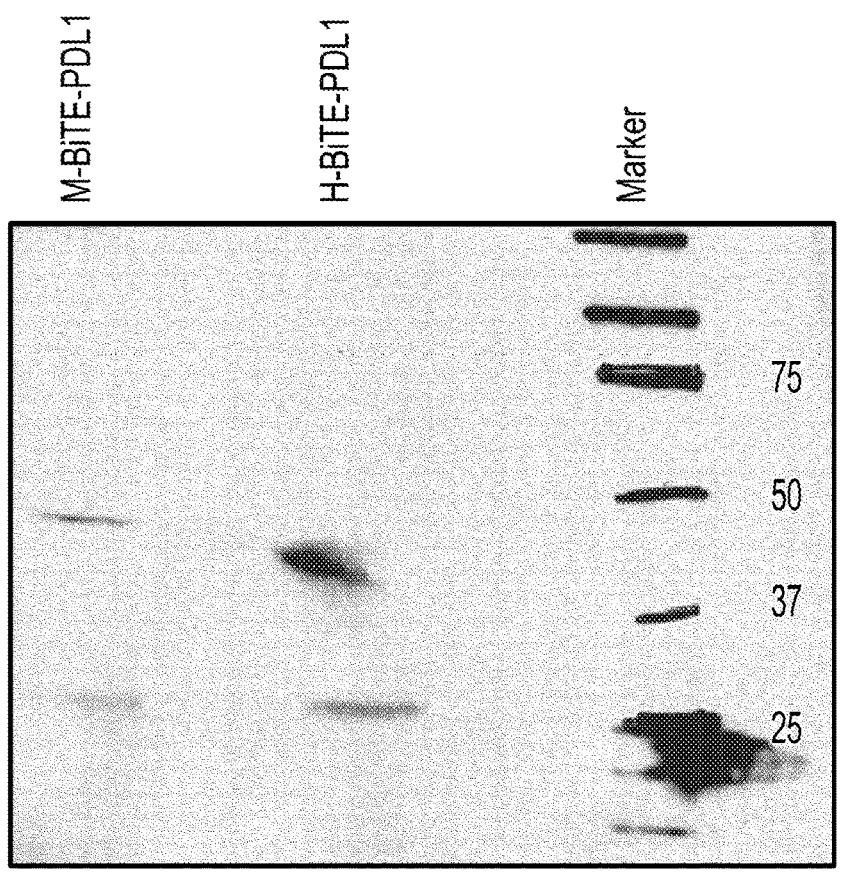
FIG. 14. Immunoblotting of BiTE antibodies. Purified BiTE molecules from supernatants of infected BHK cells were detected using anti-cMyc antibodies.

BiTE molecules were produced as a single polypeptide, which have a molecular weight of approximately 50-60 kDa. Detection of the α-PD-L1/α-CD3 BiTE antibodies (FIG. 14) was conducted as follows. BHK cells were infected with recombinant VSV encoding BiTE and GFP at MOI 1.0. At 24 hours post infection, supernatants were collected, and supernatants were filtered through 0.22 μm filter. VSV was removed by ultracentrifugation (4 hrs) through 10% sucrose cushion. Cleared supernatant was filtered through 0.22 μm filter. Part of supernatant was stored at −80° C., and the remainder was subjected to acetone precipitation. Supernatant was mixed with 4-fold volume of 100% acetone, and incubated at −20° C. overnight. The mixture was centrifuged at 13,000 rpm for 30 minutes to pellet the precipitate. The pellet was then dissolved in SDS gel loading buffer, and subjected to immunoblotting.

αPD-L1 BITE T Cell Activation

The bispecific single-chain antibody construct including anti-human PD-L1 and anti-human CD3 were incubated with Jurkat T cells and either 624mel or 624mel/B7-H1 cells to demonstrate specific T cell activation by interaction with PD-L1. 300 μL of purified BiTE antibody was incubated with Jurkat effector T cells and either of the target cells at an effector:target ratio of 1:10. Jurkat T cells incubated with media only were used as a control. After 48 hours, IL-2 and IFN-γ levels were significantly elevated in the 624mel/B7-H1 cells due to specific interaction of the BiTE with the PD-L1 molecule on the surface of the cells and the CD3 molecule on the Jurkat T cells. No significant elevation of IL-2 or IFN-γ was observed in the 624mel samples compared to media only controls as there was no BiTE mediated stimulation of the Jurkat cells.

αPD-L1 BiTE Mediated Lysis of Tumor Cells

To demonstrate BiTE mediated lysis of tumor cells, splenocytes are collected from a mouse using an approved protocol, and a single-cell suspension generated. MC38 cells, which are known to express high levels PD-L1, or 4T1 cells, which do not express PD-L1, are incubated with the splenocytes at an effector:target (splenocyte:tumor) ratio of 1:10 and increasing amounts of BiTE supernatant. The bispecific single-chain antibody construct that includes an anti-mouse PD-L1 antibody fragment and an anti-mouse CD3 antibody fragment brings the CD3+ murine T cells into close proximity with the PD-L1 positive MC38 tumor cells, but not the PD-L1 negative 4T1 cells. Decreased survival of MC38 cells is observed with increasing amounts of BiTE, while similar survival percentages are maintained by 4T1 cells.

Example 6—Generation of a Chimeric TCR Having a PD-L1 Specific scFv Genetically Fused to a Transmembrane Domain which is in Turn Fused to an Intracellular Domain Including the Costimulatory Signaling Domains of CD28, CD137 (41BB) and the CD3 Zeta Chain (CD247)

Constructing a Chimeric Antigen Receptor (CAR) Specific for PD-L1

A construct expressing a CAR specific for PD-L1 was generated as follows. Plasmid pKT2 expressing a chimeric antigen receptor under the control of a PGK promoter was obtained. The existing scFv was replaced with the scFv against PD-L1 described herein by PCR amplification and cloning between the AfeI-NotI restriction sites of the pKT2 plasmid.

Figure 15:
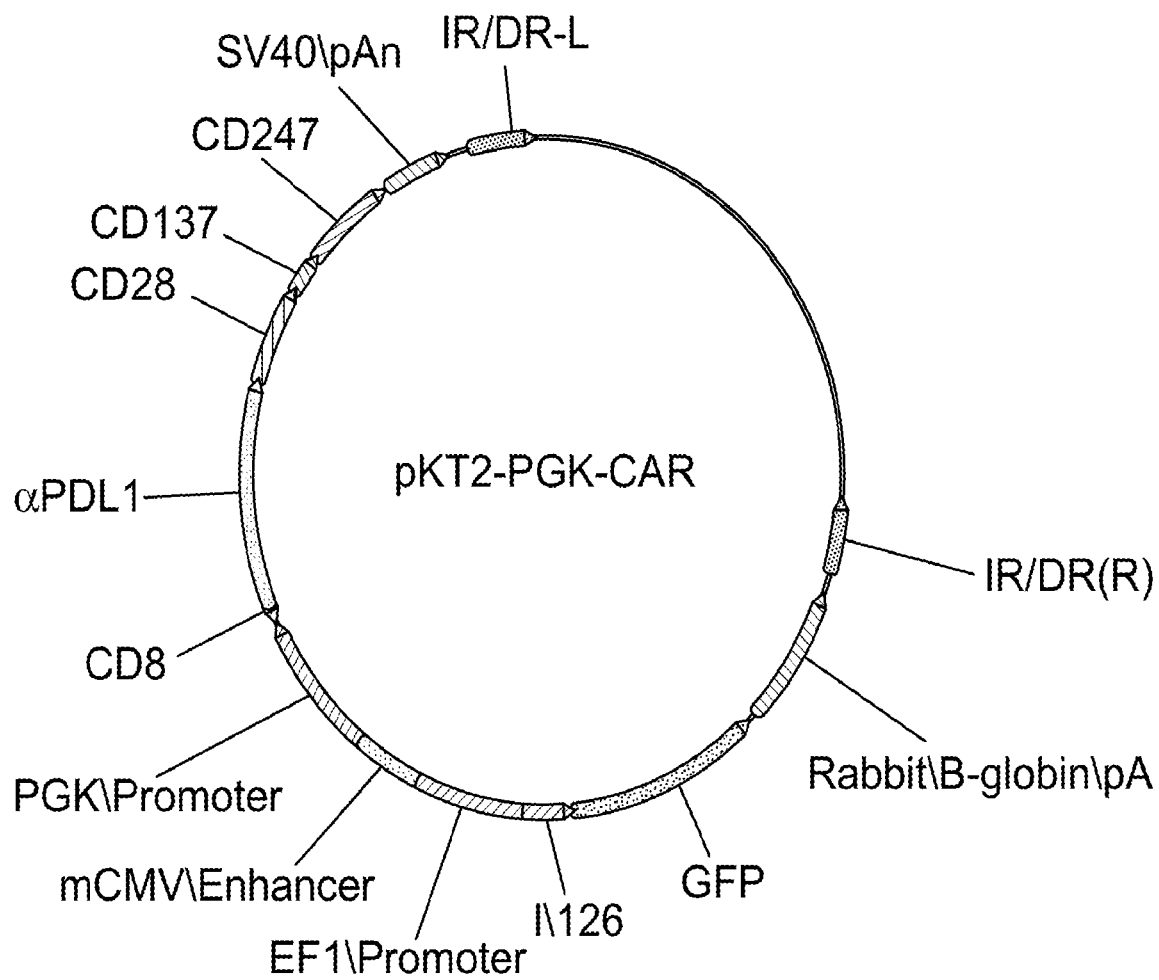
FIG. 15. pKT2-PGK-CAR plasmid map.
Figure 16:
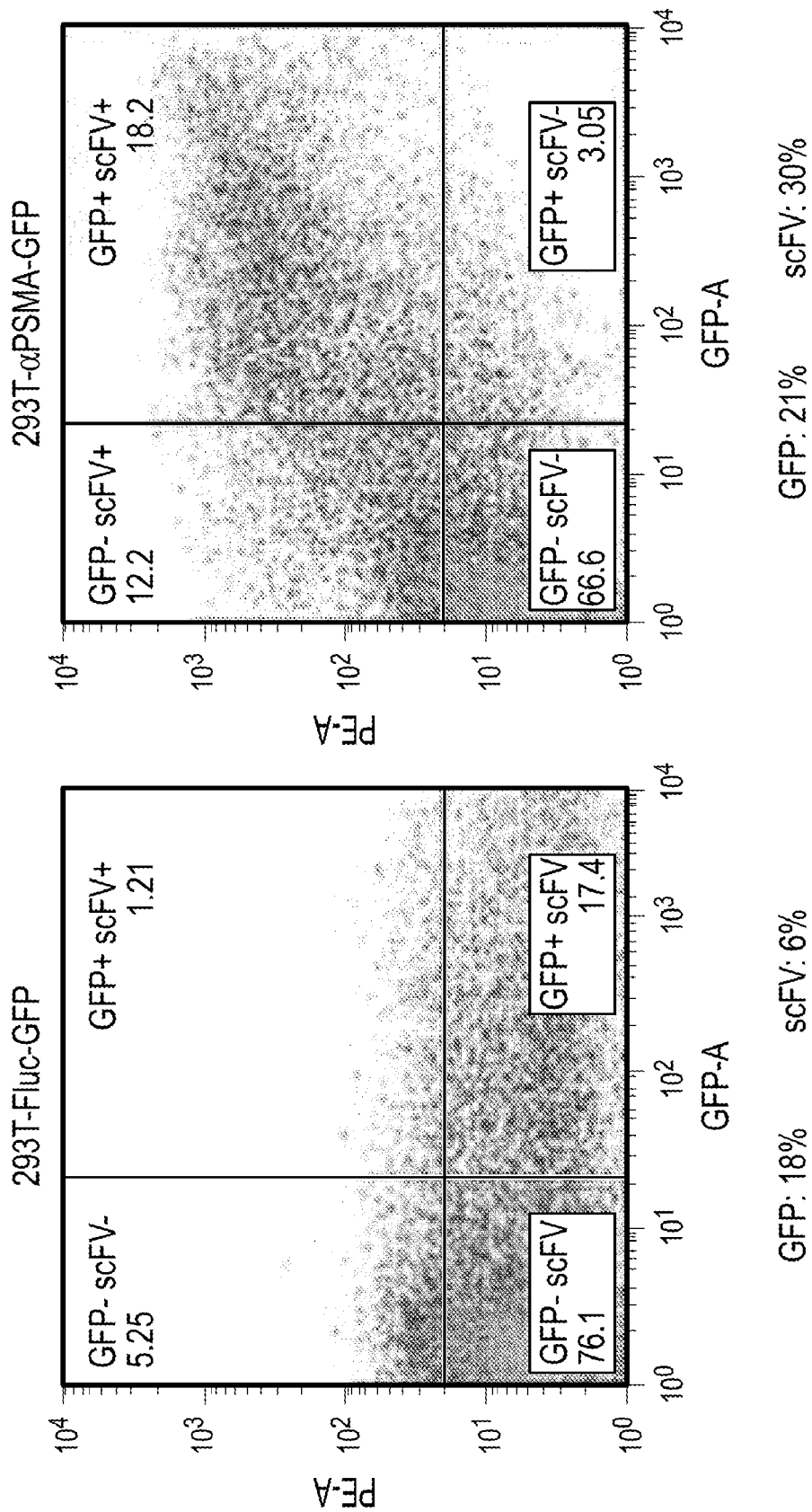
FIG. 16. Surface expression of anti-PSMA scFv detected by flow cytometry following transfection with expression plasmid.
Figure 16:
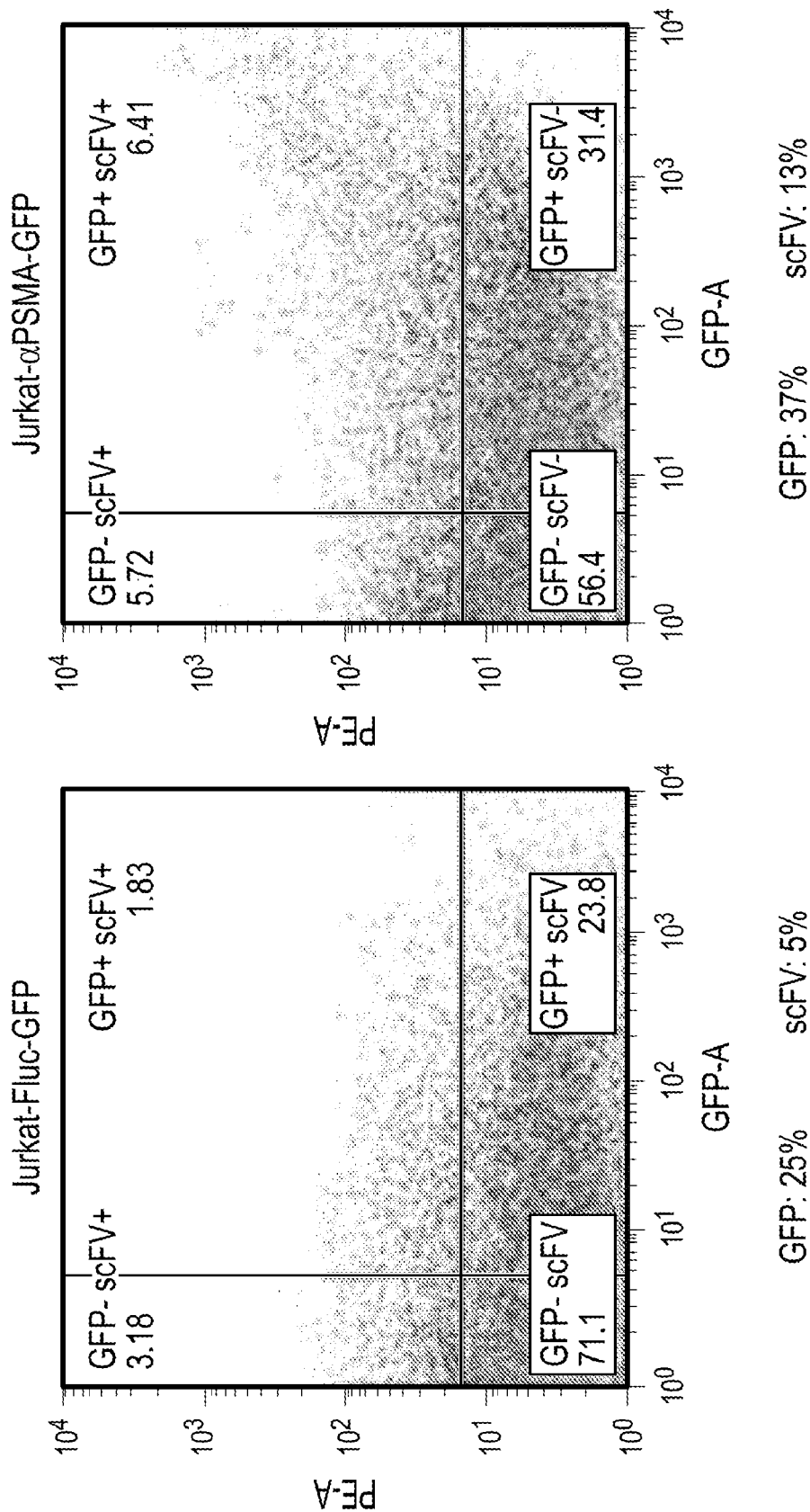

The resulting plasmid (FIG. 15) expresses, under PGK promoter control, a protein that includes the CD8 signal peptide followed by the scFv against PD-L1, and the costimulatory signaling domains CD28, CD137 (4-1BB), and the CD3 ζ chain (CD247). This construct also contains GFP (or GFP plus Puromycin resistance gene) under the control of the EF1 promoter for detection and transfection efficiency analysis. Control plasmids contain either nothing, Firefly luciferase, or αPMSA scFv in place of the αPD-L1 scFv. These control constructs were shown to express GFP, Firefly luciferase, and αPMSA scFv at the cell surface following transfection in 293T cells or Jurkat cells (FIG. 16).

Plasmids are transfected into PD-L1 negative cells such as 293T or Jurkat cells along with a vector expressing the SB 100X transposase to allow incorporation of the genes into the cell genome. Lentiviral transduction is also a method for delivery and incorporation of CARs into cells. Synthesis of the CAR is analyzed through Western blot analysis detected using an anti-CD3ζ chain antibody, and an anti-CD8 antibody and an anti-Fab antibody. Surface expression of the CAR is demonstrated by flow cytometry using an anti-Fab antibody as described for the αPMSA scFv construct herein.

Example 7—Generation of T Cells Expressing the PD-L1 Specific TCR and the Demonstration of PD-L1 Mediated Cytotoxicity when the Engineered T Cells are Placed in Contact with PD-L1 Positive Target Cells Construction of αPDL1 CAR T Cells Primary human CTLs are obtained by isolating PBMC from heparinized peripheral blood obtained from consenting healthy donors and enriching for CD8 T cells using an AutoMACs kit (Miltenyi Biotec, Inc.). T cells are maintained in RPMI-1640 with 10% human serum and activated with phytohemagglutinin (2 µg/mL) for two days. CTL cells are transduced with a bicistronic vector expressing αPD-L1 CAR and GFP. Flow cytometry is used to determine the transduction efficiency by quantifying the % of GFP positive cells.

Characterization of T Cell Costimulation Following PD-L1 Binding

Western Blot Analysis αPD-L1 CAR expressing CTL are stimulated with anti-human CD3 monoclonal antibody with or without recombinant human PD-L1 Fc chimera for 15 minutes. Cells are lysed in 1% Triton lysis buffer containing protease inhibitors. Proteins are fractionated by SDS-PAGE and transferred to PVDF membrane. Western blot analysis is conducted to detect ERK, phospho-ERK, AKT, and phospho-AKT or β-actin for normalization.

Expansion of CAR T Cells Following Antigen Stimulation

Peripheral blood CD8+ T cells are obtained from healthy donors and transduced with vectors expressing αPD-L1 CAR as described herein. CTLs are incubated with PD-L1 negative tumor cells such as 624mel cells or PD-L1 positive cells such as 624mel/B7-H1 cells in the presence of IL-2. CTLs are stimulated twice, once on day 0 and once on day 7. The absolute number of CAR T cells is determined on days 0, 7 and 14 using flow cytometry to detect GFP and CD8 positive T cells. Expansion of CAR T cells is observed when CTLs are incubated with PD-L1 positive cells.

Upregulated Cytokine and Granzyme B Release Following Antigen Stimulation

Peripheral blood CD8+ T cells are obtained from healthy donors and transduced with vectors expressing αPD-L1 CAR as described herein. CTLs are incubated with irradiated PD-L1 negative (e.g., 624mel) or PDL1 positive (e.g., 624mel/B7-H1) tumor cells in the presence of IL-2. At 24 hours post antigen stimulation, granzyme B expression is analyzed by Western blot detection. At 24 hours post antigen stimulation, TNFα expression is analyzed by ELISA. At 72 hours post antigen stimulation, IFN-γ expression is analyzed by ELISA. Expression levels of Granzyme B and both cytokines are only upregulated when CAR T cells are stimulated with PD-L1 positive cells.

Characterization of Cytotoxicity Against PD-L1 Positive Tumor Cells

Peripheral blood CD8+ T cells are obtained from healthy donors and transduced with vectors expressing αPD-L1 CAR as described herein. CTLs are incubated with PD-L1 negative tumor cells such as 624mel cells or PD-L1 positive cells such as 624mel/B7-H1 cells in the presence of IL-2 at various effector to target tumor cell ratios. CTLs are stimulated twice, once on day 0 and once on day 7. The cytolytic activity of antigen-stimulated CAR transduced CTLs is tested on day 7 using a standard $^{51}$Cr-release assay and is represented as percent lysis. Lysis of cells is only observed following stimulation with PD-L1 positive cells and is dependent upon effector:target ratio.

Example 8—Mouse-Anti-Human PD-L1 Antibody Clone 5H1

Figure 17A:
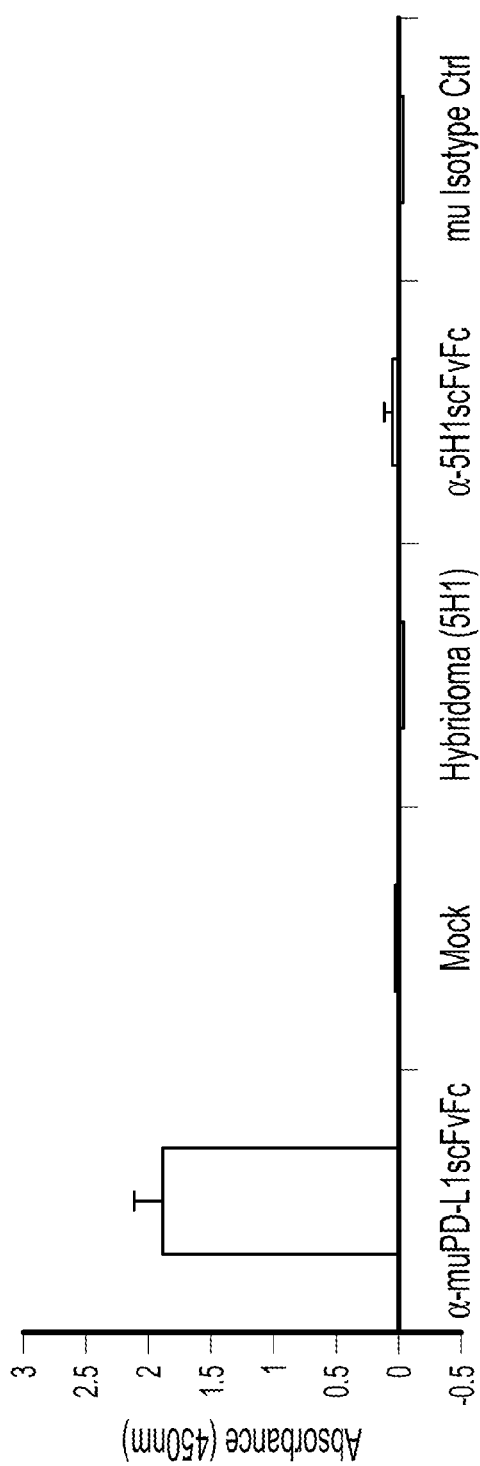
FIG. 17. The sa5H1 antibody binds specifically to huPD-L1 protein. (A) Bar graph showing binding of muPD-L1 (His tag) to cleared supernatants from 5H1 hybridoma cells or 293T cells transfected with pCG-samuPD-L1, pFUSE-sa5H1-mIgG1-Fc-Bsu36I, or empty vector. (B) Bar graph showing binding of huPD-L1 (hIgG1-Fc tag) to cleared supernatants from 5H1 hybridoma cells or 293T cells transfected with pCG-samuPD-L1, pFUSE-sa5H1-mIgG1-Fc-Bsu36I, or empty vector. Binding was assayed by ELISA and absorbance at 450 nm is shown.
Figure 17B:
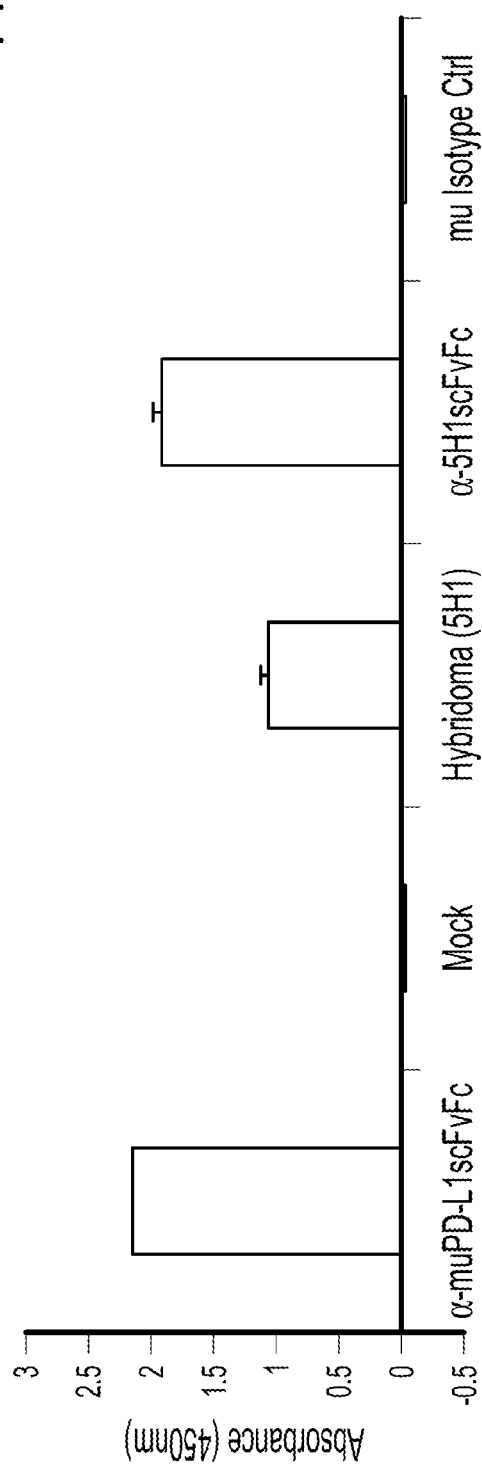

The sa5H1 Antibody Binds Specifically to huPD-L1 Protein $5 \times 10^5$ 293T cells were transfected with empty vector, pFUSE-sa5H1-mIgG1-Fc-Bsu36I, or pCG-samuPDL1 (pCG-samuPDL1 is an expression plasmid expressing an anti-PD-L1 single-chain Fc fusion antibody that binds human and mouse PD-L1). At 24 hours post transfection, the supernatant was collected and cleared through centrifugation at 1200 rpm for 5 minutes. Cleared supernatant was analyzed for binding to either muPD-L1 (His tag, FIG. 17A) or huPD-L1 (hIgG1-Fc tag, FIG. 17B) polypeptide (Life Technologies) via ELISA. Recombinant murine or human PD-L1 protein was diluted in coating solution (50 mM sodium carbonate, pH 9.6) to a final concentration of 5 µg/mL. 0.1 mL of protein coating solution was added to each well of a Nunc Maxisorp ELISA strip and incubated at 37° C. for 2 hours. All wells were washed five times with wash buffer (1×PBS, 0.1% tween-20). Wells were blocked with 3% blocking-grade blocker (Bio-Rad) in PBS overnight at 4° C. followed by washing five times in wash buffer. 0.1 mL of cleared supernatant, cleared hybridoma clone 5H1 supernatant, or 1 µg murine isotype control antibody (Pierce, Thermo Scientific) was added to an appropriate well and incubated at room temperature for 1 hour. For samuPDL1 samples a mouse-anti-HA tag-HRP high affinity antibody (Roche) at a concentration of 25 mU/mL in 3% blocking solution was used. For all other samples, a goat-anti-mIgG-HRP secondary antibody (Jackson ImmunoResearch) diluted 1:10,000 in 3% blocking solution was added and incubated at room temperature for 1 hour. After washing, the wells were incubated with 0.1 mL 1-Step Ultra TMB-ELISA substrate (Thermo Scientific) for 30 minutes at room temperature. The reaction was stopped using 0.1 mL 2M sulfuric acid, and the absorbance of the wells (450 nm) was measured with a microplate reader.

Figure 18A:
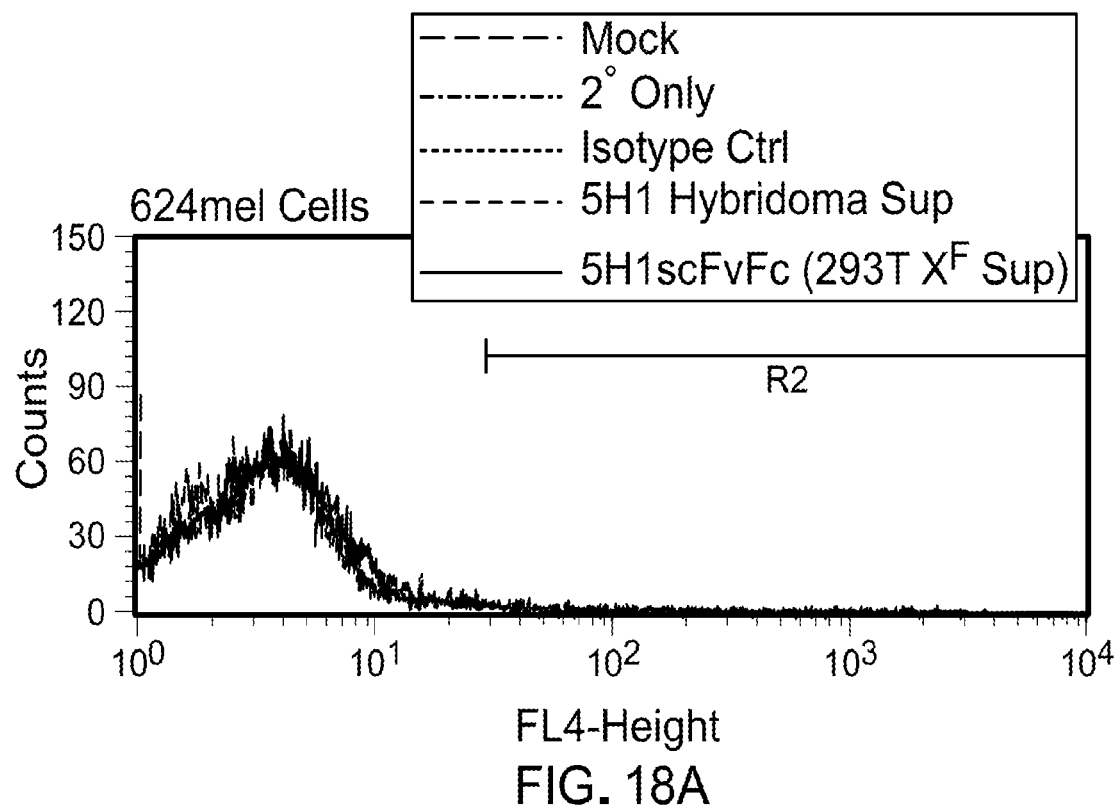
FIG. 18. Flow cytometry analysis showing that the sa5H1 antibody does not block the binding of recombinant human rhPD-1 protein to human PD-L1 protein similar to the 5H1-A3 purified whole molecule antibody. Mel 624 and B7H1/Mel 624 cells were incubated with cleared supernatants from 5H1 hybridoma cells, cleared supernatants from sa5H1 transfected 293 Ts, or with 1 μg of murine IgG isotype control antibody (Pierce, Thermo Scientific). The cells were subsequently incubated with recombinant human PD-1 Fc chimera protein (human IgG1 Fc tag). rhPD-1 binding was detected by flow cytometry using a DyLight 650 conjugated mouse anti-huIgG-Fc secondary antibody (Pierce). No rhPD-1 was included in the secondary only control. rhPD-1 binding (i.e. increased DyLight 650 fluorescence) was observed in all other samples. (A) Surface staining of Mel 624 cells. (B) Surface staining of B7H1/Mel 624 cells. X axes show DyLight 650 fluorescence intensity. Y axes show cell count.
Figure 18B:
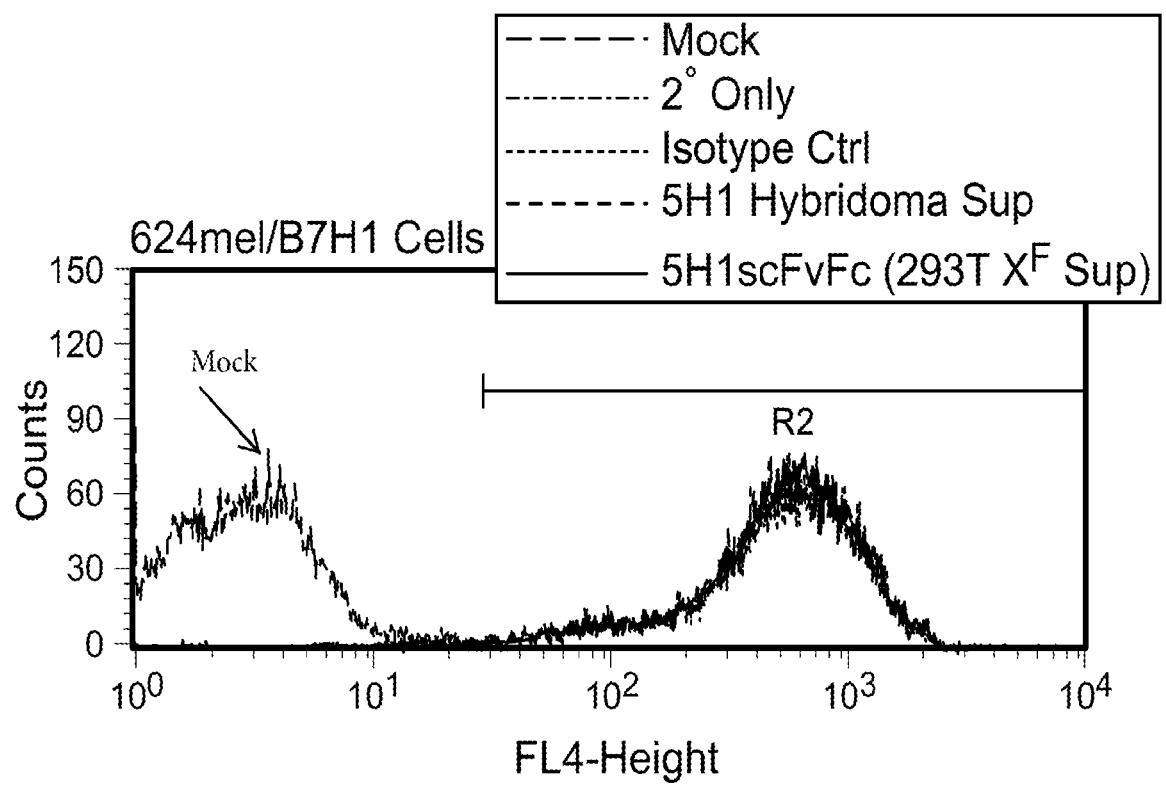

The sa5H1 Antibody does not Block Binding of a Recombinant Human PD-1 Fc Chimera Polypeptide (rhPD-1, R&D Systems) to huPD-L1 Protein Similar to the 5H1-A3 Purified Whole Molecule Antibody from a 5H1 Hybridoma Human melanoma cell lines Mel 624 or B7H/Mel 624 (constitutively expressing human PD-L1 (huPD-L1) protein) were used to analyze the ability of the sa5H1 antibody to block the binding of huPD-L1 to its natural receptor, human PD-1 (huPD-1). Cells were removed from flask surface with 10 mM EDTA, neutralized in propagation media (RPMI 1640, 10% FBS, 100 U/mL penicillin, 100 µg/mL streptomycin), washed, and resuspended at a concentration of $5 \times 10^6$ cells/mL. 0.1 mL of cell suspension was aliquotted into a clean microcentrifuge tube per sample, resuspended in 0.1 mL of cleared transfection supernatant (mock, pFUSE-sa5H1-mIgG1-Fc-Bsu36I), cleared hybridoma clone 5H1 supernatant or 1 µg murine isotype control antibody (Pierce, Thermo Scientific), and incubated on ice for 30 minutes. Cells were washed in ice-cold PBS, resuspended in 0.1 mL of recombinant huPD-1 protein at a concentration of 5 µg/mL in PBS, and incubated on ice for 30 minutes. Samples were washed with PBS, resuspended in 0.1 mL DyLight 650 conjugated mouse anti-human-IgG-Fc secondary antibody (Pierce) diluted 1:50 in PBS, and incubated for 30 minutes on ice in the dark. Cells were washed in ice-cold PBS and fixed in 4% paraformaldehyde for 10 minutes at room temperature. Cells were washed and resuspended in PBS, and binding was analyzed using flow cytometry. FIG. 18A shows surface staining of Mel 624 cells, while FIG. 18B shows surface staining of B7H1/Mel 624 cells.

VSV Encoding sa5H1 Antibody Gene Replicates and Spreads with Slightly Reduced Kinetics Compared to VSV-eGFP Control BHK cells were infected with VSV-eGFP or VSV-sa5H1-eGFP at an MOI of 3 (single-step analysis, FIG. 19A) or 0.1 (multi-step analysis, FIG. 19B) in Opti-MEM for 2 hours at 37° C. Supernatant and unabsorbed virus was removed, and cells were washed and resuspended in propagation media (DMEM, 10% FBS, 100 U/mL penicillin, 100 μg/mL). Supernatants and cell lysates were collected at 2, 4, 6, 8, 10, 12, and 24 hours post infection. Samples were lysed by freeze/thawing three times, and cleared by centrifugation at 2500 rpm for 5 min, and the $TCID_{50}$ was determined on Vero cells as described herein.

The sa5H1 Antibody Produced by VSV-sa5H1-eGFP Infected BHK Cells Binds Specifically to Human PD-L1 (Hu-PL-L) Protein $5\times10^5$ BHK cells were infected with VSV-eGFP, VSV-samuPDL1-eGFP or VSV-sa5H1-eGFP at an MOI of 3 for 2 hours in Opti-MEM at 37° C. At 2 hours post-infection, the supernatant and unabsorbed virus was removed, cells were washed with propagation media (DMEM, 10% FBS, 100 U/mL penicillin, 100 μg/mL streptomycin), and 1.5 mL of propagation media was added. Cells were incubated at 37° C., and samples were collected at 2, 4, 6, 8, 12, and 24 hours post-infection. At each time point, the supernatant was collected and cleared through centrifugation at 1200 rpm for 5 minutes. Cleared supernatant was analyzed for binding to either murine PD-L1 (muPD-L1) (His tag, FIG. 20A) or huPD-L1 (hIgG1-Fc tag, FIG. 20B) polypeptide (Life Technologies) via ELISA. Recombinant murine or human PD-L1 protein was diluted in coating solution (50 mM sodium carbonate, pH 9.6) to a final concentration of 5 μg/mL. 0.1 mL of protein coating solution was added to each well of a Nunc Maxisorp ELISA strip and incubated at 37° C. for 2 hours. All wells were washed five times with wash buffer (1×PBS, 0.1% tween-20). Wells were blocked with 3% blocking-grade blocker (Bio-Rad) in PBS overnight at 4° C. followed by washing five times in wash buffer. 0.1 mL of cleared supernatant, cleared hybridoma clone 5H1 supernatant, or 1 gig murine isotype control antibody (Pierce, Thermo Scientific) was added to an appropriate well and incubated at room temperature for 1 hour. Wells were washed five times with wash buffer and 0.1 mL of secondary antibody was added. For VSVsamuPDL1-eGFP (VSV encoding eGFP and single-chain Fc fusion antibody that recognizes human and mouse PD-L1) samples, a mouse-anti-HA tag-HRP high affinity antibody (Roche) at a concentration of 25 mU/mL in 3% blocking solution was used. For all other samples, a goat-anti-mouse-IgG-HRP secondary antibody (Jackson ImmunoResearch) diluted 1:10,000 in 3% blocking solution was added and incubated at room temperature for 1 hour. After washing, the wells were incubated with 0.1 mL 1-Step Ultra TMB-ELISA substrate (Thermo Scientific) for 30 minutes at room temperature. The reaction was stopped using 0.1 mL 2M sulfuric acid, and the absorbance of the wells (450 nm) was measured with a microplate reader.

VSV Encoding sa5H1 Antibody Maintains Cytolytic Activity Against Murine Myeloma 5TGM1 Cells 5TGM1 cells were infected with VSV-eGFP, VSV-samuPDL1-eGFP, or VSV-sa5H1-eGFP at an increasing MOI (0, 0.001, 0.01, 0.1, 1, or 10) in Opti-MEM for 2 hours at 37° C. Following infection, cells were washed and seeded into 96-well plates at $1\times10^4$ cells/well in propagation media (IMDM, 10% FBS, 100 U/mL penicillin, 100 μg/mL streptomycin). Cells were incubated at 37° C., and viable cell proliferation was measured at 24 (FIG. 21A), 48 (FIG. 21B), and 72 (FIG. 21C) hours post-infection using the MTT (3-(4,5-dimethylthiazolyl-2)-2,5-diphenyltetrazolium bromide) assay (ATCC). Data were represented as percent viability of mock infected cells+/−standard deviation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, wherein said method comprises administering a genetically modified virus that expresses a chimeric polypeptide comprising a PD-L1 targeting domain and an effector domain on its surface under conditions wherein the virus is capable of infecting a cancer cell expressing PD-L1, wherein the PD-L1 targeting domain comprises an antibody single-chain variable fragment, wherein the antibody single-chain variable fragment comprises an amino acid sequence encoded by a nucleotide sequence having at least 90% identity to the nucleotide sequence of SEQ ID NO:1.

2. The method of claim 1, wherein the antibody single-chain variable fragment comprises an amino acid sequence encoded by the nucleotide sequence of SEQ ID NO:1.

3. A method for treating cancer in a mammal, wherein said method comprises administering a genetically modified virus that expresses a chimeric polypeptide comprising a PD-L1 targeting domain and an effector domain on its surface under conditions wherein the virus is capable of infecting a cancer cell expressing PD-L1, wherein the PD-L1 targeting domain comprises an antibody single-chain variable fragment, wherein the antibody single-chain variable fragment comprises an amino acid sequence encoded by a nucleotide sequence having at least 90% identity to the nucleotide sequence of SEQ ID NO:2.

4. The method of claim 3, wherein the antibody single-chain variable fragment comprises an amino acid sequence encoded by the nucleotide sequence of SEQ ID NO:2.

5. The method of claim 1, wherein the polypeptide comprising a PD-L1 targeting domain further comprises a hemagglutinin domain.

6. The method of claim 5, wherein the hemagglutinin domain is selected from the group consisting of: a measles virus H glycoprotein polypeptide, a canine distemper virus H glycoprotein polypeptide, a nipah virus H glycoprotein polypeptide, a rinderpest virus H glycoprotein polypeptide, and a phocine distemper virus H glycoprotein polypeptide.

7. The method of claim 5, wherein the hemagglutinin domain comprises a modified hemagglutinin domain comprising one or more substitutions, insertions, or deletions, such that the modified hemagglutinin domain exhibits reduced binding to a cellular polypeptide.

8. The method of claim 7, wherein the cellular polypeptide is selected from the group consisting of: complement regulatory molecule CD46, the signaling lymphocyte activation molecule (SLAM), and Nectin-4.

9. A method for treating cancer in a mammal, wherein said method comprises administering a genetically modified virus that expresses a chimeric polypeptide comprising a PD-L1 targeting domain and an effector domain on its surface under conditions wherein the virus is capable of infecting a cancer cell expressing PD-L1, wherein the effector domain comprises an antibody single-chain variable fragment that binds a CD3 polypeptide, wherein the chimeric polypeptide comprises an amino acid sequence at least 95% identical to the amino acid sequence of SEQ ID NO:6.

10. A method for treating cancer in a mammal, wherein said method comprises administering a genetically modified virus that expresses a chimeric polypeptide comprising a PD-L1 targeting domain and an effector domain on its surface under conditions wherein the virus is capable of infecting a cancer cell expressing PD-L1, wherein the effector domain comprises an antibody single-chain variable fragment that binds a CD3 polypeptide, wherein the chimeric polypeptide comprises the amino acid sequence of SEQ ID NO:6.

11. A method for treating cancer in a mammal, wherein said method comprises administering a genetically modified virus that expresses a chimeric polypeptide comprising a PD-L1 targeting domain and an effector domain on its surface under conditions wherein the virus is capable of infecting a cancer cell expressing PD-L1, wherein the effector domain comprises an antibody single-chain variable fragment that binds a CD3 polypeptide, wherein the chimeric polypeptide comprises an amino acid sequence at least 95% identical to the amino acid sequence of SEQ ID NO:8.

12. A method for treating cancer in a mammal, wherein said method comprises administering a genetically modified virus that expresses a chimeric polypeptide comprising a PD-L1 targeting domain and an effector domain on its surface under conditions wherein the virus is capable of infecting a cancer cell expressing PD-L1, wherein the effector domain comprises an antibody single-chain variable fragment that binds a CD3 polypeptide, wherein the chimeric polypeptide comprises the amino acid sequence of SEQ ID NO:8.

13. The method of claim 3, wherein the polypeptide comprising a PD-L1 targeting domain further comprises a hemagglutinin domain.

14. The method of claim 13, wherein the hemagglutinin domain is selected from the group consisting of: a measles virus H glycoprotein polypeptide, a canine distemper virus H glycoprotein polypeptide, a nipah virus H glycoprotein polypeptide, a rinderpest virus H glycoprotein polypeptide, and a phocine distemper virus H glycoprotein polypeptide.

15. The method of claim 13, wherein the hemagglutinin domain comprises a modified hemagglutinin domain comprising one or more substitutions, insertions, or deletions, such that the modified hemagglutinin domain exhibits reduced binding to a cellular polypeptide.

16. The method of claim 15, wherein the cellular polypeptide is selected from the group consisting of: complement regulatory molecule CD46, the signaling lymphocyte activation molecule (SLAM), and Nectin-4.

* * * * *